(12) United States Patent
Chien et al.

(10) Patent No.: US 8,420,612 B2
(45) Date of Patent: Apr. 16, 2013

(54) DIABETES TREATMENT METHODS AND DRUG TARGETS THEREFOR

(75) Inventors: Kenneth Chien, Cambridge, MA (US); Lisa Lesniewski, Boulder, CO (US); Jerrold Olefsky, Solana Beach, CA (US); Mohammad Pashmforoush, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1179 days.

(21) Appl. No.: 11/625,795

(22) Filed: Jan. 22, 2007

(65) Prior Publication Data

US 2007/0190035 A1    Aug. 16, 2007

Related U.S. Application Data

(60) Provisional application No. 60/760,841, filed on Jan. 20, 2006.

(51) Int. Cl.
| | |
|---|---|
| *A61K 48/00* | (2006.01) |
| *C12N 15/11* | (2006.01) |
| *A01N 63/00* | (2006.01) |
| *C12N 15/00* | (2006.01) |
| *C12N 5/00* | (2006.01) |
| *C12N 5/071* | (2010.01) |

(52) U.S. Cl.
USPC .... 514/44 R; 424/93.1; 424/93.2; 424/93.71; 435/320.1; 435/325; 435/372; 514/44 A

(58) Field of Classification Search .................. None
See application file for complete search history.

(56) References Cited

FOREIGN PATENT DOCUMENTS

| WO | WO 2004/055181 | * | 7/2004 |
|---|---|---|---|
| WO | WO 2006/023121 A1 | | 3/2006 |

OTHER PUBLICATIONS

Caveggion et al., 2003, J. Cellular Physiology 195:276-289.*
Molero et al., 2004; J. Clin. Invest. 114:1326-1333.*
Permana et al., Jan. 2006, BBRC 341:507-514.*
Baumann., 2000, Nature 407:202-206.*

* cited by examiner

*Primary Examiner* — Robert M Kelly
*Assistant Examiner* — Kelaginamane T Hiriyanna
(74) *Attorney, Agent, or Firm* — Sutherland Asbill & Brennan LLP

(57) ABSTRACT

Provided are methods of treating insulin resistance or type II diabetes. Disrupting CAP in the macrophage can alter the inflammatory response associated with impaired insulin action and ultimately result in improved insulin action in target tissues. One aspect of the invention involves administering a CAP antagonist to a patient afflicted with insulin resistance or type II diabetes in an amount sufficient to improve insulin action in target tissues.

20 Claims, 16 Drawing Sheets

Figure 12

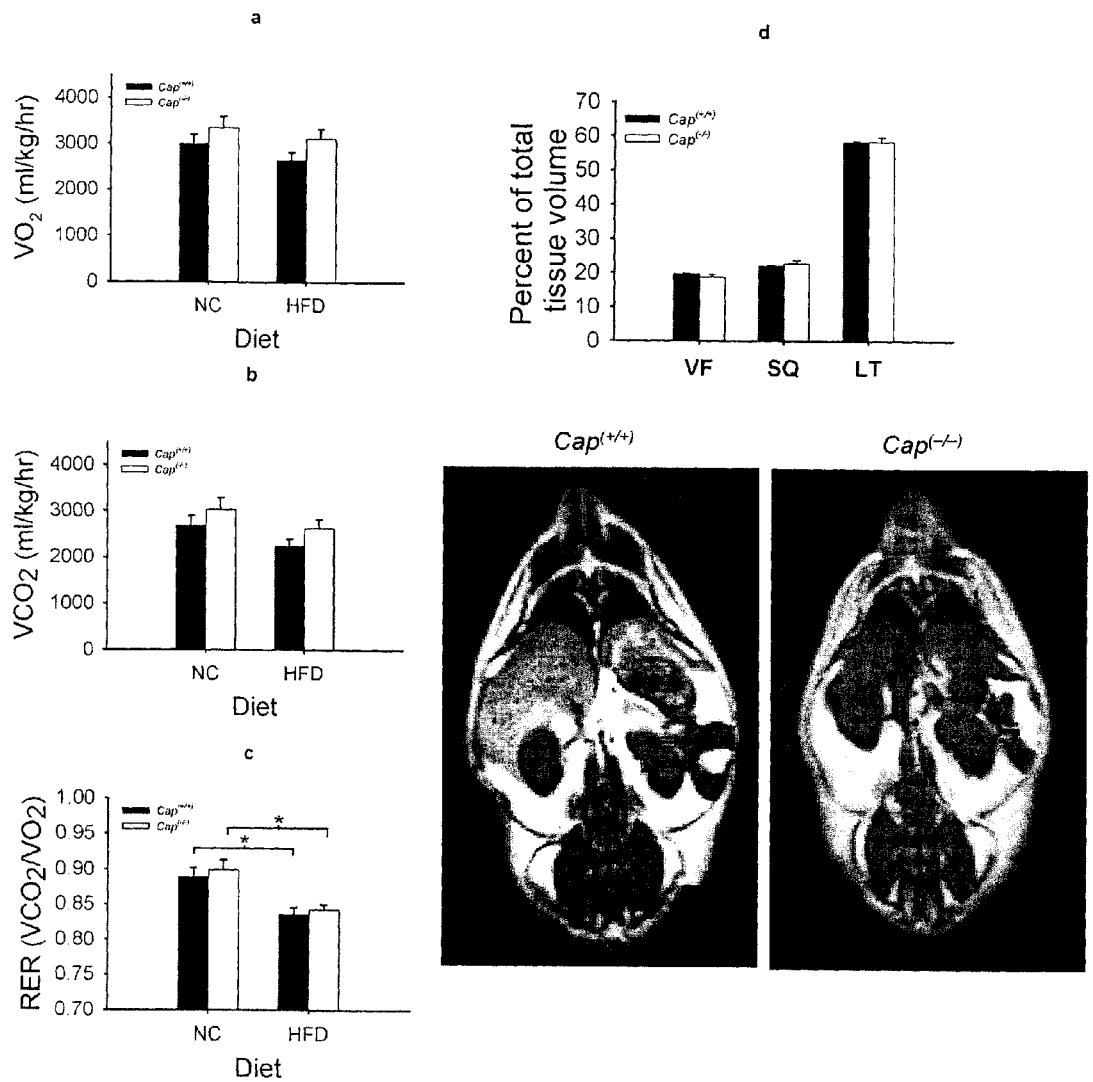

Supplemental Figure. No differences in metabolism or body composition between $Cap^{(+/+)}$ and $Cap^{(-/-)}$ mice. (a) Oxygen consumption ($VO_2$), (b) carbon dioxide release ($VCO_2$), and (c) respiratory exchange ratio (RER) in $Cap^{(+/+)}$ and $Cap^{(-/-)}$ mice fed NC and HFD. (d) Body composition following HFD assessed by MRI, data presented as percent of total tissue volume. VF: visceral fat, SQ: subcutaneous fat, LT: lean tissue. * $P<0.05$, values are mean ± sem.

DIABETES TREATMENT METHODS AND DRUG TARGETS THEREFOR

CROSS-REFERENCE TO RELATED APPLICATIONS

This application claims priority to U.S. Provisional Patent Application 60/760,841 filed Jan. 20, 2006, which is hereby incorporated by reference in its entirety.

GOVERNMENT SUPPORT

This invention was made in part with Government support under Grant No. DK 33651 awarded by the National Institutes of Health. The Government has certain rights in the invention.

INCORPORATION-BY-REFERENCE OF MATERIAL SUBMITTED ON A COMPACT DISC

Not Applicable.

FIELD

The present disclosure generally relates to diabetes drug targets and methods of diabetes treatment.

BACKGROUND

There has been increasing evidence supporting a role of inflammation in impaired insulin action in peripheral tissues in both humans and animal models of insulin resistance and type 2 diabetes. CAP (Cbl associated protein), a ubiquitously expressed adapter protein whose expression has been described in both adipose and skeletal muscle tissues, is believed to act in concert with Cbl (the Cbl/CAP pathway) to stimulate glucose uptake in peripheral insulin sensitive tissues such as skeletal muscles and adipose tissue. The Cbl/CAP pathway has also been shown to be involved in the proliferation and motility of macrophages, which are recruited to these tissues in response to inflammatory stimuli.

Data from cultured adipocytes support a role of a Cbl/CAP complex in insulin stimulated glucose uptake. Transfection of 3T3-L1 adipocytes with a non-functional CAP results in a near complete inhibition of GLUT4 translocation and glucose uptake (Chiang, S. H., et al., Nature 410: 944-948, 2001; Liu, J., et al., J. Biol. Chem. 278: 36754-36762, 2003). However, in 3T3-L1 adipocytes siRNA silencing of Cbl, CAP or Crkll was ineffective at diminishing glucose uptake in response to insulin stimulation (Mitra, P. et al., J. Biol. Chem. 279: 37431-37435, 2004). Thirone, A. C., et al., (Endocrinology 145: 281-93, 2004) described higher expression of Cbl in adipose tissue compared to muscle in rats with no detectable CAP in muscle homogenates. Wadley, G. D., et al. (Diabetologia 47: 412-419, 2004) demonstrated CAP expression in skeletal muscle, but described higher levels of CAP expression in 3T3-L1 adipocytes than in soleus muscle from Zucker rats. Despite these decrepancies in tissue specific CAP expression, the protein content and phosphorylation state appears to be sensitive to alterations in whole body insulin sensitivity. For example, basal skeletal muscle Cbl phosphorylation can be increased in insulin-resistant rats relative to lean controls (Wadley, G. D., et al. Diabetologia 47: 412-419, 2004). Likewise, in adipose tissue, induction of insulin-resistance in rats can result in increased expression of both Cbl and CAP, as well as an increase in both their association and phosphorylation in response to insulin stimulation.

In addition to activation of pathways downstream of receptor tyrosine kinases (RTKs), Cbl has also been shown to exert a dampening role by stimulating the ubiquitination and subsequent degradation of the ligand-bound RTKs (Duan, L., et al., Immunity 21: 7-17, 2004). This dual and opposing role of Cbl can be illustrated by the actions of Cbl downstream of the activated RTK, colony stimulating factor-1 (CSF-1). Lee, P. S., et al. (EMBO J. 18: 3616-3628 1999) demonstrated that Cbl activity negatively regulated macrophage proliferation via receptor ubitiquination. Activation of Cbl in macrophages can also control proliferation, survival, differentiation, adhesion and cell motility via downstream Crkll activation (Erdreich-Epstein, A., et al., J. Leukoc. Biol. 65:523-534, 1999; Caveggion, E., et al., J. Cell Physiol. 195: 276-89, 2003; Husson, H. et al., Oncogene 14: 2331-2338, 1997; Wang, Y., et al., J. Cell Biochem. 72: 119-134).

Macrophage infiltration of adipose tissue and intramuscular fat is known to occur in obesity (Weisberg, S. P., et al., J. Clin. Invest. 112: 1796-1808, 2003; Xu, H., et al., J. Clin. Invest. 112: 1821-1830, 2003). In addition, tissue levels of inflammatory markers such as tumor necrosis factor-alpha (TNF-α), interleukin-6 (IL-6), monocyte chemotactic protein-1 (MCP-1) and inducible nitric oxide synthase (iNOS) are also elevated in obesity and are believed to be derived from the infiltrating macrophages (Weisberg, S. P., et al., J. Clin. Invest. 112: 1796-1808, 2003). Moreover, increased expression of inflammatory genes can be evident as early as 3 weeks after the introduction of a high fat diet, with worsening severity at the onset of hyperinsulinemia (Xu, H., et al., J. Clin. Invest. 112: 1821-1830, 2003). However, previous studies do not reveal if the adaptor protein, CAP, is present and/or essential to normal inflammatory activity of macrophages, nor do they disclose therapies involving inhibition of CAP expression or activity

SUMMARY

The present inventors have developed methods of treatment of insulin resistance and type II diabetes. These methods comprise administration to a subject in need of treatment for insulin resistance and/or type II diabetes of compounds which inhibit or interfere with the CAP/Cbl pathway.

Accordingly, the present teachings include methods for treating insulin resistance in a subject. These methods comprise administering to a subject in need of treatment a composition containing a therapeutically effective amount of an inhibitor of CAP expression or activity.

Further aspects of the present teachings provide methods for treating type 2 diabetes in a subject. These methods comprise administering to a subject in need of treatment a composition containing a therapeutically effective amount of an inhibitor of CAP expression or activity.

Yet additional aspects of the present teachings provide methods for protecting a subject from high fat diet induced whole body insulin resistance. These methods comprise administering to a subject in need thereof a composition containing a therapeutically effective amount of an inhibitor of CAP expression or activity.

Other aspects of the present teachings provide methods for disrupting an inflammatory process associated with insulin resistance in a subject by administering to a subject in need thereof a composition containing a therapeutically effective amount of an inhibitor of CAP expression or activity.

Hence, various aspects of the present teachings include in vitro cell cultures comprising macrophages having reduced CAP activity in comparison to macrophages comprised by a subject in need of treatment, as well as methods of treating a disease or disorder involving insulin metabolism in a subject. In some aspects, these methods comprise a) providing an in vitro cell culture comprising macrophages having reduced CAP activity in comparison to macrophages comprised by a subject in need of treatment; and b) administering cells comprised by the in vitro cell culture to the subject. In various aspects, a subject can be any mammal, such as a mouse or a human, including a human in need of treatment.

In some configurations, providing an in vitro cell culture can comprise introducing a cell population comprising macrophages into an in vitro cell culture, and inhibiting CAP gene expression in cells comprised by the in vitro cell culture. In some configurations, introducing a cell population comprising macrophages can comprise introducing a stem cell population to the cell culture, and differentiating the stem cells comprised by the population into macrophages. In various configurations, the stem cell population can comprise haematopoietic stem cells, bone marrow stem cells (such as mesenchymal stem cells), umbilical cord stem cells, embryonic stem cells or various combinations thereof. In yet other configurations, a cell population comprising macrophages can comprise bone marrow cells.

In some aspects of the present teachings, inhibiting CAP gene expression in cells comprised by an in vitro cell culture can comprise disrupting or deleting the CAP gene comprised by the macrophages or precursors thereof, such as by introducing an insertion into the CAP gene by homologous recombination. Furthermore, cells in which the CAP gene is disrupted or deleted can be selected using standard methods known to skilled artisans, such as by inclusion of a selection marker in the insertion. In some configurations, cells in which the CAP gene is disrupted or deleted can be grown in vitro prior to their administration to a subject.

In some configurations, a cell population comprising macrophages can be autologous to a subject such as a human in need of treatment. In other configurations, the cell population can be syngeneic or allogeneic to the subject.

In various aspects, the disease or disorder involving insulin metabolism can include insulin resistance, type 2 diabetes, insulin-resistance associated inflammation or a combination thereof. In some configurations, the insulin resistance can be high fat diet-induced whole body insulin resistance.

An in vitro cell culture of the present teachings can include macrophages comprising a deletion or disruption of the CAP gene. Furthermore, the macrophages can be autologous to a subject such as an intended recipient of the macrophages comprising the disrupted or deleted CAP gene. In some related configurations, the macrophages can be syngeneic to the subject or allogeneic to the subject. In addition, an in vitro cell culture can comprise bone marrow cells, and/or macrophage precursor cells such as stem cells. In various configurations, the stem cells can be, without limitation, haematopoietic stem cells, bone marrow stem cells (such as mesenchymal stem cells), umbilical cord stem cells, embryonic stem cells or combinations thereof.

BRIEF DESCRIPTION OF THE DRAWINGS

FIG. 1A is a map depicting exons and introns of the major transcripts and splice variants of CAP also known as SH3P12 (Ponsin). Three non-coding exons in the 5' region of the gene are shown in the upper panel. FIG. 1B is a map indicating the two exons common to all of known SH3P12 transcripts in the public database removed in the generation of the null mutant. This deletion introduces a frameshift in the codon reading frame. The frameshift results in the premature termination of translation. The 3 kb BamHI fragment containing two exons was eliminated in the targeting construct. FIG. 1C is an image of a Southern blot showing Hind III digests of DNA isolated from wild type and the targeted allele which resulted in an approximately 8 kb and 5 kb fragments, respectively.

FIG. 2A is a line and scatter plot depicting glucose levels measured during the glucose tolerance test as a function of time for WT NC, CAPKO NC, WT HFD, and CAPKO HFD. FIG. 2B is a box plot depicting plasma insulin concentrations measured during the glucose tolerance test as a function of time for WT NC, CAPKO NC, WT HFD, and CAPKO HFD. FIG. 2C is a line and scatter plot depicting glucose levels measured during the insulin tolerance tests as a function of time for WT NC, CAPKO NC, WT HFD, and CAPKO HFD. Elevations in blood glucose during both the glucose and insulin tolerance tests in WT mice fed HFD are indicative of altered glucose metabolism consistant with the development of insulin resistance. The lack of increase in blood glucose during both tests in high fat fed CAPKO mice suggests that CAP gene deletion is conferring protection from high fat diet-induced insulin resistance.

FIG. 3A is a box plot showing decreased insulin-stimulated glucose disposal rate (IS-GDR) for WT and CAPKO mice fed NC and HFD. FIG. 3B is a box plot showing suppression of hepatic glucose output for WT and CAPKO mice fed NC and HFD. FIG. 3C is a box plot showing change in plasma free fatty acids for WT and CAPKO mice fed NC and HFD. These trends are consistent with the development of insulin resistance in the WT mice. As seen in the figures, CAP deletion protected all three primary insulin sensitive tissues from high fat diet-induced changes in insulin sensitivity.

FIG. 4 is a series of images showing immunohistochemical staining for the macrophage marker, F4/80+ of adipose tissue.

FIG. 5 is a series of line and scatter plots showing data from mice that received bone marrow transplantation (BMT) of either WT marrow or marrow collected from CAPKO mice. These data demonstrate that the overall effect of CAP gene deletion in the macrophage is improved whole body insulin sensitivity following high fat diet.

FIG. 6 is a series of images showing immunohistochemical staining for the macrophage marker, F4/80+ of adipose tissue.

FIG. 8a, b shows that no differences in glucose or insulin tolerance were observed between $Cap_{(+/+)}$ and $Cap_{(-/-)}$ mice while fed NC. Surprisingly, even when maintained on NC, the glucose infusion rate ($P=0.04$) and glucose disposal rate ($P=0.07$) were both higher (~40%) in the $Cap_{(-/-)}$ compared to $Cap_{(+/+)}$ mice (FIG. 8c, d). Strikingly, the $Cap_{(+/+)}$ mice developed the expected impaired glucose and insulin tolerance following HFD, but the $Cap_{(-/-)}$ mice were protected from HFD-induced defects in glucose and insulin homeostasis (FIG. 8a, b). We found a significant decrease in plasma insulin at 60 and 120 min of the GTT in HFD $Cap_{(-/-)}$ mice compared to the $Cap_{(+/+)}$ mice, consistent with the improved glucose tolerance (FIG. 8a, lower panel). These observations were further supported by euglycemic clamp studies, in which HFD-induced the usual state of insulin resistance in the $Cap_{(+/+)}$ mice, as manifested by a decrease in glucose infusion rate, glucose disposal rate, suppression of hepatic glucose output, and suppression of circulating free fatty acids (FIG. 8c-f). In marked contrast, each measurement of insulin sensitivity in skeletal muscle (GDR), liver (HGO suppression), and adipose tissue (FFA levels) remained normal in the $Cap_{(-/-)}$ mice despite HFD (FIG. 8c-f). Enhanced signaling through the P13K pathway may explain the maintenance of insulin sensitivity in the HFD $Cap_{(-/-)}$ mice. Indeed, we found increased phosphorylation of Akt following 15 min of insulin stimulation in both the WAT and skeletal muscle of $Cap_{(-/-)}$ mice compared to $Cap_{(+/+)}$ controls following HFD (FIG. 8g). Adipocyte $Cap_{(-/-)}$ leads to increased insulin sensitivity, even when mice are maintained on NC diet. Ex vivo lipogenesis experiments reveal an increase in insulin-stimulated glucose incorporation into lipid in adipocytes isolated from $Cap_{(-/-)}$ mice compared to those from $Cap_{(+/+)}$ mice (FIG. 8h), a finding that indicates enhanced insulin sensitivity in the adipose tissue of the $Cap_{(-/-)}$ mice.

FIG. 9b demonstrates that while circulating MCP-1 levels increased in $Cap_{(+/+)}$ mice following HFD, MCP-1 was unaltered in $Cap_{(-/-)}$ mice, suggesting a decrease in adipose tissue macrophage content in $Cap_{(-/-)}$ mice. Indeed, as assessed by staining for F4/80+ cells in histological sections of adipose tissue, we show a marked (80%) reduction in adipose tissue macrophage content in the $Cap_{(-/-)}$ mice compared to $Cap_{(+/+)}$ mice on either NC or HFD (FIG. 9c). Furthermore, there was a significant reduction in both phosphorylated IKK-® ($P<0.01$) and JNK ($P<0.05$) in the WAT of $Cap_{(-/-)}$ mice compared to wild type mice when fed HFD (FIG. 9d).

FIG. 10a shows that show that Cap is expressed in both primary blood derived monocytes and in the immortalized macrophage cell lines, RAW264.7 and J774A, both of which are available from American Type Culture Collection. The BMT-$Cap_{(+/+)}$ animals on HFD were glucose intolerant (FIG. 10b, upper panel) and hyperinsulinemic (FIG. 10b, lower panel) compared to the BMT-$Cap_{(-/-)}$ mice. Similarly, the ITTs (FIG. 10c) showed enhanced overall insulin sensitivity in the BMT-$Cap_{(-/-)}$ mice compared to BMT$Cap_{(+/+)}$. This protection from HFD-induced insulin resistance in the BMT-$Cap_{(-/-)}$ was further supported by euglycemic clamp studies (FIG. 10d-f), which demonstrated higher glucose infusion rates, glucose disposal rates, and suppression of hepatic glucose output in the BMT-$Cap_{(-/-)}$ mice compared to BMT-$Cap_{(+/+)}$. In BMT experiments, all of the hematopoietic lineages are reconstituted from donor mice and, therefore, any BM cell type which normally expresses Cap would show Cap deletion. However, since there is no evidence in the literature that lymphocytes or granulocytes play any role in the chronic inflammation which leads to insulin resistance, we conclude that the insulin sensitive phenotype in the BMT-$Cap_{(-/-)}$ is related to Cap knockout in the macrophage lineage.

FIG. 12 illustrates that no differences in $VO_2$, $VCO_2$, food consumption or spontaneous cage activity were seen between genotypes, although RER decreased in both the $Cap_{(+/+)}$ and $Cap_{(-/-)}$ mice following HFD when spontaneous cage activity and metabolic rate were assessed in $Cap_{(+/+)}$ and $Cap_{(-/-)}$ mice on both NC and HFD.

DETAILED DESCRIPTION

Figure 1:
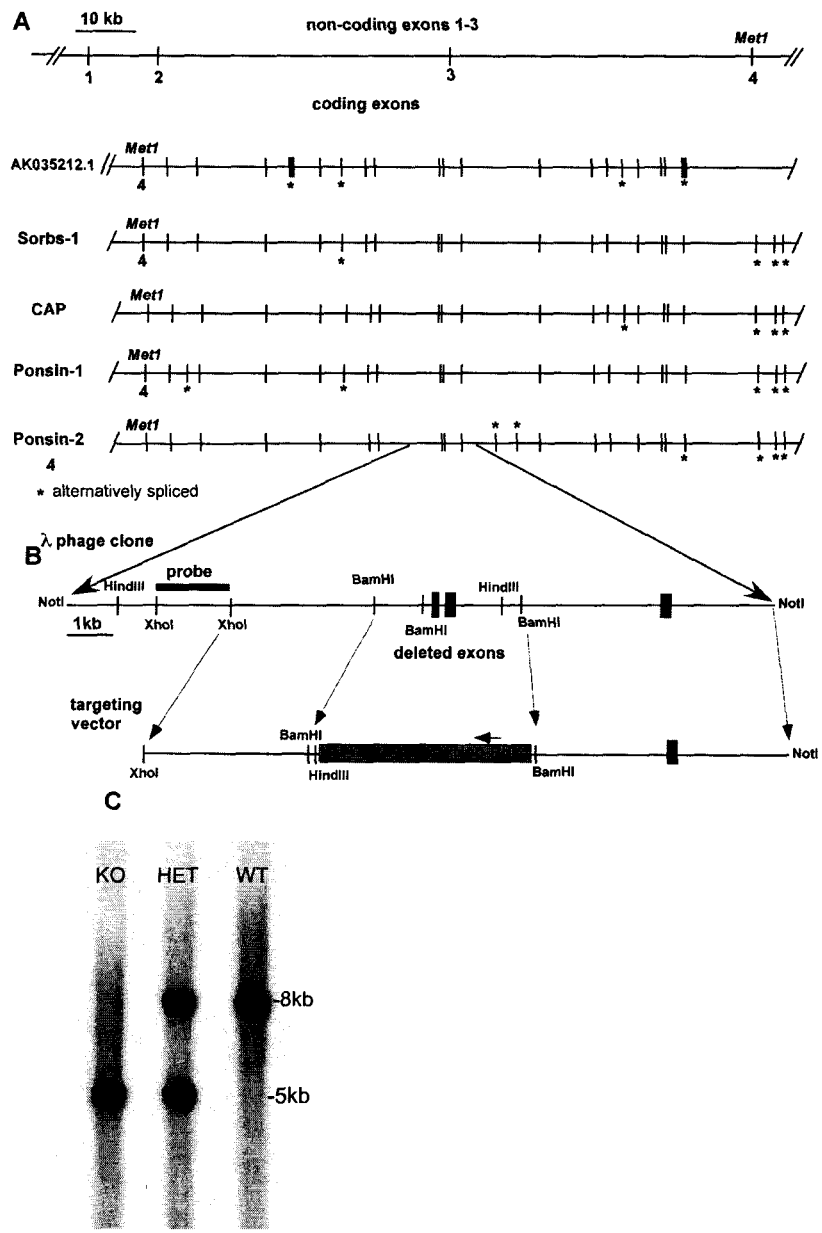
FIG. 1 demonstrates CAP deletion in CAPKO mice as a result of Ponsin knockout strategy.
Figure 2:
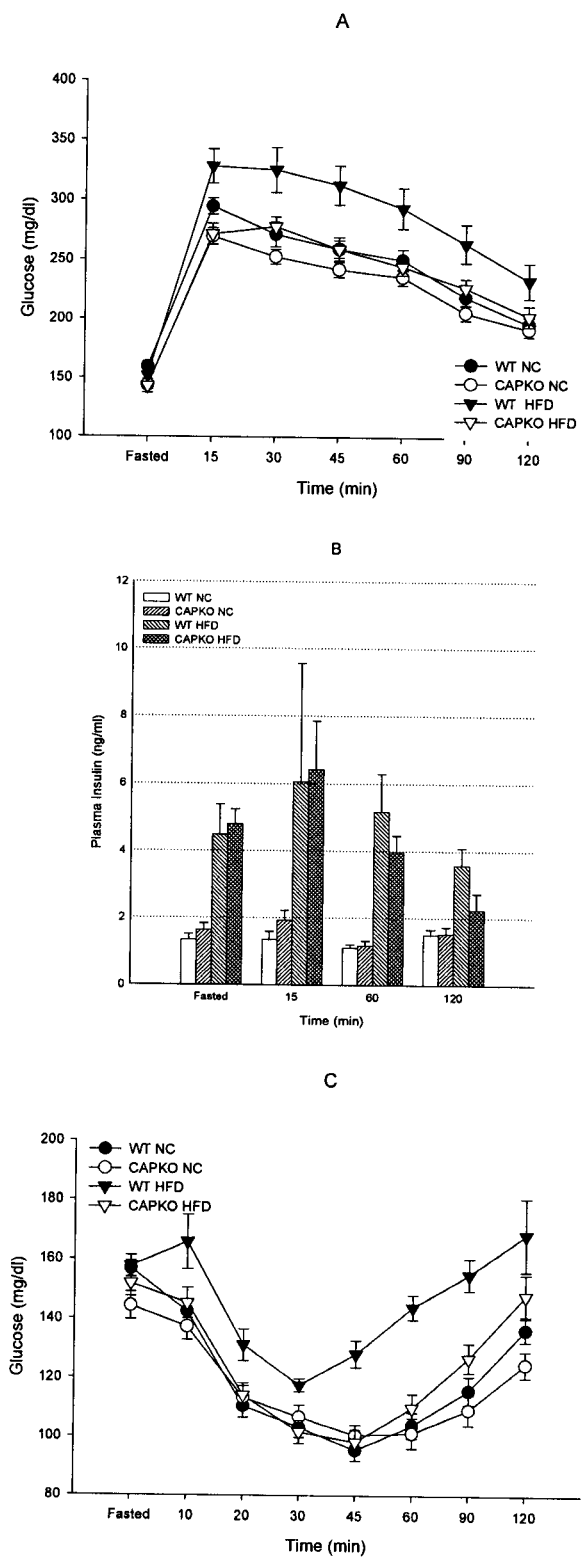
FIG. 2 is a series of line and scatter plots and box plots depicting results of glucose and insulin tolerance tests performed on whole body CAP knockout (CAPKO) and wild-type (WT) mice while maintained on a normal chow (NC) or high fat diet (HFD).
Figure 3:
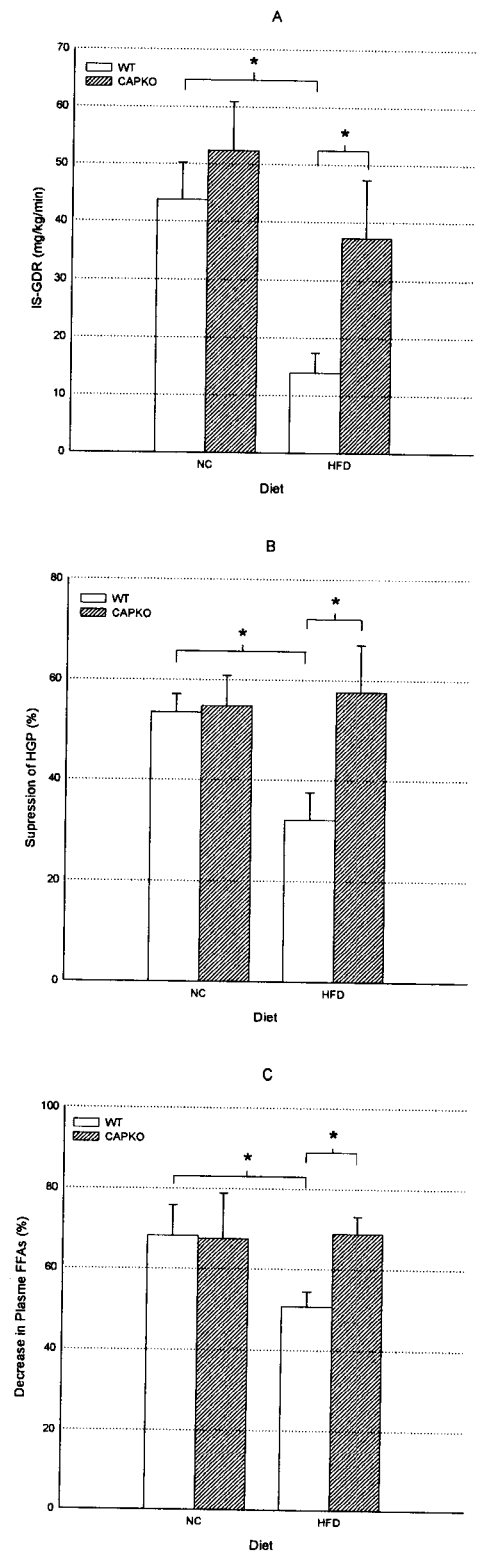
FIG. 3 is a series of box plots.
Figure 4A:
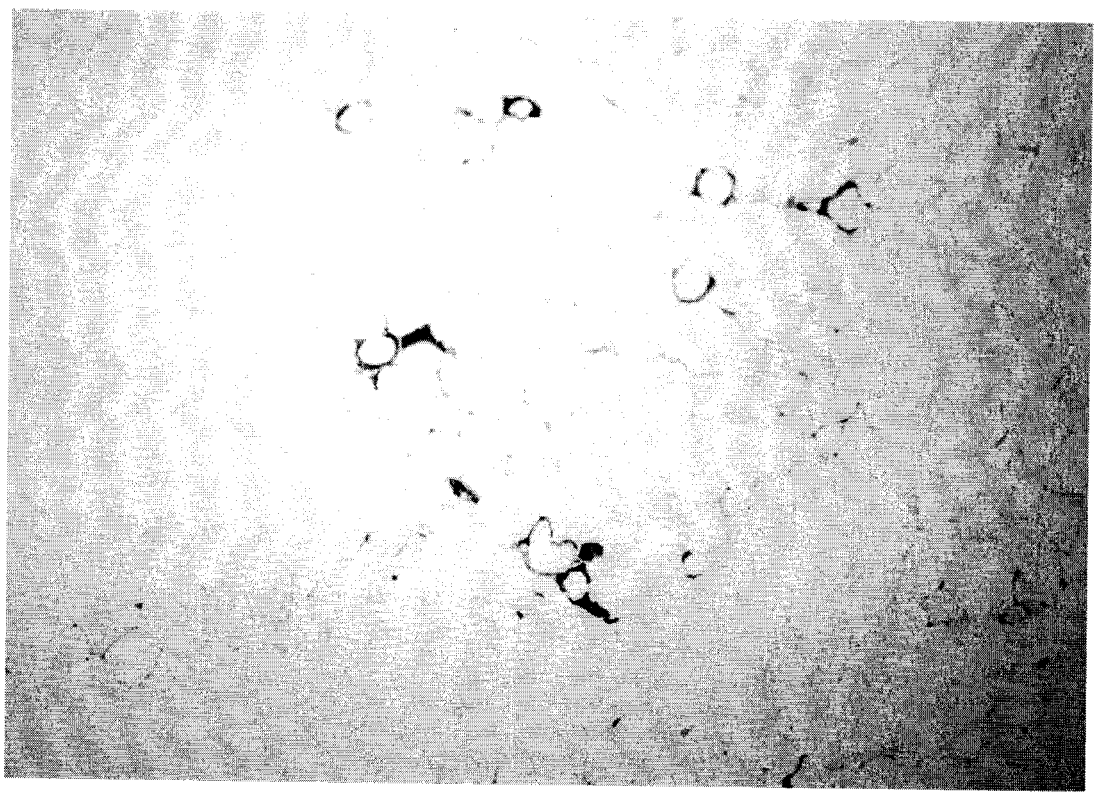
FIG. 4A shows hematoxylin stained adipose tissue from WT mice following high fat feeding. Heavy areas of staining indicate macrophage infiltration.
Figure 4B:
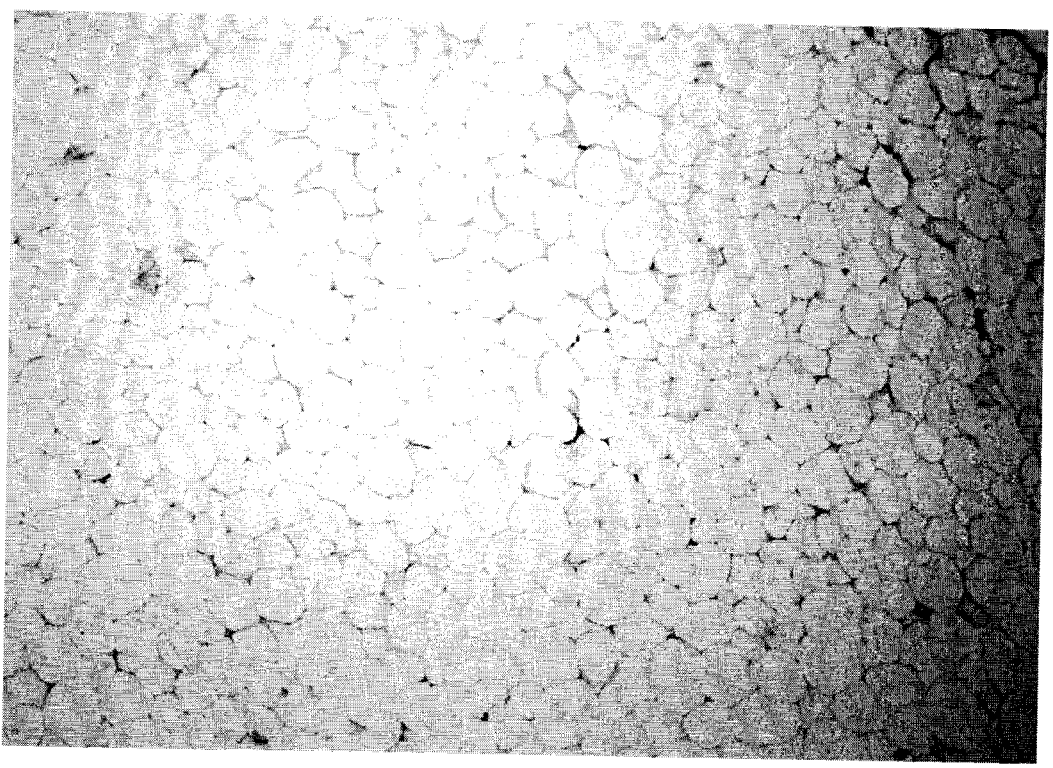
FIG. 4B shows hematoxylin stained adipose tissue from CAPKO mice following high fat feeding. F4/80+ staining in this image is greatly reduced. Thus, macrophage infiltration occurs in adipose tissue as a consequence of high fat feeding and is diminished in the CAPKO mice.
Figure 5A:
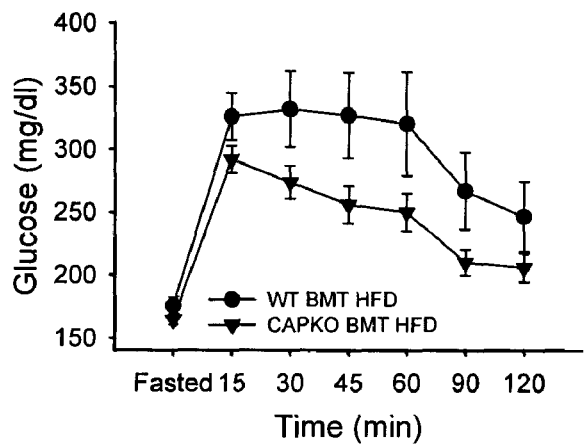
FIG. 5A depicts glucose concentration measured during a glucose tolerance test as a function of time for WT BMT HFD and CAPKO BMT HFD. Plasma insulin concentrations during the glucose tolerance test were also measured as a function of time for WT BMT HFD and CAPKO BMT HFD (not shown).
Figure 5B:
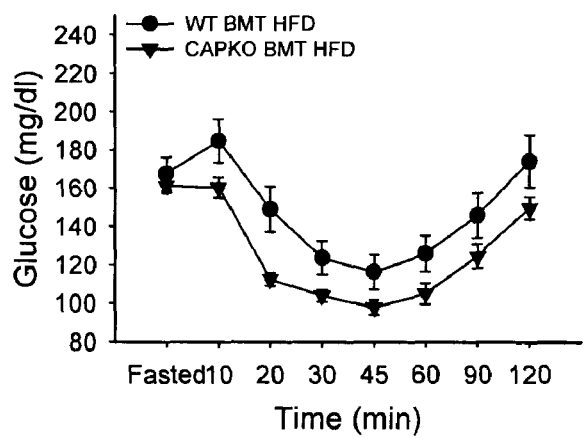
FIG. 5B depicts glucose concentration measured during the insulin tolerance test as a function of time for WT BMT HFD and CAPKO BMT HFD. These data indicate that CAP deletion in the marrow can be sufficient to confer protection from high fat diet induced insulin resistance.
Figure 5C:
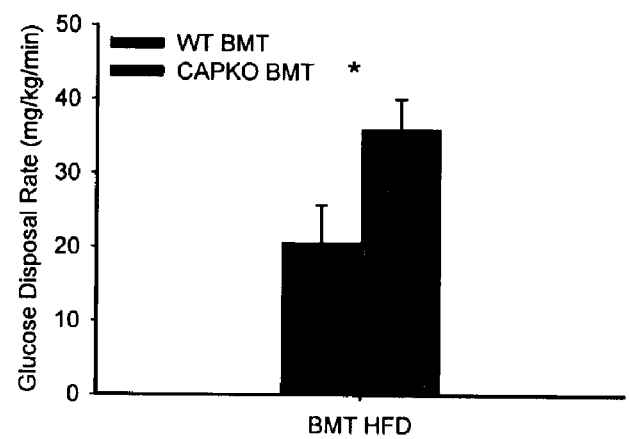
FIG. 5C depicts insulin-stimulated glucose disposal rate (in muscle) for WT BMT HFD and CAPKO BMT HFD. This demonstrates muscle specific protection against insulin resistance conferred by CAPKO bone marrow.
Figure 5D:
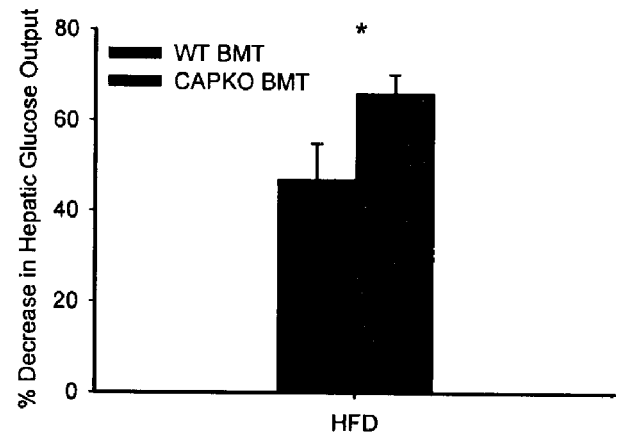
FIG. 5D depicts insulin-induced suppression of hepatic glucose output (in liver) for WT BMT HFD and CAPKO BMT HFD. This demonstrates liver specific protection against insulin resistance conferred by CAPKO bone marrow.
Figure 5E:
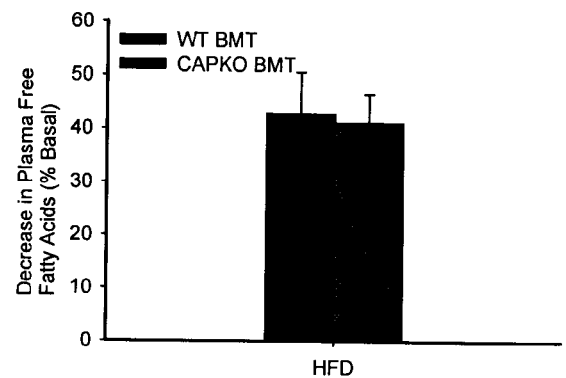
FIG. 5E depicts plasma free fatty acid levels. The data demonstrate insulin-induced suppression of plasma free fatty acids for WT BMT HFD and CAPKO BMT HFD.
Figure 6A:
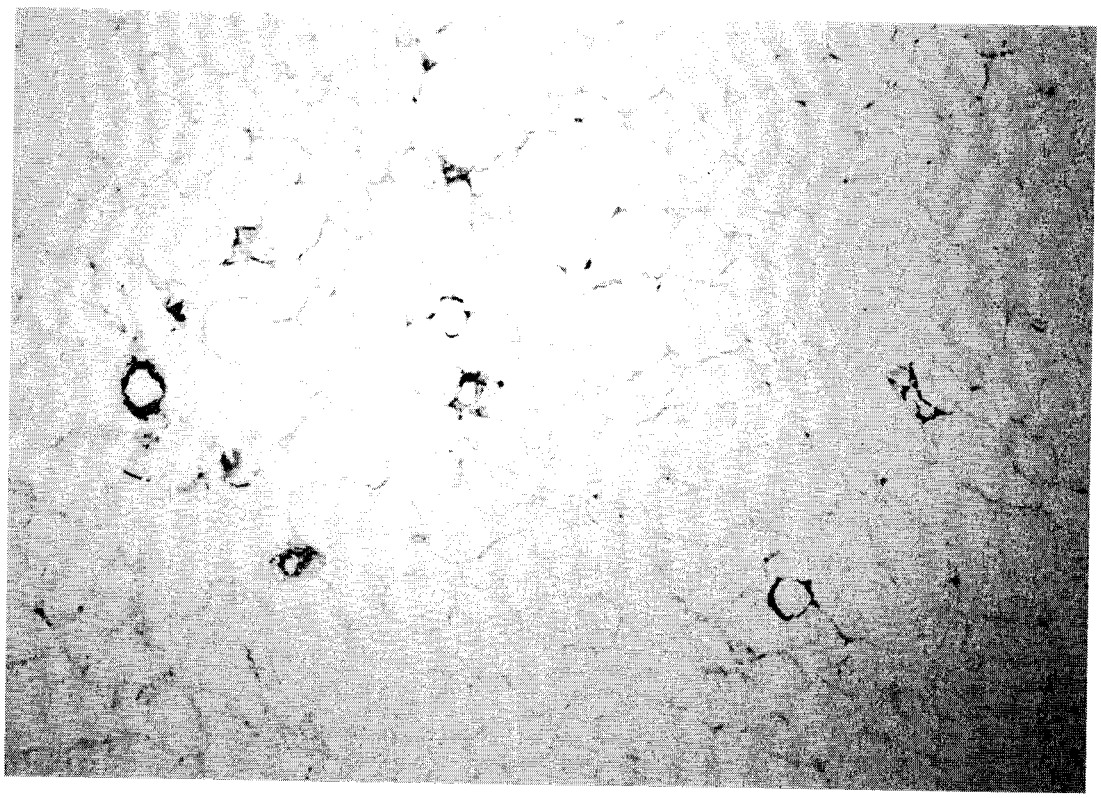
FIG. 6A shows stained adipose from mouse receiving WT marrow following 4-8 weeks high fat diet.
Figure 6B:
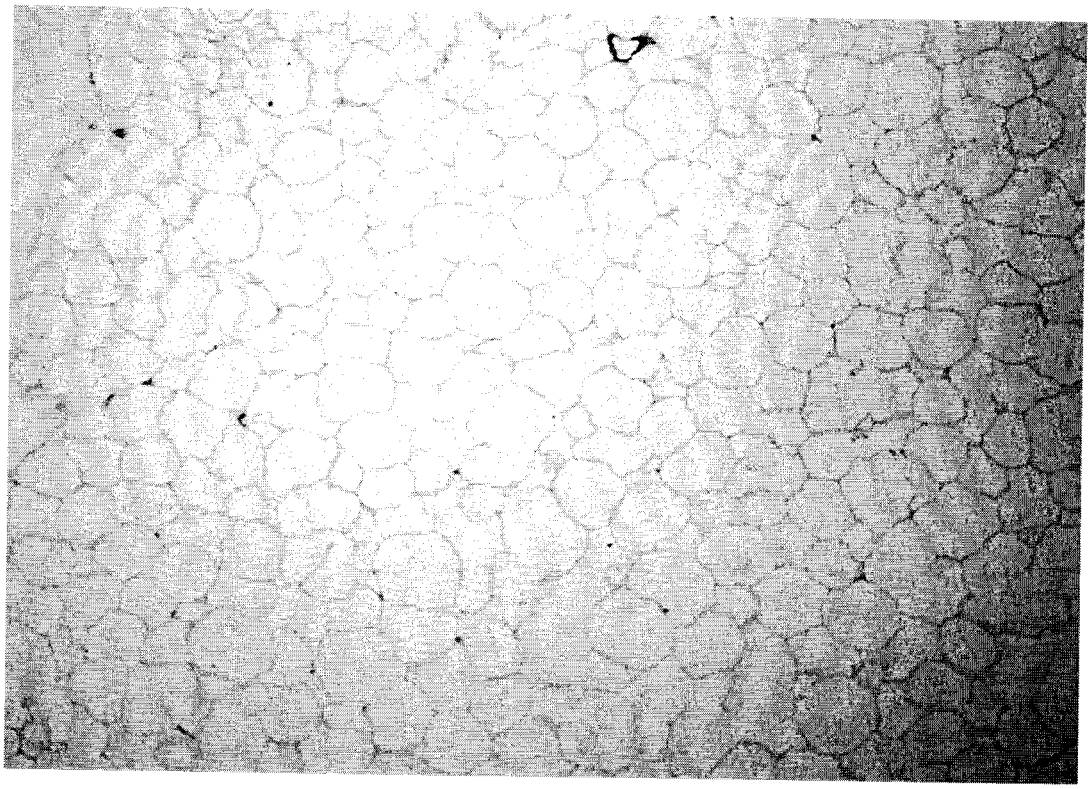
FIG. 6B shows stained adipose from mouse receiving CAPKO marrow following 4-8 weeks high fat diet. This demonstrates that macrophage function is altered in the bone marrow transplanted animals including histology for macrophage infiltration and macrophage activation and function.

The present inventors describe compounds and methods for pharmacological therapy for the treatment of insulin resistance and for treatment of type 2 diabetes in a subject in need thereof. The methods disclosed herein In some aspects of the present teachings, enhanced insulin action in target tissues can be accomplished through, inter alia, protection from high fat diet-induced whole body insulin resistance. Such protection can result from selective targeting of the CAP gene and/or expressed protein. In some aspects, compounds which inhibit CAP gene expression or CAP protein function can disrupt the inflammatory process associated with the metabolic syndrome, and enhance insulin action. This enhancement can occur without altering insulin secretion by the pancreas or inhibiting intestinal glucose absorption.

The methods described herein utilize laboratory techniques well known to skilled artisans, and guidance can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999; Nagy, A., et al., Manipulating the Mouse Embryo (Third Edition), Cold Spring Harbor Laboratory Press, Cold Spring Harbor, N.Y., 2003; Weir, D. M., ed., Handbook of Experimental Immunology. Vol 1: Immunochemistry, Blackwell Scientific Publications, Oxford, 1986; and textbooks such as Hedrickson et al., Organic Chemistry 3rd edition, McGraw Hill, New York, 1970.

For pharmaceuticals, conventional modes of administration can be employed. For example, administration can be carried out by oral, respiratory, or parenteral routes. Intradermal, subcutaneous, and intramuscular routes of administration can be used when a pharmaceutical formulation is administered parenterally. A therapeutic formulation can be prepared by mixing an active pharmaceutical ingredient with an excipient. Dosages and administration routes can be determined according to methods well-known in the art, for example, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

The present inventors have discovered that inhibition of CAP activity in macrophages, e.g., through disruption of the CAP gene can alter the inflammatory response and can also lead to improved insulin action in target tissues. Furthermore, the inventors have discovered that inhibition of CAP, e.g., through whole body CAP gene deletion or inactivation, can result in protection from high fat diet-induced insulin resistance that can be a consequence of altered insulin action in muscle, liver, and adipose, as well as in a reduction in the circulating inflammatory marker monocyte chemoattractant protein 1 (see e.g., Example 1). In some aspects, a tissue-specific gene deletion or disruption in macrophages can result in protection from high fat diet-induced whole body insulin resistance. In some configurations, this protection can result from improvements in insulin action in both the skeletal muscle and liver (see e.g., Example 2). Furthermore, in some aspects, this protection can be accomplished without limiting exercise capacity. In yet addition aspects, the inventors have discovered that transfer of CAP-inhibited bone marrow to normal hosts can confer protection from high fat diet-induced insulin resistance in the host. In these aspects, CAP-inhibited bone marrow can include genetic disruption of the CAP gene in the bone marrow cells, e.g., through genetic deletion.

In some aspects, the inventors demonstrate that CAP expression in macrophages is essential to the normal inflammatory response to high fat diet and the subsequent impairment in insulin action.

Thus, inhibition of CAP gene expression or protein activity, e.g, through CAP gene deletion or disruption in macrophages, can protect target tissues such as the muscle and liver from impaired insulin sensitivity.

Hence, the present teachings set forth in vitro cell cultures comprising macrophages having reduced CAP activity in comparison to macrophages comprised by a subject in need of treatment. These cell cultures can yield cells which can be used in methods for treating diseases or disorder involving insulin metabolism in a subject. In this regard, the methods can comprise a) providing an in vitro cell culture comprising macrophages having reduced CAP activity in comparison to macrophages comprised by a subject in need of treatment; and b) administering cells comprised by the in vitro cell culture to the subject. Providing such cell cultures can be accomplished by methods well known to skilled artisans, as set forth in standard laboratory manuals such as, for example, Spector, D. L. et al., Cells: A Laboratory Manual, Cold Spring Harbor Laboratory Press, Cold Spring Harbor, N.Y., 1998.

Hence, in certain configurations, providing a cell culture can comprise i. introducing a cell population comprising macrophages into the in vitro cell culture; and ii. inhibiting CAP gene expression in cells comprised by the in vitro cell culture. A cell population can be obtained, in non-limiting example, from bone marrow or other tissue comprising macrophages, such as, without limitation, peripheral blood. The cells can be grown in vitro by methods well known to skilled artisans. Furthermore, precursor cell populations can be used to establish cultures, e.g., stem cells such as, for example, embryonic, umbilical cord, bone marrow stem cells (such as mesenchymal stem cells) or haematopoietic stem cells. These cells can be grown in vitro and differentiated into macrophages using well-established methods known to skilled artisans, such as application of cytokines (e.g., Moore, M. A., et al., Methods in Enzymology 418: 208-242, 2006; Du, Y., et al., Blood 106: 3932-3939, 2005; Komor, M., et al., Stem Cells 23: 1154-1169, 2005; Zambidis, E. T., et al., Blood 106: 860-870, 2005; Wiles, M. V., Methods in Enzymology 225: 900-918, 2003).

In addition, in some configurations of these methods, inhibition of CAP gene expression in cells comprised by the culture, such as macrophages or precursors thereof, can be effected by disrupting or deleting the CAP gene comprised by the cells. The deletion or disruption can be effected by methods well known to skilled artisans, such as homologous recombination. In some configurations, the homologous recombination can introduce a selectable marker such as neomycin resistance, and recombinant cells can be selected by standard methods (e.g., by selecting for neomycin resistance).

Vectors needed for generating homologous recombinants are well known in the art, and in some configurations can include flanking markers that allow negative selection, such as, for example, hypoxanthine phosphoribosyl transferase, (HGPRT), to promote the probability of recovering homologous recombinants (Mansour, S., et al., Nature 336: 348-352, 1988; Thomas, K. R. and Capecchi, M. R., Cell 51: 503-512, 1987). Hence, in some configurations of these methods, homologous recombinants in which the CAP gene is disrupted can be obtained by transforming or transfecting cells with a nucleic acid comprising a copy of the CAP gene (or a portion thereof) which further comprises an insertion of a selectable marker which also disrupts CAP gene expression, and which can further comprise a flanking sequence encoding a negative selection marker. Cells can then be selected which express the positive selection marker (e.g., neomycin resistance) but do not express the negative selection marker (e.g., HGPRT). In addition, in some configurations, the homologous recombinants can be grown in vitro. In addition, if the cells so transformed are stem cells, they can be differentiated into macrophages by standard methods known to skilled artisans.

Hence, in some aspects of the present teachings, the homologous recombinant cells can be administered to a subject, such as a person in need of treatment. The administration can utilize standard methods known to skilled artisans, such as intravenous injection.

In some configurations, the subject recipient can be the donor of the cells (autologous transplantation), while in other configurations, the subject can be the recipient of syngeneic or allogeneic homologous transformants. It yet other configurations, the subject can be the recipient of xenogeneic homologous transformants.

In various aspects of the present teachings, inhibition of CAP activity through genetic disruption can utilize nucleic acids having sequences of the CAP gene or transcripts thereof. These sequences are well known in the art, and include, for example, the sequence indicated by the following GenBank accession numbers: AJ489942; NM_006434; NM_015385; NM_001034954; NM_001034955; NM_001034956; NM_024991; NM_001034957; AK022468; AF136380. These sequences correspond to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, and SEQ ID NO: 20. Amino acid sequences of polypeptides encoded by these nucleic acid sequences are set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and SEQ ID NO: 19, respectively. Furthermore, genomic sequences comprising mRNA sequences are well known in the art, and can be used to construct vectors for genetic knockouts. In various configurations, CAP antagonists specifically recognize homologs of the CAP gene and/or the CAP protein.

In one embodiment, an isolated nucleic acid molecule that can be used in the invention comprises a nucleic acid molecule that is a complement of any of the nucleotide sequences referenced above, or a portion of one of the nucleotide sequences (e.g., a fragment that can be used as a probe or primer or a fragment encoding a biologically-active portion of firbrinogen). A nucleic acid molecule that is complementary to the nucleotide sequence is one that is sufficiently complementary to the nucleotide sequence that it can hydrogen bond with little or no mismatches to the nucleotide sequence, thereby forming a stable duplex.

A "homologous nucleic acid sequence" or "homologous amino acid sequence," or variations thereof, refer to sequences characterized by a homology at the nucleotide level or amino acid level as discussed above. In the present teachings, homologous nucleotide sequences include nucleotide sequences encoding CAP for a species other than humans, including, but not limited to, various vertebrates, such as frog, mouse, rat, rabbit, dog, cat, cow, and horse. Homologous nucleotide sequences also include, but are not limited to, naturally occurring allelic variations. Homologous nucleic acid sequences include those nucleic acid sequences that encode conservative amino acid substitutions, as well as a polypeptide possessing biological activity.

A biologically active portion of CAP can have an amino acid sequence as disclosed herein, or a sequence having substantial sequence identity with a CAP sequence disclosed herein, and retain CAP functional activity, yet differ in amino acid sequence due to natural allelic variation or mutagenesis. A biologically active CAP polypeptide can comprise an amino acid sequence at least about 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence disclosed herein and retain the functional activity.

CAP Antibody

Certain embodiments comprise immunopeptides directed against CAP protein. The immunoglobulin peptides, or antibodies, useful to the invention bind to the CAP protein. Such CAP binding activity is specific and not substantially blocked by non-specific reagents. These CAP specific antibodies can be used in immunotherapy against insulin resistance or type II diabetes to selectively target CAP protein as a means of disrupting the normal inflammatory process associated with these disorders and thereby improve insulin action.

In certain therapeutic embodiments, the selected antibody will typically be an anti-CAP antibody, which may be administered alone, or in combination with, or conjugated to, one or more combinatorial therapeutic agents. When the antibodies described herein are administered alone as therapeutic agents, they may exert a beneficial effect in the subject by a variety of mechanisms. In certain embodiments, monoclonal antibodies that specifically bind CAP are purified and administered to a patient to neutralize one or more forms of CAP, to block one or more activities of CAP, or to block or inhibit an interaction of one or more forms of CAP with another biomolecule.

The immunotherapeutic reagents of the invention may include humanized antibodies, and can be combined for therapeutic use with additional active or inert ingredients, e.g., in conventional pharmaceutically acceptable carriers or diluents, e.g., immunogenic adjuvants, and optionally with adjunctive or combinatorially active agents such as anti-inflammatory and/or anti-fibrinolytic drugs.

In other embodiments, therapeutic antibodies described herein can be coordinately administered with, co-formulated with, or coupled to (e.g., covalently bonded) a combinatorial therapeutic agent, for example a radionuclide, a differentiation inducer, a drug, or a toxin. Various known radionuclides can be employed, including 90Y, 123I, 125I, 131I, 186Re, 188Re, and 211At. Useful drugs for use in such combinatorial treatment formulations and methods include methotrexate, and pyrimidine and purine analogs. Suitable differentiation inducers include phorbol esters and butyric acid. Suitable toxins include ricin, abrin, diptheria toxin, cholera toxin, gelonin, *Pseudomonas exotoxin, Shigella* toxin, and pokeweed antiviral protein. These combinatorial therapeutic agents can be coupled to an anti-CAP antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. Alternatively, it may be desirable to couple a combinatorial therapeutic agent and an antibody via a linker group as a spacer to distance an antibody from the combinatorial therapeutic agent in order to avoid interference with binding capabilities. A linker group can also serve to increase the chemical reactivity of a substituent on an agent or an antibody, and thus increase the coupling efficiency. It will be further evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be affected, for example, through amino groups, carboxyl groups, sulfhydryl groups or oxidized carbohydrate residues.

If a therapeutic agent is more potent when free from the antibody portion of the immunoconjugates described herein, a linker group which is cleavable during or upon internalization into a cell can be used. A number of different cleavable linker groups have been described (e.g., U.S. Pat. No. 4,489,710, to Spitler; U.S. Pat. No. 4,638,045, to Kohn et al.; U.S. Pat. No. 4,671,958, to Rodwell et al.; U.S. Pat. No. 4,569,789, to Blattler et al.) In some configurations, more than one agent can be coupled to an anti-CAP antibody. In one embodiment, multiple molecules of an agent can be coupled to one antibody molecule. In another configuration, more than one type of agent may be coupled to one antibody.

In some aspects, immunopeptides can be raised in a variety of means known to the art. As used herein, the term antibody encompasses all types of antibodies, e.g., polyclonal, monoclonal, and those produced by the phage display methodology. In certain embodiments, the antibodies can exhibit an affinity for CAP of about $Kd<10^{-8}$ M.

Immunoglobulin peptides include, for example, polyclonal antibodies, monoclonal antibodies, and antibody fragments. A variety of routes of administration for the antibodies and immunoconjugates can be used. Typically, administration is intravenous, intramuscular, or subcutaneous.

It will be evident that the precise dose of the antibody will vary depending upon such factors as the antibody used, the antigen density, and the rate of clearance of the antibody. A safe and effective amount of an anti-CAP agent is, for example, that amount that would have a therapeutic effect in a patient while minimizing side effects. Generally, a therapeutically effective amount is an amount sufficient to mitigate the inflammatory response associated with impaired insulin action and ultimately result in improved insulin action in target tissues. The dosage regimen can be determined by a skilled clinician, based on factors, such as the exact nature of the condition being treated, the severity of the condition, the age of the patient, and general physical condition of the patient.

Polyclonal Antibodies

Polyclonal antibodies may be readily generated by one of ordinary skill in the art from a variety of warm-blooded animals such as horses, cows, various fowl, rabbits, mice, or rats. Briefly, CAP antigen is utilized to immunize the animal through intraperitoneal, intramuscular, intraocular, or subcutaneous injections, with an adjuvant such as Freund's complete or incomplete adjuvant. Following several booster immunizations, samples of serum are collected and tested for reactivity to CAP.

Monoclonal Antibodies

Monoclonal antibody (MAb) technology can be used to obtain MAbs to CAP. Briefly, hybridomas can be produced using spleen cells from mice immunized with CAP antigens. The spleen cells of each immunized mouse are fused with mouse myeloma Sp 2/0 cells, for example using the polyethylene glycol fusion method of Galfre, G. and Milstein, C., Methods Enzymol., 73:3-46 (1981). Growth of hybridomas, selection in HAT medium, cloning and screening of clones against antigens are carried out using standard methodology (Galfre, G. and Milstein, C., Methods Enzymol., 73:3-46 (1981)).

HAT-selected clones can be injected into mice to produce large quantities of MAb in ascites tumors as described by Galfre, G. and Milstein, C., Methods Enzymol., 73:3-46 (1981). Immunoglobulin comprised by an ascites fluid can be purified using protein A column chromatography (BioRad, Hercules, Calif.).

MAbs can be screened or tested for CAP specificity using any of a variety of standard techniques, including Western Blotting (Koren, E. et al., Biochim. Biophys. Acta 876:91-100 (1986)) and enzyme-linked immunosorbent assay (ELISA) (Koren, E. et al., Biochim. Biophys. Acta 876:91-100 (1986)).

Humanized Antibodies

Humanized forms of mouse antibodies can be generated by linking the CDR regions of non-human antibodies to human constant regions by recombinant DNA techniques (see, e.g., Queen et al., Proc. Natl. Acad. Sci. USA 86:10029-10033, 1989 and WO 90/07861, each incorporated by reference). Human antibodies can be obtained using phage-display methods (see, e.g., Dower et al., WO 91/17271; McCafferty et al., WO 92/01047). In these methods, libraries of phage are produced in which members display different antibodies on their outersurfaces. Antibodies can be displayed as Fv or Fab fragments. Phage displaying antibodies can be screened and selected by affinity enrichment. Human antibodies can be identified using standard seletion methods such as, for example, competitive binding assays.

Antibody Fragments

Some aspects of the present teachings include functional fragments of a MAb of CAP. Fab and F(ab')2 fragments of MAbs that bind CAP can be used in place of whole MAbs.

Recombinant DNA methods have been developed which permit the production and selection of recombinant immunoglobulin peptides which are single chain antigen-binding polypeptides known as single chain Fv fragments (ScFvs or ScFv antibodies). Further, ScFvs can be dimerized to produce a diabody. ScFvs bind a specific epitope of interest and can be produced using any of a variety of recombinant bacterial phage-based methods, for example as described in Lowman et al. (1991) Biochemistry, 30, 10832-10838; Clackson et al. (1991) Nature 352, 624-628; and Cwirla et al. (1990) Proc. Natl. Acad. Sci. USA 87, 6378-6382. These methods are usually based on producing genetically altered filamentous phage, such as recombinant M13 or fd phages, which display on the surface of the phage particle a recombinant fusion protein containing the antigen-binding ScFv antibody as the amino terminal region of the fusion protein and the minor phage coat protein g3p as the carboxy terminal region of the fusion protein. Such recombinant phages can be readily grown and isolated using well-known methods. Furthermore, the intact phage particles can usually be screened directly for the presence (display) of an antigen-binding ScFv on their surface without the necessity of isolating the ScFv away from the phage particle.

To produce an ScFv, standard reverse transcriptase protocols are used to first produce cDNA from mRNA isolated from a hybridoma that produces an MAb for CAP antigen. The cDNA molecules encoding the variable regions of the heavy and light chains of the MAb can then be amplified by standard polymerase chain reaction (PCR) methodology using a set of primers for mouse immunoglobulin heavy and light variable regions (Clackson (1991) Nature 352, 624-628). The amplified cDNAs encoding MAb heavy and light chain variable regions are then linked together with a linker oligonucleotide in order to generate a recombinant ScFv DNA molecule. The ScFv DNA is ligated into a filamentous phage plasmid designed to fuse the amplified cDNA sequences into the 5' region of the phage gene encoding the minor coat protein called g3p. *Escherichia coli* bacterial cells are than transformed with the recombinant phage plasmids, and filamentous phage grown and harvested. The desired recombinant phages display antigen-binding domains fused to the amino terminal region of the minor coat protein. Such "display phages" can then be passed over immobilized antigen, for example, using the method known as "panning", see Parmley and Smith (1989) Adv. Exp. Med. Biol. 251, 215-218; Cwirla et al. (1990) Proc. Natl. Acad. Sci. USA 87, 6378-6382, to adsorb those phage particles containing ScFv antibody proteins that are capable of binding antigen. The antigen-binding phage particles can then be amplified by standard phage infection methods, and the amplified recombinant phage population again selected for antigen-binding ability. Such successive rounds of selection for antigen-binding ability, followed by amplification, select for enhanced antigen-binding ability in the ScFvs displayed on recombinant phages. Selection for increased antigen-binding ability may be made by adjusting the conditions under which binding takes place to require a tighter binding activity. Another method to select for enhanced antigen-binding activity is to alter nucleotide sequences within the cDNA encoding the binding domain of the ScFv and subject recombinant phage populations to successive rounds of selection for antigen-binding activity and amplification (see Lowman et al. (1991) Biochemistry 30, 10832-10838; and Cwirla et al. (1990) Proc. Natl. Acad. Sci. USA 87, 6378-6382).

Once an ScFv is selected, the recombinant CAP antibody can be produced in a free form using an appropriate vector grown in a suitable host bacteria such as *E. coli* strain HB2151. These bacteria secrete ScFv in a soluble form, free of phage components (Hoogenboom et al. (1991) Nucl. Acids Res. 19, 4133-4137). The purification of soluble ScFv from the HB2151 bacteria culture medium can be accomplished by affinity chromatography using antigen molecules immobilized on a solid support such as AFFIGEL™ (BioRad, Hercules, Calif.).

Other developments in the recombinant antibody technology demonstrate possibilities for further improvements such as increased avidity of binding by polymerization of ScFvs into dimers and tetramers (see Holliger et al. (1993) Proc. Natl. Acad. Sci. USA 90, 6444-6448).

Because ScFvs are even smaller molecules than Fab or F(ab')2 fragments, they can be used to attain even higher densities of antigen binding sites per unit of surface area when immobilized on a solid support material than possible using whole antibodies, F(ab')2, or Fab fragments. Furthermore, recombinant antibody technology offers a more stable genetic source of antibodies, as compared with hybridomas. Recombinant antibodies can also be produced more quickly and economically using standard bacterial phage production methods.

Recombinant Antibody Production

To produce antibodies described herein recombinantly, nucleic acids encoding light and heavy chain variable regions, optionally linked to constant regions, are inserted into expression vectors. The light and heavy chains can be cloned in the same or different expression vectors. The DNA segments encoding antibody chains are operably linked to control sequences in the expression vector(s) that ensure the expression of antibody chains. Such control sequences include a signal sequence, a promoter, an enhancer, and a transcription termination sequence. Expression vectors are typically replicable in the host organisms either as episomes or as an integral part of the host chromosome. *E. coli* is one procaryotic host particularly useful for expressing antibodies of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda. Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired. Mammalian tissue cell culture can also be used to express and produce the antibodies of the present invention (see, e.g., Winnacker, From Genes to Clones VCH Publishers, N.Y., 1987). Examples of host cells for expressing nucleic acids encoding the immunoglobulins of the present teachings include: monkey kidney CV1 line transformed by SV40 (COS-7, ATCC CRL 1651); human embryonic kidney line; baby hamster kidney cells (BHK, ATCC CCL 10); Chinese hamster ovary-cells (CHO); mouse sertoli cells; monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and TRI cells.

The vectors containing the polynucleotide sequences of interest (e.g., the heavy and light chain encoding sequences and expression control sequences) can be transferred into a host cell using standard transfection methods (Sambrook et al., Molecular Cloning: A Laboratory Manual, Cold Spring Harbor Press, 2rd ed., 2001). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i.e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, e.g., Scopes, Protein Purification, Springer-Verlag, N.Y., 1982). Substantially pure immunoglobulins of at least about 90 to 95% homogeneity are preferred, and 98 to 99% or more homogeneity most preferred.

siRNA

In certain therapeutic embodiments, the CAP antagonist is siRNA. The levels of CAP can be down-regulated by RNA interference by administering to the patient a therapeutically effective amount of small interfering RNAs (siRNA) specific for CAP. siRNA specific for CAP can be produced commercially from a variety of sources, such as Ambion (Austin, Tex.). The siRNA can be administered to the subject by any means suitable for delivering the siRNA to the blood. For example, the siRNA can be administered by gene gun, electroporation, or by other suitable parenteral or enteral administration routes, such as intravitreous injection.

RNA interference is the process by which double stranded RNA (dsRNA) specifically suppresses the expression of a gene bearing its complementary sequence. Suppression of the CAP gene inhibits the production of the CAP protein. In some configurations, an siRNA can comprise a short double-stranded RNA from about 17 nucleotides to about 29 nucleotides in length, preferably from about 19 to about 25 nucleotides in length, that are targeted to the target mRNA.

As an example, an effective amount of the siRNA can be an amount sufficient to cause RNAi-mediated degradation of the target CAP mRNA, or an amount sufficient to disrupting the normal inflammatory process associated with impaired insulin action and improve insulin action. One skilled in the art can readily determine an effective amount of the siRNA of the invention to be administered to a given subject by taking into account factors such as the size and weight of the subject; the extent of insulin resistance; the age, health and sex of the subject; the route of administration; and whether the administration is regional or systemic. Generally, an effective amount of siRNA comprises an intercellular concentration of from about 1 nanomolar (nM) to about 100 nM, preferably from about 2 nM to about 50 nM, more preferably from about 2.5 nM to about 10 nM. It is contemplated that greater or lesser amounts of siRNA can be administered.

The siRNA can be targeted to any stretch of approximately 19-25 contiguous nucleotides in any of the CAP mRNA target sequences. Target sequences can be selected from, for example, a sequence of CAP, as set forth in the sequence listings herein. Searches of the human genome database (BLAST) can be carried out to ensure that selected siRNA sequence will not target other gene transcripts. Techniques for selecting target sequences for siRNA are given, for example, in Elbashir et al. ((2001) Nature 411, 494-498). Thus, the sense strand of the present siRNA comprises a nucleotide sequence identical to any contiguous stretch of about 19 to about 25 nucleotides in the target mRNA of CAP. Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon.

Antisense

In certain therapeutic embodiments, the CAP antagonist is an antisense oligonucelotide. The levels of CAP can be down-regulated by administering to the patient a therapeutically effective amount of an antisense oligonucleotide specific for CAP mRNA. The antisense oligonucleotide specific for CAP mRNA may span the region adjacent to the initiation site of CAP translation.

An effective amount of the antisense oligonucleotide specific for CAP mRNA as isolated in a purified form may is generally that amount capable of inhibiting the production of CAP or reducing the amount produced or the rate of production of CAP such that the normal inflammatory process associated with impaired insulin action is disrupted and/or insulin action is improved. Antisense oligonucleotides can be administered via intravitreous injection at a concentration of about 10 µg/day to about 3 mg/day. For example, administered dosage can be about 30 µg/day to about 300 µg/day. As another example, CAP antisense oligonucleotide can be administered at about 100 µg/day. Administration of antisense oligonucleotides can occur as a single event or over a time course of treatment. For example, IL-10 antisense oligonucleotides can be injected daily, weekly, bi-weekly, or monthly. Time course of treatment can be from about a week to about a year or more. In one example, CAP antisense oligonucleotides are injected daily for one month. In another example, antisense oligonucleotides are injected weekly for about 10 weeks. In a further example, CAP antisense oligonucleotides are injected every 6 weeks for 48 weeks.

Dosage

It is within the ordinary skill in the art to formulate a range of dosages for use in humans and other mammals. A "therapeutically effective amount" generally refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition.

Toxicity and therapeutic efficacy of such compounds can be determined by standard pharmaceutical procedures in cell cultures or experimental animals for determining the LD50 (the dose lethal to 50% of the population) and the ED50, (the dose therapeutically effective in 50% of the population). The dose ratio between toxic and therapeutic effects is the therapeutic index that can be expressed as the ratio LD50/ED50. Compounds that exhibit large therapeutic indices are preferred. While compounds exhibiting toxic side effects may be used, care should be taken to design a delivery system that targets such compounds to the site affected by the disease or disorder in order to minimize potential damage to unaffected cells and reduce side effects.

The dosage of such compounds lies preferably within a range of circulating plasma or other bodily fluid concentrations that include the ED50 with little or no toxicity. The dosage may vary within this range depending upon the dosage form employed and the route of administration utilized. For any compound of the invention, the therapeutically effective dose can be estimated initially from cell culture assays. A dosage may be formulated in animal models to achieve a circulating plasma concentration range that includes the IC50 (the concentration of the test compound that achieves a half-maximal inhibition of symptoms) as determined in cell culture. Such information can be used to more accurately determine useful dosages in humans and other mammals. Compound levels in plasma may be measured, for example, by high performance liquid chromatography.

The amount of a compound that may be combined with a pharmaceutically acceptable carrier to produce a single dosage form will vary depending upon the host treated and the particular mode of administration. It will be appreciated by those skilled in the art that the unit content of a compound contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage regime for treating a disease or condition with the compounds of the invention is selected in accordance with a variety of factors, including the type, age, weight, sex, diet and medical condition of the patient, the route of administration, pharmacological considerations such as activity, efficacy, pharmacokinetic and toxicology profiles of the particular compound employed, whether a compound delivery system is utilized and whether the compound is administered as a pro-drug or part of a drug combination. Thus, the dosage regime actually employed may vary widely from subject to subject.

Formulations

The compounds/polypeptides of the present invention may be formulated by known methods for administration to a subject using several routes which include, but are not limited to, parenteral, oral, topical, intradermal, intramuscular, intraperitoneal, intravenous, subcutaneous, intranasal, epidural, intercranial, and ophthalmic routes. The individual compounds may also be administered in combination with one or more additional compounds of the present invention and/or together with other biologically active or biologically inert agents. Such biologically active or inert agents may be in fluid or mechanical communication with the compound(s) or attached to the compound(s) by ionic, covalent, Van der Waals, hydrophobic, hydrophillic or other physical forces. It is preferred that administration is localized in a subject, but administration may also be systemic.

The compounds of the present invention may be formulated by any conventional manner using one or more pharmaceutically acceptable agents (e.g., carriers and/or excipients). Thus, the compounds and their pharmaceutically acceptable salts and solvates may be specifically formulated for administration, e.g., by inhalation or insufflation (either through the mouth or the nose) or oral, buccal, parenteral or rectal administration. The compounds may take the form of charged, neutral and/or other pharmaceutically acceptable salt forms. Examples of pharmaceutically acceptable carriers include, but are not limited to, those described in Remington the Science and Practice of Pharmacy (University of the Sciences in Philadelphia, Ed.) 21st edition, Lippincott Williams & Wilkins PA, USA (2005).

A "pharmaceutically acceptable carrier" is generally a diluent, adjuvant, excipient, or vehicle with which a compound is administered. Such carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when a compound is administered intravenously. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. A compound, if desired, can also combine minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compounds in combination with carriers are known to those of skill in the art.

A "pharmaceutically acceptable salt" generally includes those salts of a pharmaceutically acceptable compound formed with free amino groups such as those derived from hydrochloric, phosphoric, acetic, oxalic, tartaric acids, and those formed with free carboxyl groups such as those derived from sodium, potassium, ammonium, calcium, ferric hydroxides, isopropylamine, triethylamine, 2-ethylamino ethanol, histidine, and procaine. If the compound is basic, salts may be prepared from pharmaceutically acceptable non-toxic acids including inorganic and organic acids. Such acids include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids. If the compound is acidic, salts may be prepared from pharmaceutically acceptable organic and inorganic bases. Suitable organic bases include, but are not limited to, lysine, N,N'-dibenzylethylenediamine, chloroprocaine, choline, diethanolamine, ethylenediamine, meglumine (N-methylglucamine) and procaine. Suitable inorganic bases include, but are not limited to, alkaline and earth-alkaline metals such as aluminum, calcium, lithium, magnesium, potassium, sodium and zinc. Methods for synthesizing such salts are known to those of skill in the art.

The compounds described herein can be administered as a pro-drug. A "pro-drug" generally refers to any compound which releases an active drug in vivo when such a compound is administered to a mammalian subject. Pro-drugs can be prepared, for example, by functional group modification of an active drug. The functional group may be cleaved in vivo to release the active drug compound. Pro-drugs include, for example, compounds in which a group that may be cleaved in vivo is attached to a hydroxy, amino or carboxyl group in the active drug. Examples of pro-drugs include, but are not limited to esters (e.g., acetate, methyl, ethyl, formate, and benzoate derivatives), carbamates, amides and ethers. Methods for synthesizing such pro-drugs are known to those of skill in the art.

The compounds may also take the form of solutions, suspensions, emulsions, tablets, pills, capsules, powders, controlled- or sustained-release formulations and the like. Such formulations will contain a therapeutically effective amount of the compound, preferably in purified form, together with a suitable amount of carrier so as to provide the form for proper administration to the patient. The formulation should suit the mode of administration.

The compound may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes or multiple dose vials made of glass, plastic or the like. The formulation may take such forms as suspensions, solutions or emulsions in oily or aqueous vehicles, and may contain formulatory agents such as suspending, stabilizing and/or dispersing agents.

For example, a parenteral preparation may be a sterile injectable solution or suspension in a nontoxic parenterally acceptable diluent or solvent (e.g., as a solution in 1,3-butanediol). Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the parenteral preparation.

Alternatively, the compound may be formulated in powder form for constitution with a suitable vehicle, such as sterile pyrogen-free water, before use. For example, a compound suitable for parenteral administration may comprise a sterile isotonic saline solution containing between 0.1 percent and 90 percent weight per volume of the compound. By way of example, a solution may contain from about 0.1 percent to about 20 percent, more preferably from about 0.55 percent to about 17 percent, more preferably from about 0.8 to about 14 percent, and still more preferably about 10 percent of the compound. The solution or powder preparation may also include a solubilizing agent and a local anesthetic such as lignocaine to ease pain at the site of the injection. Other methods of parenteral delivery of compounds will be known to the skilled artisan and are within the scope of the invention.

For oral administration, the compound may take the form of tablets or capsules prepared by conventional means with pharmaceutically acceptable excipients such as binding agents, fillers, lubricants and disintegrants:

The tablets or capsules may optionally be coated by methods well known in the art. If binders and/or fillers are used with the compounds of the invention, they are typically formulated as about 50 to about 99 weight percent of the compound. In one aspect, about 0.5 to about 15 weight percent of disintegrant, and particularly about 1 to about 5 weight percent of disintegrant, may be used in combination with the compound. A lubricant may optionally be added, typically in an amount of less than about 1 weight percent of the compound. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other less typical formulations are known in the art.

Liquid preparations for oral administration may take the form of solutions, syrups or suspensions. Alternatively, the liquid preparations may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations may also contain buffer salts, flavoring, coloring, perfuming and sweetening agents as appropriate. Preparations for oral administration may also be formulated to achieve controlled release of the compound. Oral formulations preferably contain 10% to 95% compound. In addition, the compounds of the present invention may be formulated for buccal administration in the form of tablets or lozenges formulated in a conventional manner. Other methods of oral delivery of compounds will be known to the skilled artisan and are within the scope of the invention.

Controlled-release (or sustained-release) preparations may be formulated to extend the activity of the compound and reduce dosage frequency. Controlled-release preparations can also be used to effect the time of onset of action or other characteristics, such as blood levels of the compound, and consequently affect the occurrence of side effects.

Controlled-release preparations may be designed to initially release an amount of a compound that produces the desired therapeutic effect, and gradually and continually release other amounts of the compound to maintain the level of therapeutic effect over an extended period of time. In order to maintain a near-constant level of a compound in the body, the compound can be released from the dosage form at a rate that will replace the amount of compound being metabolized and/or excreted from the body. The controlled-release of a compound may be stimulated by various inducers, e.g., change in pH, change in temperature, enzymes, water, or other physiological conditions or molecules.

Controlled-release systems may include, for example, an infusion pump which may be used to administer the compound in a manner similar to that used for delivering insulin or chemotherapy to specific organs or tumors. Typically, using such a system, the compound is administered in combination with a biodegradable, biocompatible polymeric implant that releases the compound over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

The compounds of the invention may be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds will be known to the skilled artisan and are within the scope of the invention.

The compound may also be formulated as a depot preparation. Such long-acting formulations may be administered by implantation (e.g., subcutaneously or intramuscularly or intercranially) or by injection. Accordingly, the compounds may be formulated with suitable polymeric or hydrophobic materials such as an emulsion in an acceptable oil or ion exchange resins, or as sparingly soluble derivatives such as a sparingly soluble salt. Other methods of depot delivery of compounds will be known to the skilled artisan and are within the scope of the invention.

Various other delivery systems are known in the art and can be used to administer the compounds of the invention. Moreover, these and other delivery systems may be combined and/or modified to optimize the administration of the compounds of the present invention. Exemplary formulations using the compounds of the present invention are described below (the compounds of the present invention are indicated as the active ingredient, but those of skill in the art will recognize that pro-drugs and compound combinations are also meant to be encompassed by this term):

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention. The examples use the following materials and methods.

Figure 7:
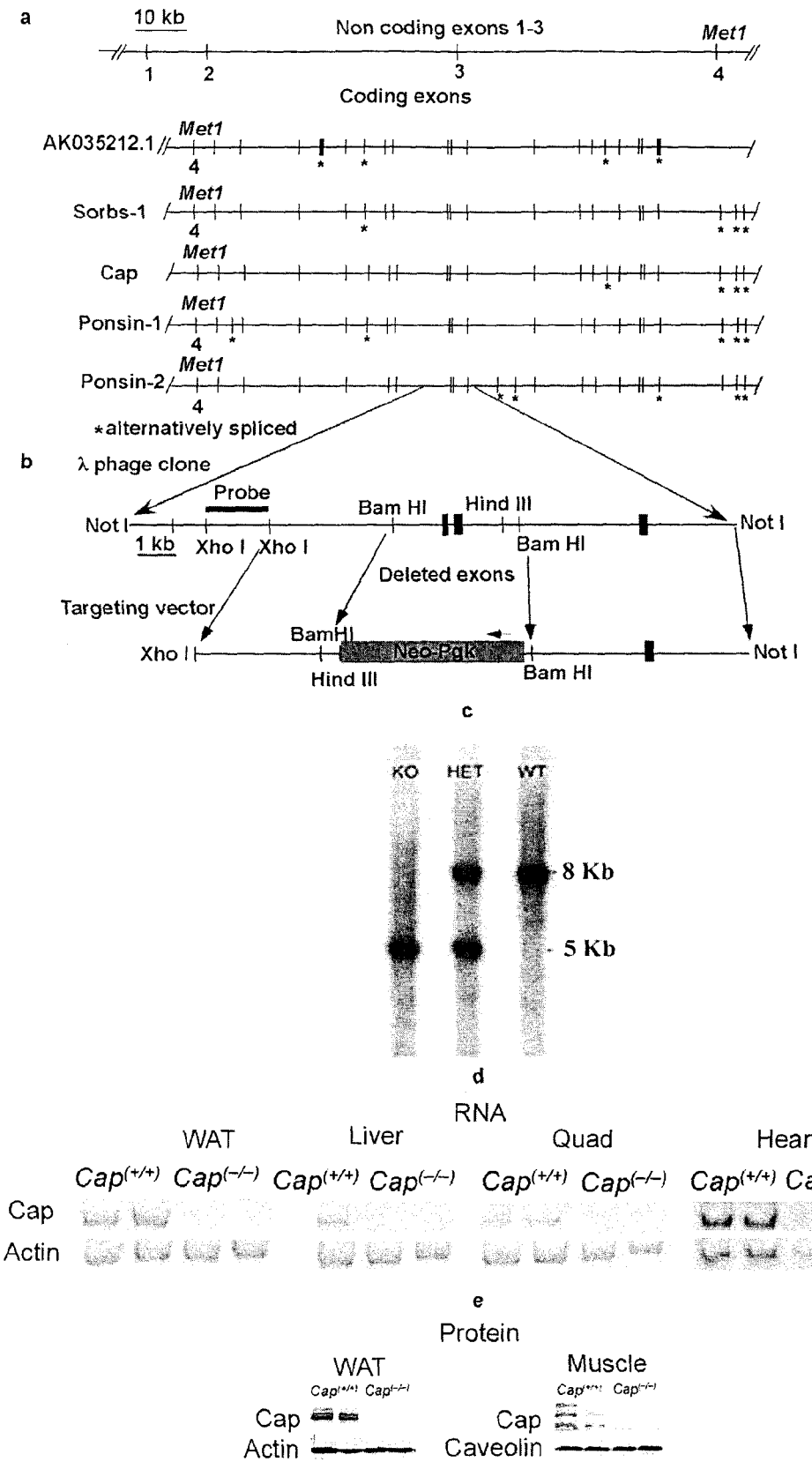
FIG. 7 illustrates metabolic studies on whole body Cap knockout mice. Cap is expressed in muscle, liver and adipose tissues (FIG. 7a-c), and is absent in all three tissues upon deletion of the Cap gene (FIG. 7d, e).

Generation of $Cap_{(-/-)}$ mice. A lambda phage genomic library (Stratagene) was screened and a lambda phage clone containing the middle exons common to all the known publicly available transcripts of SH3P12 (Cap) was isolated. Overlapping fragments of the lambda phage clone were isolated and sequenced. The 3 kb BamHI fragment was eliminated from the final targeting construct (FIG. 7a-c). Two independent clones, D9 and B11, contained the targeted allele and were confirmed by Southern blot and PCR analysis. Elimination of the two exons results in a codon reading frameshift and premature termination of translation. All mice were derived from 129/sv ES cells and backcrossed 7 times into the C57Bl/6 background.

Animal procedures conformed to the Guide for Care and Use of Laboratory Animals of the National Institutes of Health, and were approved by the Animal Subjects Committee of the University of California, San Diego.

High fat feeding. Male mice (5-6 mo) were fed a 40% fat by weight (HFD) diet (Harlan Teklad Custom Diets) for 6-8 weeks.

Bone marrow transplantation. Bone marrow from $Cap_{(+/+)}$ and $Cap_{(-/-)}$ mice was injected (~$4 \times 10^6$ cells) via the tail vein into irradiated (1000 rad) male C57bl/6 mice (4 mo) and $Cap_{(-/-)}$ (4-6 mo) mice. Mice were allowed 4 wk for reconstitution of donor marrow, verified by quantitative PCR.

Whole blood and plasma measurements. White blood cell number and differential were assessed by standard techniques (ACP Diagnostic Lab, UCSD). Plasma insulin was measured by radioimmunoassay (Linco Research), and free fatty acids by colorimetric assay (Wako). Plasma cytokines were measured by the core laboratories of the Diabetes and Endocrinology Research Consortium (UCLA).

Glucose and insulin tolerance tests and hyperinsulinemic-euglycemic clamps. Glucose and insulin tolerance tests[25] and mouse clamping (Insulin: 12.0 mU/kg/min) were performed as previously described[26] (Supplemental Methods).

Metabolic Cage Studies. NC and HFD fed $Cap_{(+/+)}$ and $Cap_{(-/-)}$ mice (N=8 per genotype) were placed in standard metabolic cages with measurements made on 3 consecutive days.

Magnetic resonance imaging and data segmentation. HFD $Cap_{(+/+)}$ and $Cap_{(-/-)}$ mice were imaged in a 5 cm volume MR imaging coil, using a horizontal bore 7T MR scanner (GE Medical Systems, Milwaukee). The images were segmented and volumes rendered using AMIRA software (Template Graphic Software, San Diego, Calif.).

Western blotting. Western blotting was performed on epididymal fat and quadriceps muscles collected from fasted mice or 15 min after ip injection of insulin (0.85 U/kg). Immunoblots were analyzed by densitometry and expressed in arbitrary units.

Stromal Vascular Fraction (SVF) Isolation. Epidydimal fat pads from mice on NC or HFD were minced in PBS and digested with collagenase (Sigma). Cell suspensions were filtered and SVF cells were lysed in RIPA buffer and immunoblotted.

RNA isolation and reverse transcription-PCR (RT-PCR). Total RNA was isolated from the collected tissues using Qiazol and the RNeasy kit (Qiagen.) RT-PCR was performed using One-step RT-PCR kit (Qiagen).

Histochemistry. Paraffin-embedded adipose tissue sections were stained with hematoxylin and eosin. Adipocytes (150-200 adipocytes/mouse, 3 mice/genotype) were traced and area was calculated using ImageJ software (NIH freeware).

Immunohistochemistry for F4/80+ was performed on adipose sections 13, 27. Data presented as percentage of total adipocytes surrounded by F4/80+ cells (400-600 adipocytes/mouse, >5 mice/genotype).

Ex vivo lipogenesis assay. All experiments were performed at 4_M glucose, a concentration at which glucose uptake is rate limiting, thus effectively measuring glucose uptake in the isolated adipocytes. Experiments were performed in triplicate and normalized to protein amount and cell number. Results were similar regardless of normalization, data are presented normalized to protein amount.

Macrophage spreading, migration and c-Cbl phosphorylation.

Knockdown in RAW264 macrophages. RAW264 macrophages were transfected with modified siRNA (Stealth, Invitrogen) directed against Cap 666-691 bp and a scrambled sequence control using Lipofectamine 2000. All studies were performed 72 hours after transfection.

Cell spreading. Cells were placed on collagen-coated coverslips, were fixed and stained with Alexa 488 phalloidin.

Wound Healing Assay. Cells were plated to confluence and wounds in the monolayer were created by scraping the plate with a pipette tip. Cells were stimulated with LPS (0.1 µg/mL) and photographed.

c-Cbl phosphorylation. Cells were placed in suspension for 20 min and replated on plastic. Lysates were harvested and immunoprecipitated with cCbl antibody conjugated agarose beads (Upstate). Bound proteins were separated and immunoblotted with c-Cbl specific or phosphotyrosine-specific (Upstate) antibodies.

Statistical Analysis. ANOVA with LSD post hoc testing were used to determine group differences. Repeated measures ANOVA with LSD post hoc testing were used for comparisons over time.

Example 1

Whole Body CAP Deletion Protects Against Insulin Resistance

Prior studies have shown the Cbl/CAP pathway as an alternate PI3K-independent insulin signaling cascade that leads to GLUT4 translocation, with CAP gene depletion resulting in an almost complete blockade of glucose uptake in cultured adipocytes. In contrast, the results reported herein demonstrate that, contrary to what has been observed in cultured cells, in vivo CAP deletion protects against high fat diet-induced insulin resistance.

Male CAP knockout mice (CAP, N=7) and age-matched C57/BL6 (CNT, N=5) were studied at 6-10 months of age while maintained on a normal chow and following ≧4 weeks of high fat diet (HFD) (40% calories from fat). Glucose tolerance and insulin sensitivity were assessed with ip glucose and insulin tolerance tests as well as euglycemic-hyperinsulinemic clamp studies. For glucose and insulin tolerance tests, animals were fasted 5 h and a basal blood sample taken. Animals were injected with glucose (100 mg/kg) or insulin (0.85 units/kg; Novolin R. Novo-Nordisk, Copenhagen), ip. Blood samples were taken at 15, 30, 45, 60, 90, and 120 min or 10, 20, 30, 45, 60, 90, 120 min; respectively for the determination of blood glucose concentration. Mouse clamping was performed as previously described (Gu, X. and Spitzer, N. C., J Neurosci. 13: 4936-4948, 1993).

Results showed that body mass was significantly greater in CAP knockout mice during both normal chow and high fat feeding relative to age-matched controls. During high fat feeding, despite the higher total body mass, the mass of both the liver and epididymal fat pad was lower in the knockout mice compared to controls, although heart mass was greater. Glucose tolerance tests revealed a modest augmentation of glucose tolerance when mice were maintained on a normal chow diet. Following high fat diet, control mice displayed a significant decrease in glucose tolerance that was not present in the knockout mice. Similarly, in response to an ip insulin load, knockout mice responded with a greater reduction in blood glucose than the age-matched controls, indicative of increased insulin sensitivity in the knockout mice. This was further supported by the patch clamp studies, in which glucose disposal rate (CNT HFD: 25.2+/−6.5 vs. CAP HFD: 38.3+/−4.7 mg/kg/min) and the ability of insulin to suppress hepatic glucose output were increased (CNT HFD: 47% vs. CAP HFD: 78%) in the CAP knockout mice.

These data demonstrate that in vivo CAP deletion protects against high fat diet-induced insulin resistance.

in mice receiving CAP marrow compared to those receiving WT marrow. This was further supported by the clamp studies, in which glucose disposal rate was higher in the macrophage-specific CAP knockout mice compared to WT controls (WT: 22.3+/−3.5 vs. CAP: 70.8+/−5.6 mg/kg/min).

Thus, CAP deletion in macrophages protects against high fat-induced insulin resistance. Because bone marrow cells can be obtained from humans, grown in vitro, modified genetically and administered to a human, including the donor of the bone marrow cells, these results provide a method of treatment of diabetes and other diseases and disorders involving insulin metabolism in humans in need of treatment.

TABLE 1

Body mass, tissue mass, and circulating factors in CAPKO and WT mice on normal chow (NC) and high fat diet (HFD).

|  | WT | | CAPKO | |
| --- | --- | --- | --- | --- |
|  | NC | HFD | NC | HFD |
| Body Mass (g) | 30.9 ± 0.8 | 36.9 ± 0.9 | 31.3 ± 1.2 | 39.5 ± 1.0 |
| Gastrocnemius Muscle Mass (mg) | 157 ± 7 | 164 ± 6 | 142 ± 10 | 148 ± 6 |
| Liver Mass (g) | 1.34 ± 0.05 | 1.56 ± 0.09 | 1.24 ± 0.06 | 1.46 ± 0.06 |
| WAT Mass (g) | 0.88 ± 0.12 | 1.92 ± 0.13 | 0.83 ± 0.11 | 1.88 ± 0.10 |
| Circulating Factors: | | | | |
| FFAs (µM/ml) | 0.65 ± 0.05 | 0.67 ± 0.11 | 0.91 ± 0.09 | 0.93 ± 0.12 |
| MCP-1 (pg/ml) | 53.29 ± 2.21 | 78.50 ± 11.50 | 64.75 ± 7.72 | 54.25 ± 3.22 |
| TPAI-1 (pg/ml) | 722.7 ± 175.7 | 1554 ± 225.8 | — | 1108.7 ± 89.9 |
| Resistin (pg/ml) | 247.4 ± 54.5 | 915.7 ± 237.1 | 188.0 ± 9.9 | 890.7 ± 132.2 |
| Leptin (pg/ml) | 916.9 ± 123.4 | 6865 ± 1326 | 2523.5 ± 730.0 | 7403 ± 1123 |

Example 2

Macrophage-Specific CAP Deletion Confers Protection from Insulin Resistance

As shown in Example 1, whole body CAP gene deletion results in protection from high fat diet-induced insulin resistance. Utilizing bone marrow transplantation to yield macrophage-specific CAP knockout mice, it is shown herein that such protection results from abnormal macrophage function following deletion of the CAP gene.

Macrophage specific genotypes were generated by introducing bone marrow from either whole body CAP knockout mice (CAP, N=5) or wildtype donors (WT, N=5) into irradiated wildtype hosts via tail vein injection. Bone marrow was harvested from CAP knockout (CAPKO) and WT donor mice. Approximately, 2×10$^6$ cells were injected into irradiated (1000 rad) recipient male C57/BL6 mice (4 mo) via the tail vein. Mice were allowed 4 weeks to reconstitute CAPKO or WT bone marrow, thus creating a macrophage-specific CAP-deleted mice as well as control mice. Receipient mice were then placed on high fat diet for 4-8 weeks. Glucose tolerance and insulin sensitivity were assessed with ip glucose and insulin tolerance tests as well as euglycemic-hyperinsulinemic clamp studies, as described in Example 1.

Results showed that, following high fat diet, in response to ip glucose or insulin, mice comprising CAP-deleted macrophages responded with lower blood glucose values and greater reduction in blood glucose, respectively, indicative of the maintenance of glucose tolerance and insulin sensitivity

TABLE 2

Body mass, tissue mass, and circulating factors in mice receiving bone marrow transplants from CAPKO and WT mice on high fat diet (HFD).

|  | BMT | |
| --- | --- | --- |
|  | WT | CAPKO |
| Body Mass (g) | 34.3 ± 1.0 | 32.2 ± 0.8 |
| Gastrocnemius Muscle Mass (mg) | 137 ± 4 | 136 ± 2 |
| Liver Mass (g) | 1.9 ± 0.1 | 1.9 ± 0.1 |
| WAT Mass (g) | 1.9 ± 0.1 | 1.8 ± 0.1 |
| Circulating Factors: | | |
| FFAs (µM/ml) | 0.77 ± 0.06 | 0.72 ± 0.05 |
| MCP-1 (pg/ml) | ± | 71.4 ± 14.5 |
| TPAI-1 (pg/ml) | ± | 2385.9 ± 238.9 |
| Resistin (pg/ml) | ± | 1385.0 ± 447.6 |
| Leptin (pg/ml) | ± | 9091.5 ± 1027.1 |
| White Blood Cell Count (×1000/cu mm) | 8.3 ± 2.3 | 4.3 ± 0.6 |
| Lymphocyte (#) | 5821 ± 1921 | 2783 ± 605 |
| Neutrophil (#) | 1391 ± 75 | 1013 ± 200 |
| Monocyte (#) | 556 ± 101 | 367 ± 55 |
| Eosinophil (#) | 242 ± 118 | 70 ± 17 |

Example 3

In this example, whole body Cap knockout mice for metabolic studies are generated (FIG. 7a-c). Cap is expressed in muscle, liver and adipose tissues, and is absent in all three tissues upon deletion of the Cap gene (FIG. 7d, e). Whole body, and organ weights did not differ between $Cap_{(+/+)}$ and $Cap_{(-/-)}$ mice on normal chow (NC) or HFD (Table 3). When fed HFD, an 11-fold increase in liver triglyceride was seen in the $Cap_{(+/+)}$ mice compared to only a 2-fold increase in the $Cap_{(-/-)}$ mice (Table 3).

Adipocyte size was greater in the $Cap_{(-/-)}$ mice compared to $Cap_{(+/+)}$ mice while maintained on NC despite a lack of difference in WAT mass, suggestive of a smaller number of total adipocytes in the $Cap_{(-/-)}$ mice (Table 3). Moreover, although HFD increased adipocyte size in the $Cap_{(+/+)}$ mice, there was no significant increase in size in the $Cap_{(-/-)}$ mice following HFD.

Although no differences in plasma adiponectin were found between the $Cap_{(+/+)}$ and $Cap_{(-/-)}$ mice on either NC or HFD, plasma leptin increased in both genotypes following HFD, with no differences found between the $Cap_{(+/+)}$ and $Cap_{(-/-)}$ mice (Table 3).

Spontaneous cage activity and metabolic rate were assessed in $Cap_{(+/+)}$ and $Cap_{(-/-)}$ mice on both NC and HFD (N=8/genotype). No differences in $VO_2$, $VCO_2$, food consumption or spontaneous cage activity were seen between genotypes, although RER decreased in both the $Cap_{(+/+)}$ and $Cap_{(-/-)}$ mice following HFD (FIG. 12). Body composition was also assessed in HFD $Cap_{(+/+)}$ and $Cap_{(-/-)}$ mice by MRI, and there were no differences between the genotypes for lean body, visceral fat, or subcutaneous fat volumes (FIG. 12).

TABLE 3

Animal characteristics, insulin sensitivity and macrophage infiltration into adipose tissue following reverse BMT experiments.

|  | Cap(−/−) mice receiving | |
| --- | --- | --- |
|  | Cap(+/+) | Cap(−/−) |
| Body Mass (g) | 30.1 ± 1.7 | 31.2 ± 1.1 |
| Liver Mass (g) | 1.34 ± 0.09 | 1.34 ± 0.11 |
| Liver Triglyceride Content (mg/g) | 71.6 ± 13.2 | 53.6 ± 8.1 |
| WAT Mass (g) | 0.93 ± 0.16 | 0.79 ± 0.05 |
| Blood Glucose (mg/dl) | 117 ± 5.1 | 117 ± 7.1 |
| GIR (mg/kg/min) | 74.5 ± 10.9 | 73.8 ± 6.4 |
| IS-GDR (mg/kg/min) | 62.6 ± 12.1 | 56.5 ± 7.0 |
| % Suppression of HGP | 52.0 ± 13.3 | 79.2 ± 9.4$_{P=0.1}$ |
| % Adipocytes Surrounded by Macrophages | 1.5 ± 0.4 | 1.4 ± 0.4 |

GIR is the glucose infusion rate during clamps, IS-GDR is the insulin stimulated glucose disposal rate during clamps, and HGP is hepatic glucose production.

Example 4

This example illustrates that Cap deletion is protective against HFD-induced insulin resistance.

Figure 8:
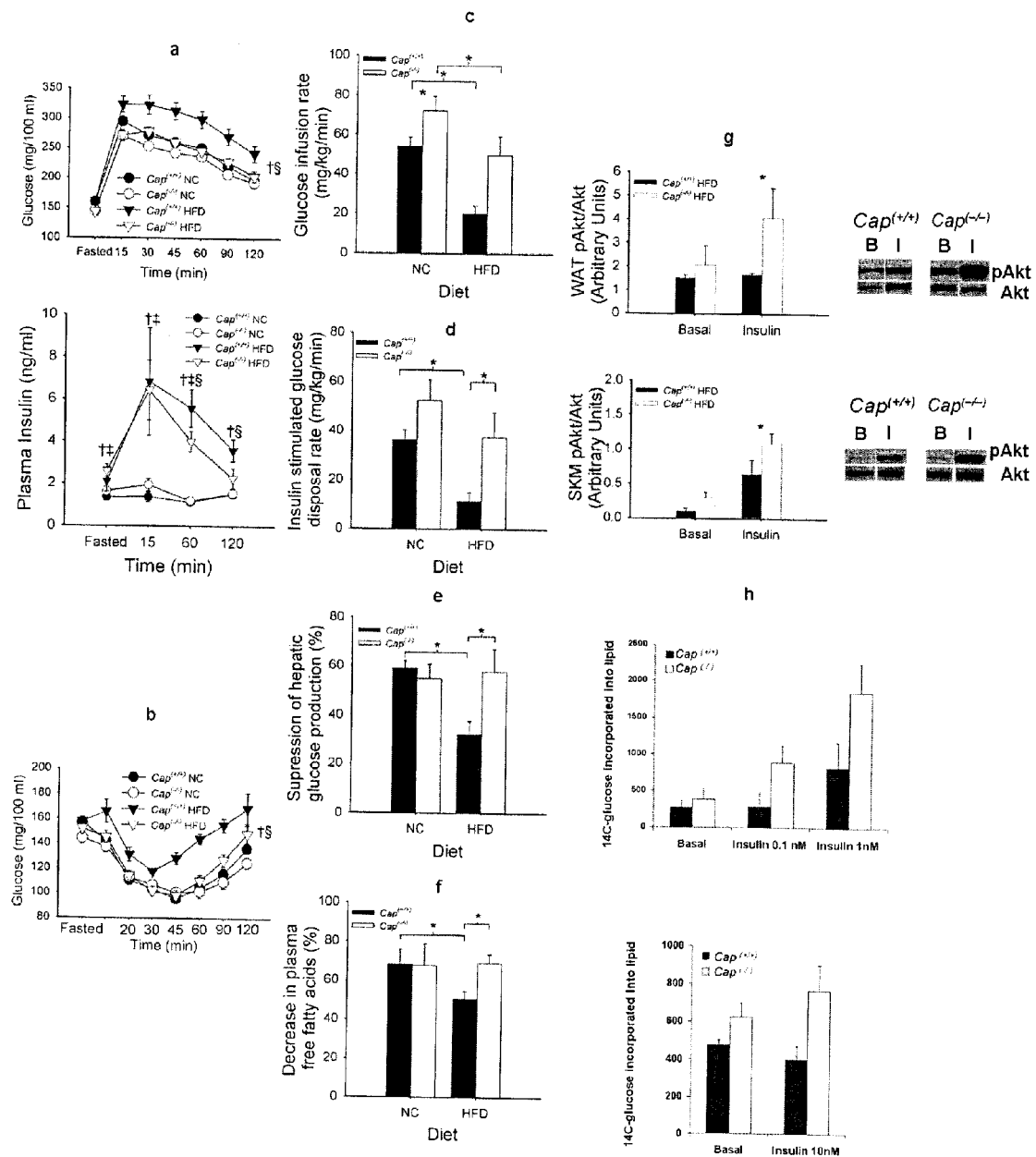
FIG. 8 illustrates that Cap deletion is protective against HFD-induced insulin resistance.

Despite the positive role of Cbl/Cap in stimulating insulin-induced GLUT4 translocation and glucose uptake in cultured adipocytes, insulin sensitivity was not impaired by Cap gene deletion in vivo. Thus, no differences in glucose or insulin tolerance were observed between $Cap_{(+/+)}$ and $Cap_{(-/-)}$ mice while fed NC (FIG. 8a, b). Surprisingly, even when maintained on NC, the glucose infusion rate (P=0.04) and glucose disposal rate (P=0.07) were both higher (~40%) in the $Cap_{(-/-)}$ compared to $Cap_{(+/+)}$ mice (FIG. 8c, d). Strikingly, the $Cap_{(+/+)}$ mice developed the expected impaired glucose and insulin tolerance following HFD, but the $Cap_{(-/-)}$ mice were protected from HFD-induced defects in glucose and insulin homeostasis (FIG. 8a, b). Although plasma insulin was elevated in both the $Cap_{(+/+)}$ and $Cap_{(-/-)}$ mice following HFD in the basal state (Table 3), we found a significant decrease in plasma insulin at 60 and 120 min of the GTT in HFD $Cap_{(-/-)}$ mice compared to the $Cap_{(+/+)}$ mice, consistent with the improved glucose tolerance (FIG. 8a, lower panel). These observations were further supported by euglycemic clamp studies, in which HFD-induced the usual state of insulin resistance in the $Cap_{(+/+)}$ mice, as manifested by a decrease in glucose infusion rate, glucose disposal rate, suppression of hepatic glucose output, and suppression of circulating free fatty acids (FIG. 8c-f). In marked contrast, each measurement of insulin sensitivity in skeletal muscle (GDR), liver (HGO suppression), and adipose tissue (FFA levels) remained normal in the $Cap_{(-/-)}$ mice despite HFD (FIG. 8c-f).

Enhanced signaling through the PI3K pathway may explain the maintenance of insulin sensitivity in the HFD $Cap_{(-/-)}$ mice. Indeed, we found increased phosphorylation of Akt following 15 min of insulin stimulation in both the WAT and skeletal muscle of $Cap_{(-/-)}$ mice compared to $Cap_{(+/+)}$ controls following HFD (FIG. 8g). No differences in the phosphorylation of the insulin receptor or insulin receptor substrate-1 were found (data not shown).

Interestingly, ex vivo lipogenesis experiments revealed an increase in insulin stimulated glucose incorporation into lipid in adipocytes isolated from $Cap_{(-/-)}$ mice compared to those from $Cap_{(+/+)}$ mice (FIG. 8h), a finding that indicates enhanced insulin sensitivity in the adipose tissue of the $Cap_{(-/-)}$ mice. This demonstrates that adipocyte $Cap_{(-/-)}$ leads to increased insulin sensitivity, even when mice are maintained on NC diet.

Example 5

This example illustrates that $Cap_{(-/-)}$ mice exhibit reduced macrophage infiltration in adipose tissue.

It is known that HFD leads to increased adipose tissue macrophages and inflammation in $Cap_{(+/+)}$ mice, and it seemed possible that this was reduced in the $Cap_{(-/-)}$ mice. Interestingly, in the stromal vascular fraction (SVF) of the adipose tissue, which contains the infiltrating macrophages, both Cap and Cbl protein are up-regulated following HFD (FIG. 9a), suggesting that Cap may be expressed in the macrophages.

Figure 9:
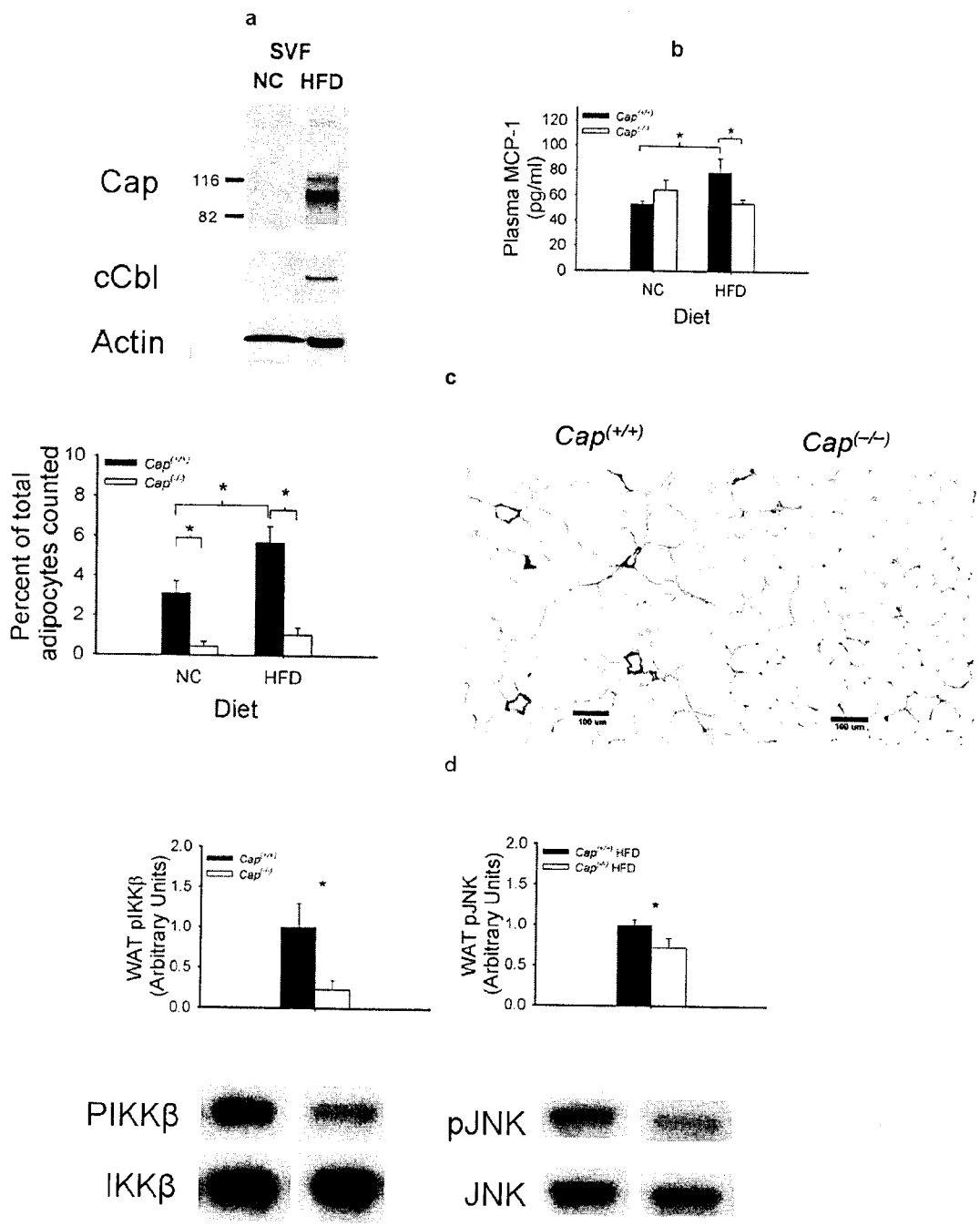
FIG. 9 illustrates that in the stromal vascular fraction (SVF) of the adipose tissue, which contains the infiltrating macrophages, both Cap and Cbl protein are up-regulated following HFD (FIG. 9a), implying that Cap may be expressed in the macrophages.

We demonstrate that while circulating MCP-1 levels increased in $Cap_{(+/+)}$ mice following HFD, MCP-1 was unaltered in $Cap_{(-/-)}$ mice (FIG. 9b), suggesting a decrease in adipose tissue macrophage content in $Cap_{(-/-)}$ mice. Indeed, as assessed by staining for F4/80+ cells in histological sections of adipose tissue, we show a marked (80%) reduction in adipose tissue macrophage content in the $Cap_{(-/-)}$ mice compared to $Cap_{(+/+)}$ mice on either NC or HFD (FIG. 9c). Furthermore, there was a significant reduction in both phosphorylated IKK-β (P<0.01) and JNK (P<0.05) in the WAT of $Cap_{(-/-)}$ mice compared to wild type mice when fed HFD (FIG. 9d). These observations led us to hypothesize that Cap may play an unrecognized, but important, role in macrophage recruitment and/or function.

Example 6

Figure 10:
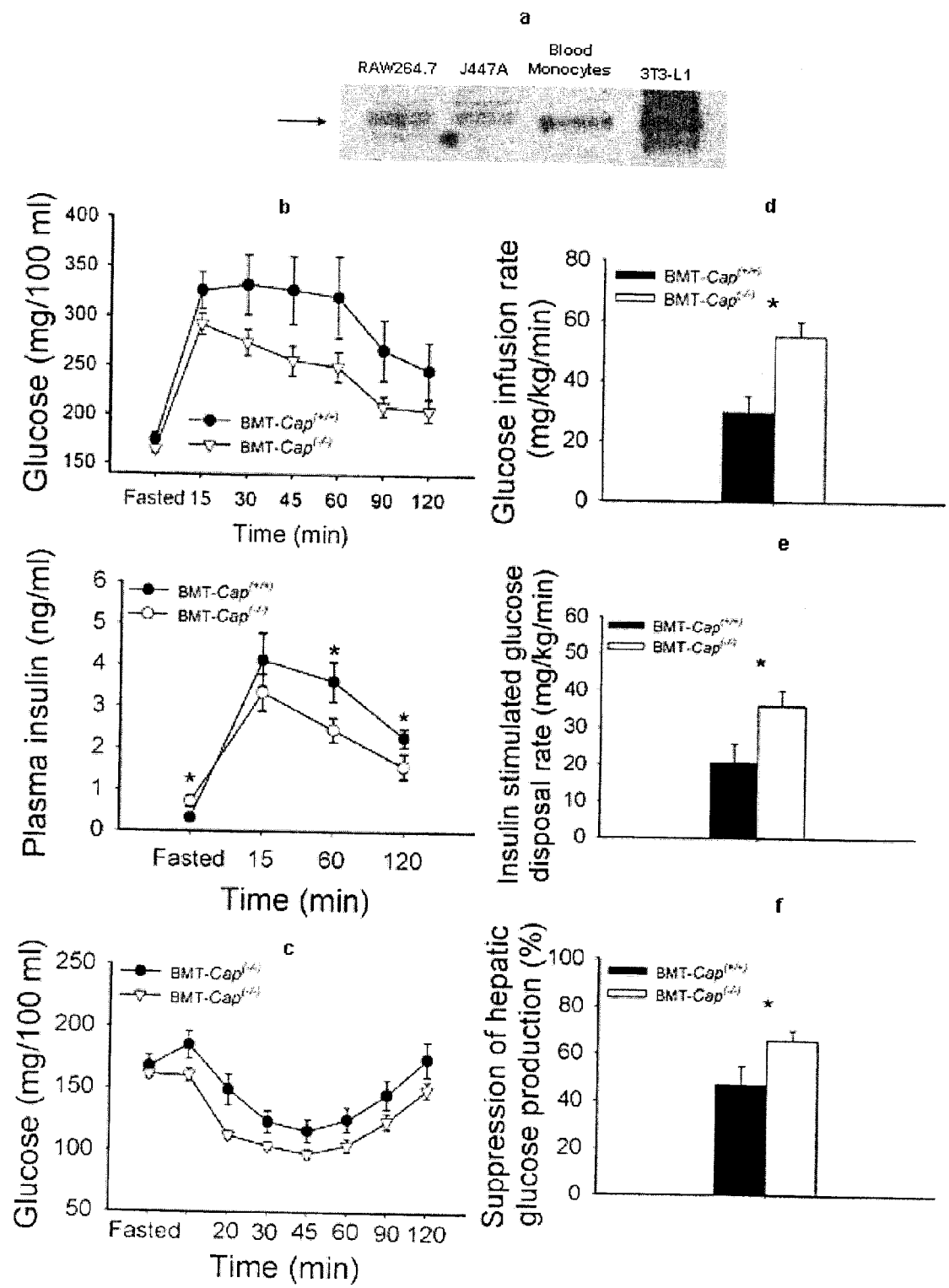
FIG. 10 illustrates Cap expression in macrophages, and that Insulin sensitivity is preserved in BMT-$Cap_{(-/-)}$ mice.

This example illustrates that bone marrow transplant from $Cap_{(-/-)}$ mice is sufficient to confer protection from HFD-induced insulin resistance. The increase in Cap in the SVF after HFD (FIG. 9a) suggested that Cap is expressed in macrophages, here we directly show that Cap is expressed in both primary blood derived monocytes and in the immortalized macrophage cell lines, RAW264.7 and J774A (FIG. 10a).

To examine the role of Cap in the macrophage as it relates to the in vivo insulin sensitive phenotype in the $Cap_{(-/-)}$ mice, we utilized bone marrow transplantation (BMT) from $Cap_{(-/-)}$ to wildtype C57bl/6 (WT) mice to create macrophage $Cap_{(-/-)}$ mice. Recipient mice were allowed 4 weeks for reconstitution of the transplanted bone marrow and were then placed on HFD for 6-8 weeks prior to metabolic experiments. RT-PCR confirmed reconstitution of $Cap_{(-/-)}$ bone marrow in WT host mice, with a 99.1% reduction in Cap gene expression in the marrow of BMT-$Cap_{(-/-)}$ animals.

Following HFD, no differences in body weight, liver mass, adipose mass or hepatic triglyceride content were found between WT mice receiving bone marrow from wildtype (BMT-$Cap_{(+/+)}$) or $Cap_{(-/-)}$ mice (BMT-$Cap_{(-/-)}$) (Table 3).

Example 7

This example illustrates that insulin sensitivity is preserved in BMT-$Cap_{(-/-)}$ mice. The BMT-$Cap_{(+/+)}$ animals on HFD were glucose intolerant (FIG. 10b, upper panel) and hyperinsulinemic (FIG. 10b, lower panel) compared to the BMT-$Cap_{(-/-)}$ mice. Similarly, the ITTs (FIG. 10c) showed enhanced overall insulin sensitivity in the BMT-$Cap_{(-/-)}$ mice compared to BMT$Cap_{(+/+)}$.

This protection from HFD-induced insulin resistance in the BMT-$Cap_{(-/-)}$ was further supported by euglycemic clamp studies (FIG. 10d-f), which demonstrated higher glucose infusion rates, glucose disposal rates, and suppression of hepatic glucose output in the BMT-$Cap_{(-/-)}$ mice compared to BMT-$Cap_{(+/+)}$. In BMT experiments, all of the hematopoietic lineages are reconstituted from donor mice and, therefore, any BM cell type which normally expresses Cap would show Cap deletion. However, since there is no evidence in the literature that lymphocytes or granulocytes play any role in the chronic inflammation which leads to insulin resistance, we conclude that the insulin sensitive phenotype in the BMT-$Cap_{(-/-)}$ is related to Cap knockout in the macrophage lineage.

Example 8

Figure 11:
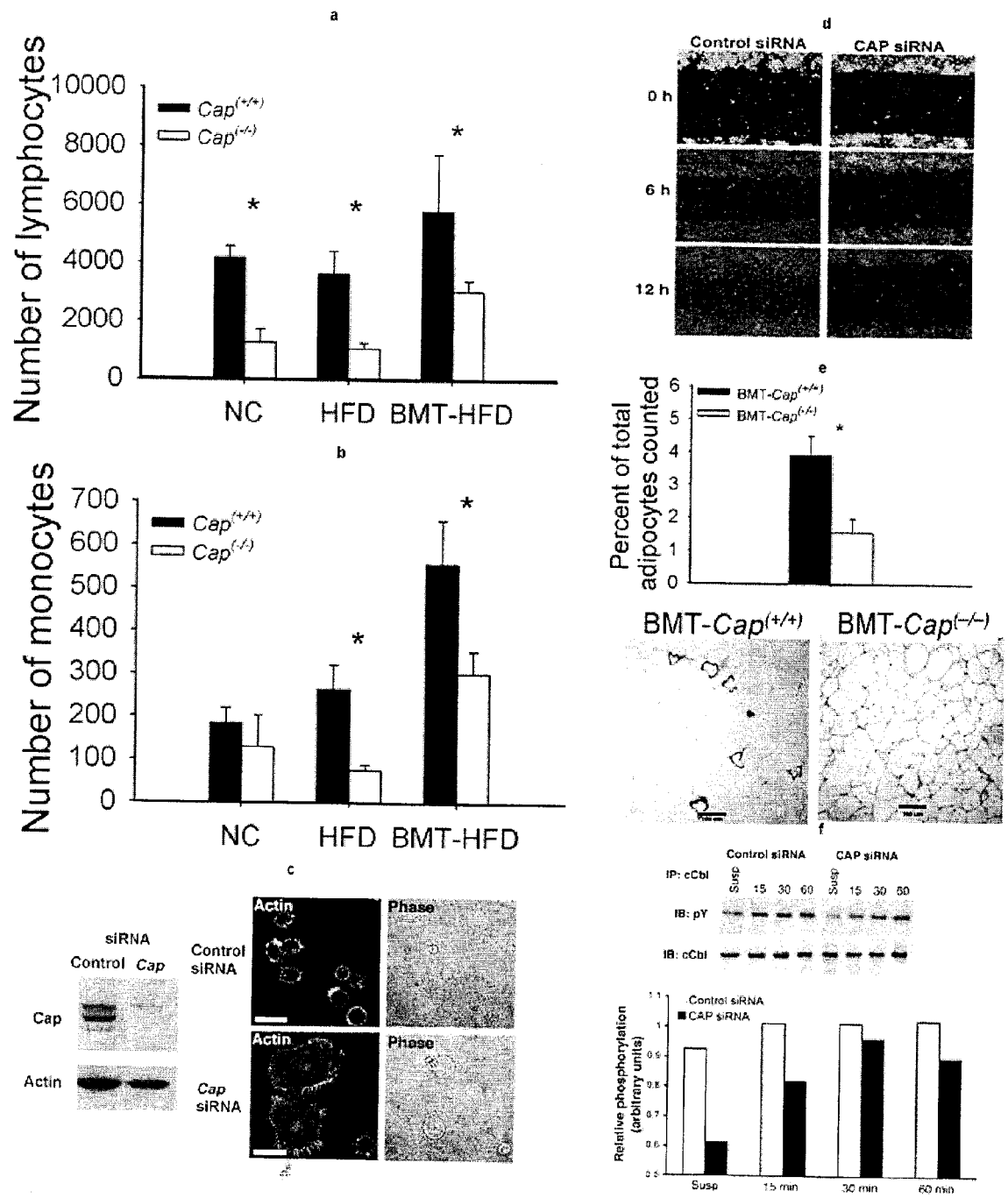
FIG. 11 illustrates that Cap deletion influences WBC levels and inhibits macrophage migration. The different white blood cell lineages were examined for alterations in WBC levels and macrophage migration. Both whole body and bone-marrow-specific Cap gene deletion led to decreased total white blood cells (data not shown), decreased lymphocytes irrespective of diet (FIG. 11a) and decreased monocytes when fed HFD (FIG. 11b). These data suggest that Cap may be involved in the differentiation of specific myeloid cell types. In order to assess the role of Cap in macrophage function, a number of cellular processes were evaluated in Cap-deficient cells. We treated RAW264.7 cells with Cap siRNA and reduced Cap expression by >90%. Following Cap knockdown, macrophages displayed increased cell spreading as evidenced by an increase in cell size and a flatter appearance (FIG. 11c). In addition, the migratory capacity of these macrophages was assessed using a wound healing assay. RAW264.7 cells transfected with either Cap siRNA or scrambled siRNA were plated to confluence and the cells were "wounded" by scraping the plate. The migration of macrophages back into the wound area following LPS stimulation was then assessed. Cap knockdown results in reduced cell migration into the wound area in compared to cells transfected with control siRNA (FIG. 11d). This finding, is consistent with the marked decrease in macrophages in adipose tissue from $Cap_{(-/-)}$ and BMT-$Cap_{(-/-)}$ mice on HFD (FIG. 11e). Adhesion triggers phosphorylation of Cbl in macrophages, and to determine if Cap deficiency modulates Cbl activity, adhesion-induced Cbl phosphorylation was assessed in Cap knockdown macrophages. SiRNA-mediated knockdown of Cap reduced Cbl phosphorylation at early time points after adhesion (FIG. 11f), suggesting that Cap gene deletion might compromise macrophage migratory capacity by attenuating Cbl function.

This example illustrates that Cap deletion influences WBC levels and inhibits macrophage migration. Cbl plays a critical role in cell survival, differentiation, adhesion and motility of macrophages[15-18], and in concert with Cbl, Cap may play a role in macrophage function. To assess this, we measured the different white blood cell lineages. Interestingly, both whole body and bone-marrow-specific Cap gene deletion led to decreased total white blood cells (data not shown), decreased lymphocytes irrespective of diet (FIG. 11a) and decreased monocytes when fed HFD (FIG. 11b). These data suggest that Cap may be involved in the differentiation of specific myeloid cell types. In order to assess the role of Cap in macrophage function, a number of cellular processes were evaluated in Cap-deficient cells. We treated RAW264.7 cells with Cap siRNA and reduced Cap expression by >90%. Following Cap knockdown, macrophages displayed increased cell spreading as evidenced by an increase in cell size and a flatter appearance (FIG. 11c). In addition, the migratory capacity of these macrophages was assessed using a wound healing assay. RAW264.7 cells transfected with either Cap siRNA or scrambled siRNA were plated to confluence and the cells were "wounded" by
scraping the plate. The migration of macrophages back into the wound area following LPS stimulation was then assessed. Cap knockdown results in reduced cell migration into the wound area in compared to cells transfected with control siRNA (FIG. 11d). This finding, is consistent with the marked decrease in macrophages in adipose tissue from $Cap_{(-/-)}$ and BMT-$Cap_{(-/-)}$ mice on HFD (FIG. 11e).

Adhesion triggers phosphorylation of Cbl in macrophages 19, and to determine if Cap deficiency modulates Cbl activity, adhesion-induced Cbl phosphorylation was assessed in Cap knockdown macrophages. SiRNA-mediated knockdown of Cap reduced Cbl phosphorylation at early time points after adhesion (FIG. 11f), suggesting that Cap gene deletion might compromise macrophage migratory capacity by attenuating Cbl function.

To further evaluate the role of Cap in the activity of mature macrophages, thioglycollate-elicited peritoneal macrophages were isolated from both $Cap_{(+/+)}$ and $Cap_{(-/-)}$ mice. The macrophages were stimulated ex vivo with lipopolysaccharide (LPS; 1 ng/ml) for 5 and 30 min, and the activation of inflammatory pathway cascades was evaluated by Western blot analysis. Phosphorylation of JNK (30 min) and IKK-® (5 min) were not different between $Cap_{(+/+)}$ and $Cap_{(-/-)}$ macrophages, nor was NF/B activation (not shown). These data suggest that while it plays an important role in supporting Cbl tyrosine phosphorylation, Cap is not essential to macrophage activation.

Example 9

This example illustrates that transplantation of $Cap_{(+/+)}$ bone marrow into $Cap_{(-/-)}$ mice only partially reverses the insulin sensitive phenotype. From the previous findings, we hypothesized that the transplantation of $Cap_{(+/+)}$ and bone marrow into irradiated $Cap_{(-/-)}$ mice might restore the development of insulin resistance in response to HFD. In these reverse BMT experiments, RT-PCR confirmed reconstitution of $Cap_{(+/+)}$ bone marrow in $Cap_{(-/-)}$ host mice, with 99.5% WT Cap gene expression in $Cap_{(-/-)}$ mice receiving marrow from $Cap_{(+/+)}$ mice. Surprisingly, glucose and insulin tolerance were indistinguishable between $Cap_{(-/-)}$ mice that received $Cap_{(+/+)}$ marrow and those receiving $Cap_{(-/-)}$ bone marrow (data not shown). Similarly, muscle insulin sensitivity was preserved in $Cap_{(-/-)}$ mice receiving $Cap_{(+/+)}$ marrow (Table 3). In contrast, hepatic insulin resistance developed in the $Cap_{(-/-)}$ mice receiving $Cap_{(+/+)}$ marrow following HFD, as seen by impaired suppression of HGO during the glucose clamp study. Thus, the effect of HFD to cause decreased insulin sensitivity was only partially restored in these mice.

Interestingly, the macrophage content of adipose tissue from $Cap_{(-/-)}$ receiving $Cap_{(+/+)}$ marrow was markedly reduced compared to BMT-$Cap_{(+/+)}$ mice (Table 3) comparable to the decreases observed in the $Cap_{(-/-)}$ and BMT-$Cap_{(-/-)}$. These findings suggest that Cap expression in adipose tissue may be essential to signal the recruitment of macrophages to this tissue, consistent with the earlier results demonstrating a lack of HFD-induced increase in plasma MCP-1 levels in $Cap_{(-/-)}$ mice (FIG. 9b).

Aspects

The present application includes the following aspects:

1. A method for treating insulin resistance in a subject, the method comprising:
   administering to the subject in need thereof a composition comprising a therapeutically effective amount of a CAP antagonist.

2. A method for treating type 2 diabetes in a subject, the method comprising:
   administering to the subject in need thereof a composition comprising a therapeutically effective amount of a CAP antagonist.

3. A method for protecting a subject from high fat diet induced whole body insulin resistance, the method comprising:
   administering to the subject in need thereof a composition comprising a therapeutically effective amount of a CAP antagonist.

4. A method for disrupting the inflammatory process associated with insulin resistance in a subject, the method comprising:
   administering to the subject in need thereof a composition comprising a therapeutically effective amount of a CAP antagonist.

5. The method of any one of aspects 1-4, wherein the CAP antagonist is selected from the group consisting of small organic compound, inorganic compound, oligopeptide, Abs, Abs derivatives, CAP-homologous polypeptide, antisense DNA, antisense RNA, ribozyme, triple DNA helices, siRNA, and nucleic acid aptamers.

6. The method of any one of aspects 1-5, wherein the CAP antagonist is a purified, isolated antibody directed against CAP, wherein the antibody binds CAP with moderate to high affinity.

7. The method of aspect 6, wherein the antibody has an affinity to binding CAP with a dissociation constant of below a Kd value selected from the group consisting of 10-6 mol/l, 10-7 mol/l, and 10-8 mol/l.

8. The method of any one of aspects 6-7 wherein the anti-CAP antibody is a polyclonal antibody, a monoclonal antibody, or a functional antibody fragment.

9. The method of any one of aspects 6-7, wherein the anti-CAP antibody is a whole antibody, a humanized antibody, a chimeric antibody, a Fab fragment, a Fab' fragment, a F(ab')2 fragment, a single chain Fv fragment, or a diabody.

10. The method of any one of aspects 1-9, wherein the anti-CAP antibody is administered in an amount of (i) about 0.05 mg to about 2.5 mg; (ii) about 0.1 mg to about 1 mg; or (iii) about 0.3 mg to about 0.5 mg.

11. The method of any one of aspects 1-4, wherein the CAP antagonist is a CAP-specific siRNA.

12. The method of aspect 11, wherein administration of CAP-specific siRNA results in an intracellular concentration selected from the group consisting of from about 1 nanomolar (nM) to about 100 nM; from about 2 nM to about 50 nM; and from about 2.5 nM to about 10 nM.

13. The method of any one of aspects 1-4, wherein the CAP antagonist is an antisense inhibitor of CAP.

14. The method of aspect 13, wherein the CAP antisense inhibitor is administered in an amount of (i) about 10 μg/day to about 3 mg/day; (ii) about 30 μg/day to about 300 μg/day; or (iii) about 100 μg/day.

15. The method of any one of aspects 1-14, wherein the composition is administered by injection, inhalation, orally, liposome, or retroviral vector.

16. The method of any one of aspects 1-15, wherein the composition further comprises a pharmaceutically acceptable agent.

17. The method of any one of aspects 1-16, wherein insulin action is improved without altering insulin secretion by the pancreas or inhibiting the intestinal glucose absorption.

18. The method of any one of aspects 1-17, wherein CAP is disrupted in a macrophage.

What is claimed is:

1. A method of treating insulin resistance or type 2 diabetes in a subject in need thereof, the method comprising:
   a. providing an in vitro cell culture comprising macrophages derived from haematopoietic stem cells, said derived macrophages having reduced CAP activity in comparison to native macrophages in the subject, wherein reduced CAP activity comprises reduced CAP expression or reduced ability of CAP to interact with Cbl and wherein CAP comprises a sequence as set forth in SEQ ID NO: 1; and
   b. administering an effective amount of the macrophages having reduced CAP activity to the subject, thereby treating insulin resistance or type 2 diabetes in the subject.

2. The method of claim 1, wherein said reduced CAP activity comprises inhibited CAP gene expression.

3. The method of claim 1, wherein the haematopoietic cells are obtained from bone marrow.

4. The method of claim 2, wherein inhibited CAP gene expression in the macrophages results from a disrupted or deleted CAP gene in the macrophages or precursors thereof.

5. The method of claim 4, wherein the disrupted or deleted CAP gene in the macrophages or precursors thereof results from introducing an insertion by homologous recombination into the macrophages or precursors thereof.

6. The method of claim 5, further comprising an earlier step of selecting cells in which the CAP gene is disrupted or deleted.

7. The method of claim 6, further comprising growing the cells in which the CAP gene is disrupted or deleted following the selecting step.

8. The method of claim 2, wherein the macrophages are autologous to the subject.

9. The method of claim 2, wherein the macrophages are syngeneic to the subject.

10. The method of claim 2, wherein the macrophages are allogeneic to the subject.

11. The method of claim 1, wherein the subject in need of treatment has high fat diet-induced whole body insulin resistance.

12. The method of claim 1, wherein the subject is a human.

13. A method of preparing a composition for treating insulin resistance or type 2 diabetes in a subject in need thereof, the method comprising:
   preparing a composition comprising macrophages derived from haematopoietic stem cells, said derived macrophages having reduced CAP activity in comparison to native macrophages in the subject, wherein reduced CAP activity comprises reduced CAP expression or reduced ability of CAP to interact with Cbl.

14. The method of claim 13, wherein CAP comprises a sequence as set forth in SEQ ID NO: 1.

15. The method of claim 13, wherein said reduced CAP activity comprises inhibiting CAP gene expression in the macrophages or precursors thereof.

16. The method of claim 13, wherein the haematopoietic cells are obtained from bone marrow.

17. The method of claim 15, wherein inhibited CAP gene expression in the macrophages comprises a disrupting or deleting the CAP gene in the macrophages or precursors thereof.

18. The method of claim 17, wherein the disrupted or deleted CAP gene in the macrophages or precursors thereof comprises introducing an insertion by homologous recombination into the macrophages or precursors thereof.

19. The method of claim 13, wherein the preparing step further comprises an earlier step of selecting cells in which the CAP gene is disrupted or deleted.

20. The method of claim 19, further comprising growing the cells in which the CAP gene is disrupted or deleted following the selecting step.

* * * * *

SEQUENCE LISTING

<160> NUMBER OF SEQ ID NOS: 22

<210> SEQ ID NO 1
<211> LENGTH: 846
<212> TYPE: PRT
<213> ORGANISM: Homo sapiens

<400> SEQUENCE: 1

```
Met Ser Ser Glu Cys Asp Gly Gly Ser Lys Ala Val Met Asn Gly Leu
1               5                   10                  15

Ala Pro Gly Ser Asn Gly Gln Asp Lys Ala Thr Ala Asp Pro Leu Arg
            20                  25                  30

Ala Arg Ser Ile Ser Ala Val Lys Ile Ile Pro Val Lys Thr Val Lys
        35                  40                  45

Asn Ala Ser Gly Leu Val Leu Pro Thr Asp Met Asp Pro Thr Lys Ile
    50                  55                  60

Cys Thr Gly Lys Gly Ala Val Thr Leu Arg Ala Ser Ser Ser Tyr Arg
65                  70                  75                  80

Glu Thr Pro Ser Ser Pro Ala Ser Pro Gln Glu Thr Arg Gln His
                85                  90                  95

Glu Ser Lys Pro Asp Glu Trp Arg Leu Ser Ser Ser Ala Asp Ala Asn
            100                 105                 110

Gly Asn Ala Gln Pro Ser Ser Leu Ala Ala Lys Gly Tyr Arg Ser Val
        115                 120                 125

His Pro Asn Leu Pro Ser Asp Lys Ser Gln Asp Ser Ser Pro Leu Leu
    130                 135                 140

Asn Glu Val Ser Ser Ser Leu Ile Gly Thr Asp Ser Gln Ala Phe Pro
145                 150                 155                 160
```

```
Ser Val Ser Lys Pro Ser Ser Ala Tyr Pro Ser Thr Thr Ile Val Asn
                165                 170                 175
Pro Thr Ile Val Leu Leu Gln His Asn Arg Glu Gln Gln Lys Arg Leu
            180                 185                 190
Ser Ser Leu Ser Asp Pro Val Ser Glu Arg Arg Val Gly Glu Gln Asp
        195                 200                 205
Ser Ala Pro Thr Gln Glu Lys Pro Thr Ser Pro Gly Lys Ala Ile Glu
    210                 215                 220
Lys Arg Ala Lys Asp Asp Ser Arg Arg Val Val Lys Ser Thr Gln Asp
225                 230                 235                 240
Leu Ser Asp Val Ser Met Asp Glu Val Gly Ile Pro Leu Arg Asn Thr
                245                 250                 255
Glu Arg Ser Lys Asp Trp Tyr Lys Thr Met Phe Lys Gln Ile His Lys
            260                 265                 270
Leu Asn Arg Asp Thr Pro Glu Glu Asn Pro Tyr Phe Pro Thr Tyr Lys
        275                 280                 285
Phe Pro Glu Leu Pro Glu Ile Gln Gln Thr Ser Glu Asp Asn Pro
    290                 295                 300
Tyr Thr Pro Thr Tyr Gln Phe Pro Ala Ser Thr Pro Ser Pro Lys Ser
305                 310                 315                 320
Glu Asp Asp Asp Ser Asp Leu Tyr Ser Pro Arg Tyr Ser Phe Ser Glu
                325                 330                 335
Asp Thr Lys Ser Pro Leu Ser Val Pro Arg Ser Lys Ser Glu Met Ser
            340                 345                 350
Tyr Ile Asp Gly Glu Lys Val Val Lys Arg Ser Ala Thr Leu Pro Leu
        355                 360                 365
Pro Ala Arg Ser Ser Ser Leu Lys Ser Ser Glu Arg Asn Asp Trp
    370                 375                 380
Glu Pro Pro Asp Lys Lys Val Asp Thr Arg Lys Tyr Arg Ala Glu Pro
385                 390                 395                 400
Lys Ser Ile Tyr Glu Tyr Gln Pro Gly Lys Ser Ser Val Leu Thr Asn
                405                 410                 415
Glu Lys Met Ser Arg Asp Ile Ser Pro Glu Glu Ile Asp Leu Lys Asn
            420                 425                 430
Glu Pro Trp Tyr Lys Phe Phe Ser Glu Leu Glu Phe Gly Lys Pro Ser
        435                 440                 445
Ser Ala Ile Ser Pro Thr Pro Glu Ile Ser Ser Glu Thr Pro Gly Tyr
    450                 455                 460
Ile Tyr Ser Ser Asn Phe His Ala Val Lys Arg Glu Ser Asp Gly Ala
465                 470                 475                 480
Pro Gly Asp Leu Thr Ser Leu Glu Asn Glu Arg Gln Ile Tyr Lys Ser
                485                 490                 495
Val Leu Glu Gly Gly Asp Ile Pro Leu Gln Gly Leu Ser Gly Leu Lys
            500                 505                 510
Arg Pro Ser Ser Ser Ala Ser Thr Lys Asp Ser Glu Ser Pro Arg His
        515                 520                 525
Phe Ile Pro Ala Asp Tyr Leu Glu Ser Thr Glu Glu Phe Ile Arg Arg
    530                 535                 540
Arg His Asp Asp Lys Glu Lys Leu Leu Ala Asp Gln Arg Arg Leu Lys
545                 550                 555                 560
Arg Glu Gln Glu Glu Ala Asp Ile Ala Ala Arg Arg His Thr Gly Val
                565                 570                 575
Ile Pro Thr His His Gln Phe Ile Thr Asn Glu Arg Phe Gly Asp Leu
```

```
                580             585             590
Leu Asn Ile Asp Asp Thr Ala Lys Arg Lys Ser Gly Ser Glu Met Arg
        595                 600                 605

Pro Ala Arg Ala Lys Phe Asp Phe Lys Ala Gln Thr Leu Lys Glu Leu
    610                 615                 620

Pro Leu Gln Lys Gly Asp Ile Val Tyr Ile Tyr Lys Gln Ile Asp Gln
625                 630                 635                 640

Asn Trp Tyr Glu Gly Glu His His Gly Arg Val Gly Ile Phe Pro Arg
                645                 650                 655

Thr Tyr Ile Glu Leu Leu Pro Pro Ala Glu Lys Ala Gln Pro Lys Lys
                660                 665                 670

Leu Thr Pro Val Gln Val Leu Glu Tyr Gly Glu Ala Ile Ala Lys Phe
            675                 680                 685

Asn Phe Asn Gly Asp Thr Gln Val Glu Met Ser Phe Arg Lys Gly Glu
        690                 695                 700

Arg Ile Thr Leu Leu Arg Gln Val Asp Glu Asn Trp Tyr Glu Gly Arg
705                 710                 715                 720

Ile Pro Gly Thr Ser Arg Gln Gly Ile Phe Pro Ile Thr Tyr Val Asp
                725                 730                 735

Val Ile Lys Arg Pro Leu Val Lys Asn Pro Val Asp Tyr Met Asp Leu
                740                 745                 750

Pro Phe Ser Ser Pro Ser Arg Ser Ala Thr Ala Ser Pro Gln Gln
            755                 760                 765

Pro Gln Ala Gln Gln Arg Arg Val Thr Pro Asp Arg Ser Gln Thr Ser
        770                 775                 780

Gln Asp Leu Phe Ser Tyr Gln Ala Leu Tyr Ser Tyr Ile Pro Gln Asn
785                 790                 795                 800

Asp Asp Glu Leu Glu Leu Arg Asp Gly Asp Ile Val Asp Val Met Glu
                805                 810                 815

Lys Cys Asp Asp Gly Trp Phe Val Gly Thr Ser Arg Arg Thr Lys Gln
                820                 825                 830

Phe Gly Thr Phe Pro Gly Asn Tyr Val Lys Pro Leu Tyr Leu
        835                 840                 845

<210> SEQ ID NO 2
<211> LENGTH: 2773
<212> TYPE: DNA
<213> ORGANISM: Homo sapiens

<400> SEQUENCE: 2
atgagttctg aatgtgatgg tggttccaaa gctgtgatga atggcttggc acctggcagc      60
aatgggcaag acaaagcaac tgccgaccct ttacgcgcac gctctatttc tgctgttaaa     120
atcattcctg tgaagacagt gaaaaacgcc tcaggcctag ttctccctac agacatggat     180
cctacaaaaa tctgcactgg aagggagcg gtgactctcc gggcctcgtc ttcctacagg     240
gaaaccccaa gcagtagccc tgcgagccct caggaaaccc ggcaacacga aagcaaacca     300
gatgagtgga ggctttcttc cagtgctgat gccaatggaa atgcccagcc ctcttcactc     360
gctgccaagg gctacagaag tgtgcatccc aaccttcctt ctgacaagtc ccaggattcc     420
agtcctctac taaatgaagt ttcttcttcc cttattggaa ctgattccca agcctttcca     480
tcagttagca agccttcatc cgcctatccc tccacaacga ttgtcaatcc tactattgtg     540
ctcttgcaac acaatcgaga acagcaaaaa cgactcagta gcctttcaga tcctgtctca     600
gaaagaagag tgggagagca ggactcagca ccaacccagg aaaaacccac ctcacctggc     660
```

```
aaggctattg aaaaaagagc aaaggatgac agtaggcggg tggtgaagag cactcaggac      720
ttaagcgatg tttccatgga tgaagtgggc atcccactcc ggaacactga gagatcaaaa      780
gactggtaca agactatgtt taaacagatc cacaaactga acagagacac tcctgaagaa      840
aacccttatt tccctacgta caaattccct gaacttcctg aaatccagca aacttccgaa      900
gaggacaatc cttacactcc cacctaccag tttcctgcat ctactcctag tcctaaatct      960
gaagatgatg attcagatct gtactctccc agatactcat tttctgaaga cacaaaatct     1020 ccccttctg tgcctcgctc aaaaagtgag atgagctaca ttgatggtga aggtagtc        1080 aagaggtcgg ccacactacc cctcccagcc cgctcttcct cactgaagtc aagctcagaa     1140
agaaatgact gggaaccccc agataagaaa gtagacacaa gaaaatatcg tgcagagccc     1200
aagagcattt acgaatatca gcctggcaag tcttccgttc tgaccaacga aaagatgagt     1260
cgggatataa gcccagaaga gatagattta agaatgaac cttggtataa attcttttcg      1320
gaattggagt ttgggaaacc gagctcagcc atcagcccta ctccggaaat ttcttcagag     1380
actcctggat atatatattc ttccaacttc catgcagtga gagggaatc agacggggct      1440 cctggggatc tcactagctt ggagaatgag agacaaattt ataaaagtgt cttggaaggt     1500
ggtgacatcc ctcttcaggg cctgagtggg ctcaagcgac catccagctc tgcttccact     1560
aaagattcag aatcgccaag acattttata ccagctgatt acttggaatc cacggaagaa     1620
tttattcgaa gacgtcatga tgataaagag aaacttttag cggaccagag acgacttaaa     1680
cgcgagcaag aagaggctga tattgcagct cgacgccaca caggcgtcat tccgacgcac     1740
catcagttta tcactaatga gcgctttggg gacctcctca atatagacga tactgcaaaa     1800
aggaaatctg ggtcagagat gagacctgcc agagccaaat ttgactttaa agctcagaca     1860
ctgaaggagc ttcctctgca gaaggagat attgtttaca tttataagca aattgatcag      1920
aactggtatg aaggagaaca ccacggccgg gtgggaatct tcccacgcac ctacatcgag     1980
cttcttcctc ctgctgagaa ggcacagccc aaaaagttga caccagtgca ggttttggaa     2040
tatggagaag ctattgctaa gtttaacttt aatggtgata cacaagtaga aatgtccttc     2100
agaaagggtg agaggatcac actgctccgg caggtagatg agaactggta cgaagggagg     2160
atcccgggga catcccgaca aggcatcttc cccatcacct acgtggatgt gatcaagcga     2220
ccactggtga aaaccctgt ggattacatg gacctgcctt tctcctcctc cccaagtcgc      2280
agtgccactg caagcccaca gcaacctcaa gcccagcagc gaagagtcac ccccgacagg     2340 agtcaaaccct cacaagattt atttagctat caagcattat atagctatat accacagaat     2400
gatgatgagt tggaactccg cgatggagat atcgttgatg tcatggaaaa atgtgacgat     2460 ggatggttg ttggtacttc aagaaggaca agcagtttg gtactttcc aggcaactat       2520 gtaaaacctt tgtatctata agaagactga aaaccatgga gattattttt attggaggag     2580
gaagcatcat tcatgaaccg atcttttag ttgagtcagt aggaaaatta atacagtgga      2640
taaagtaaga agcaaaagac agggacagag aagtgttgtg tttaaaaccc aagcctgtct     2700
aaggttactg tgtattagac agggccgaac tagtgtgctg agcaaaaaga attgaagcaa     2760
attgtattta ctt                                                        2773
```

<210> SEQ ID NO 3
<211> LENGTH: 684
<212> TYPE: PRT
<213> ORGANISM: Homo sapiens

<400> SEQUENCE: 3

```
Met Ser Ser Glu Cys Asp Gly Gly Ser Lys Ala Val Met Asn Gly Leu
1               5                   10                  15

Ala Pro Gly Ser Asn Gly Gln Asp Lys Asp Met Asp Pro Thr Lys Ile
                20                  25                  30

Cys Thr Gly Lys Gly Ala Val Thr Leu Arg Ala Ser Ser Ser Tyr Arg
            35                  40                  45

Glu Thr Pro Ser Ser Ser Pro Ala Ser Pro Gln Glu Thr Arg Gln His
        50                  55                  60

Glu Ser Lys Pro Asp Glu Trp Arg Leu Ser Ser Ser Ala Asp Ala Asn
65                  70                  75                  80

Gly Asn Ala Gln Pro Ser Ser Leu Ala Ala Lys Gly Tyr Arg Ser Val
                85                  90                  95

His Pro Asn Leu Pro Ser Asp Lys Ser Gln Asp Ser Ser Pro Leu Leu
            100                 105                 110

Asn Glu Val Ser Ser Ser Leu Ile Gly Thr Asp Ser Gln Ala Phe Pro
        115                 120                 125

Ser Val Ser Lys Pro Ser Ser Ala Tyr Pro Ser Thr Thr Ile Val Asn
        130                 135                 140

Pro Thr Ile Val Leu Leu Gln His Asn Arg Glu Gln Gln Lys Arg Leu
145                 150                 155                 160

Ser Ser Leu Ser Asp Pro Val Ser Glu Arg Arg Val Gly Glu Gln Asp
                165                 170                 175

Ser Ala Pro Thr Gln Glu Lys Pro Thr Ser Pro Gly Lys Ala Ile Glu
            180                 185                 190

Lys Arg Ala Lys Asp Asp Ser Arg Arg Val Val Lys Ser Thr Gln Asp
        195                 200                 205

Leu Ser Asp Val Ser Met Asp Glu Val Gly Ile Pro Leu Arg Asn Thr
210                 215                 220

Glu Arg Ser Lys Asp Trp Tyr Lys Thr Met Phe Lys Gln Ile His Lys
225                 230                 235                 240

Leu Asn Arg Asp Asp Asp Ser Asp Leu Tyr Ser Pro Arg Tyr Ser Phe
                245                 250                 255

Ser Glu Asp Thr Lys Ser Pro Leu Ser Val Pro Arg Ser Lys Ser Glu
            260                 265                 270

Met Ser Tyr Ile Asp Gly Glu Lys Val Val Lys Arg Ser Ala Thr Leu
        275                 280                 285

Pro Leu Pro Ala Arg Ser Ser Leu Lys Ser Ser Ser Glu Arg Asn
290                 295                 300

Asp Trp Glu Pro Pro Asp Lys Lys Val Asp Thr Arg Lys Tyr Arg Ala
305                 310                 315                 320

Glu Pro Lys Ser Ile Tyr Glu Tyr Gln Pro Gly Lys Ser Ser Val Leu
                325                 330                 335

Thr Asn Glu Lys Met Ser Ser Ala Ile Ser Pro Thr Pro Glu Ile Ser
            340                 345                 350

Ser Glu Thr Pro Gly Tyr Ile Tyr Ser Ser Asn Phe His Ala Val Lys
        355                 360                 365

Arg Glu Ser Asp Gly Ala Pro Gly Asp Leu Thr Ser Leu Glu Asn Glu
370                 375                 380

Arg Gln Ile Tyr Lys Ser Val Leu Glu Gly Gly Asp Ile Pro Leu Gln
385                 390                 395                 400

Gly Leu Ser Gly Leu Lys Arg Pro Ser Ser Ala Ser Thr Lys Asp
                405                 410                 415

Ser Glu Ser Pro Arg His Phe Ile Pro Ala Asp Tyr Leu Glu Ser Thr
            420                 425                 430
```

Glu Glu Phe Ile Arg Arg Arg His Asp Asp Lys Glu Met Arg Pro Ala
            435                 440                 445

Arg Ala Lys Phe Asp Phe Lys Ala Gln Thr Leu Lys Glu Leu Pro Leu
        450                 455                 460

Gln Lys Gly Asp Ile Val Tyr Ile Tyr Lys Gln Ile Asp Gln Asn Trp
465                 470                 475                 480

Tyr Glu Gly Glu His His Gly Arg Val Gly Ile Phe Pro Arg Thr Tyr
                485                 490                 495

Ile Glu Leu Leu Pro Pro Ala Glu Lys Ala Gln Pro Lys Lys Leu Thr
                500                 505                 510

Pro Val Gln Val Leu Glu Tyr Gly Glu Ala Ile Ala Lys Phe Asn Phe
        515                 520                 525

Asn Gly Asp Thr Gln Val Glu Met Ser Phe Arg Lys Gly Glu Arg Ile
    530                 535                 540

Thr Leu Leu Arg Gln Val Asp Glu Asn Trp Tyr Glu Gly Arg Ile Pro
545                 550                 555                 560

Gly Thr Ser Arg Gln Gly Ile Phe Pro Ile Thr Tyr Val Asp Val Ile
                565                 570                 575

Lys Arg Pro Leu Val Lys Asn Pro Val Asp Tyr Met Asp Leu Pro Phe
                580                 585                 590

Ser Ser Ser Pro Ser Arg Ser Ala Thr Ala Ser Pro Gln Gln Pro Gln
        595                 600                 605

Ala Gln Gln Arg Arg Val Thr Pro Asp Arg Ser Gln Thr Ser Gln Asp
    610                 615                 620

Leu Phe Ser Tyr Gln Ala Leu Tyr Ser Tyr Ile Pro Gln Asn Asp Asp
625                 630                 635                 640

Glu Leu Glu Leu Arg Asp Gly Asp Ile Val Asp Val Met Glu Lys Cys
                645                 650                 655

Asp Asp Gly Trp Phe Val Gly Thr Ser Arg Arg Thr Lys Gln Phe Gly
                660                 665                 670

Thr Phe Pro Gly Asn Tyr Val Lys Pro Leu Tyr Leu
        675                 680

<210> SEQ ID NO 4
<211> LENGTH: 5402
<212> TYPE: DNA
<213> ORGANISM: Homo sapiens

<400> SEQUENCE: 4
agcagttcag agccccagtt gcagacgact tgtcctgcca ccaccatgag ttctgaatgt      60
gatggtggtt ccaaagctgt gatgaatggc ttggcacctg cagcaatggg caagacaaa     120 gacatggatc ctacaaaaat ctgcactggg aagggagcgg tgactctccg ggcctcgtct    180
tcctacaggg aaaccccaag cagtagccct gcgagccctc aggaaacccg gcaacacgaa    240
agcaaaccag atgagtggag gctttcttcc agtgctgatg ccaatggaaa tgcccagccc    300
tcttcactcg ctgccaaggg ctacagaagt gtgcatccca accttccttc tgacaagtcc    360
caggattcca gtcctctact aaatgaagtt cttcttcccc ttattggaac tgattcccaa    420 gccttttccat cagttagcaa gccttcatcc gcctatccct ccacaacgat tgtcaatcct    480
actattgtgc tcttgcaaca caatcgagaa cagcaaaaac gactcagtag cctttcagat    540
cctgtctcag aaagaagagt gggagagcag gactcagcac caaccaggga aaacccacc    600 tcacctggca aggctattga aaaagagca aaggatgaca gtaggcgggt ggtgaagagc    660
actcaggact taagcgatgt ttccatggat gaagtgggca tcccactccg gaacactgag    720

```
agatcaaaag actggtacaa gactatgttt aaacagatcc acaaactgaa cagagatgat    780
gattcagatc tgtactctcc cagatactca ttttctgaag acacaaaatc tcccctttct    840
gtgcctcgct caaaaagtga gatgagctac attgatggtg agaaggtagt caagaggtcg    900
gccacactac ccctcccagc ccgctcttcc tcactgaagt caagctcaga agaaatgac     960 tgggaacccc cagataagaa agtagacaca agaaaatatc gtgcagagcc caagagcatt   1020
tacgaatatc agcctggcaa gtcttccgtt ctgaccaacg aaaagatgag ctcagccatc   1080
agccctactc cggaaatttc ttcagagact cctggatata tatattcttc aacttccat    1140 gcagtgaaga gggaatcaga cggggctcct ggggatctca ctagcttgga gaatgagaga   1200
caaatttata aaagtgtctt ggaaggtggt gacatccctc ttcagggcct gagtgggctc   1260
aagcgaccat ccagctctgc ttccactaaa gattcagaat cgccaagaca tttatacca    1320 gctgattact tggaatccac ggaagaattt attcgaagac gtcatgatga taaagagatg   1380
agacctgcca gagccaaatt tgactttaaa gctcagacac taaaggagct tcctctgcag   1440
aagggagata ttgtttacat ttataagcaa attgatcaga actggtatga aggagaacac   1500
cacggccggg tgggaatctt cccacgcacc tacatcgagc ttcttcctcc tgctgagaag   1560
gcacagccca aaaagttgac accagtgcag gttttggaat atggagaagc tattgctaag   1620 tttaactttta atggtgatac acaagtagaa atgtccttca gaaagggtga gaggatcaca   1680
ctgctccggc aggtagatga gaactggtac gaagggagga tcccggggac atcccgacaa   1740
ggcatcttcc ccatcaccta cgtggatgtg atcaagcgac cactggtgaa aaaccctgtg   1800
gattacatgg acctgccttt ctcctcctcc ccaagtcgca gtgccactgc aagcccacag   1860
caacctcaag cccagcagcg aagagtcacc cccgacagga gtcaaacctc acaagattta   1920
tttagctatc aagcattata tagctatata ccacagaatg atgatgagtt ggaactccgc   1980
gatggagata tcgttgatgt catggaaaaa tgtgacgatg gatggtttgt tggtacttca   2040
agaaggacaa agcagtttgg tacttttcca ggcaactatg taaaacccttt gtatctataa   2100 gaagactgaa aaccatggag attattttta ttggaggagg aagcatcatt catgaaccga   2160
tctttttagt tgagtcagta ggaaaattaa tacagtggat aaagtaagaa gcaaaagaca   2220
gggacagaga agtgttgtgt ttaaaaccca agcctgtcta aggttactgt gtattagaca   2280
gggccgaact agtgtgctga gcaaaaagaa ttgaagcaaa ttgtatttac ttagccgctt   2340 ctggagcca cttcagcctt tcccctcccc tccacttctt gggtaatctg acctgaagca   2400
tagtccagga gcagagttag ccagaaatgc ctcctgctgc cccagcctta gagagctccc   2460
atctcaatca ttgagcctga aggcttcaag cccaagaatg caacaagacc cccagcctac   2520
atttctcagc tccctggag ccagctgatc ctgtaacgct gctggaggtc agtctgagct   2580
accaagactg tccctagaca aaggtggagt cccccacact gcccaagacc aaatccctca   2640
ctcaacctgc tgaggtgtgg atgggaaac agaggcaaaa ctgaggcacc tgatgcattc   2700
agcctgctgt gcagcagtgc cattgactgc cctgatgttc agagagaaac gcacacaagg   2760
tttgcccatg agaattgggg agcagatggc caagcagata ggttatgtct gttttctgag   2820
tgatgaagtc aggaagccct gtggctctgg aggccacttg tggttcattc ttttcccata   2880
tccttggctt ttagaaatgg ttaccttcag gacagtgcag ctgcatttat cagagcacta   2940 tgctaagtt ttcttttctg gcttgtgttt ttctgggaca gtttagaatt gggaggccta   3000
ttctcataga acaccaaaaa tgatgttcag tgattcattt aacatacacc aatgtactct   3060
ggctgctggg gggacaacca taagcaagac atgcccaggg tttgccgtgg ctccagatct   3120
```

```
actccctgta ggagttcaag gatcacacaa acggtagtaa ccagggttgt gaatctgagt    3180
acaccctggc aaggcttctc ttcagactga agcagcaatt ctgccactac cagcagcaac    3240
caggacgtct gttctttgtg ggggccagat cagaagagag aggcccctgt gacgcccggg    3300
ctgcttggtc acaactctgt ccaattcaag gatgtttatc ggcctctctt agatcctgag    3360
tgagacaaat acagaaatga cccattccct gcccaccaga aactcagagg tgattgggga    3420
gactgacaca ggaaaatgaa cttaatcaag agagactgtg atatgtgcta agaagggtgt    3480
gagggaggga gagtgaatt ttccctggag ggatcctaga aagcattgtc atattgccat    3540
ctccattagc tcacttttaa acaactaggg tgctggaaga acctttgtct gagggtagtt    3600
catagctgga aatacttgga atattttcca gagtctctaa actctcatct tcccccacag    3660
atacacatcc aagctcacaa ataggagtag caattctagg tggtagggtt gtgtacggaa    3720
cccctggctg tctgcatata tctcagaatt accccaggac cattgtccca aagtctagag    3780
tctttacagg taggcaaaat ttgttttcaa tgcctgtgcc tcagctgctg tcacaaatac    3840
ccatcttagg atcccatcag cttcccatcc cccaccagac agccacagta ccctcacttt    3900
ctccctattg ttctttcaaa tcctgttctc aggaaagaaa ctgccactaa ttcattcaca    3960
ctaaggtgta aatgattgat aataggaatg agttacctct tcccacagac atttgttttt    4020
aagtatgaca gagcagggcc ttaatcccaa gggaaaggt tatggaactg gaggggtga    4080
gctttctggg tagaaggaga cttcctgaat ttccttaaaa cccagtaaga gtaagacctg    4140
ttgttttgga aggtctgctc caccatctaa gagcactgtt ttttttttt tgttgttgtt    4200
gttgttttac ggtctctgag ggaatatagt aaaaatgcat atgcacgtgc aatttgcacg    4260
gcagcatttc accgattgtg gactgtattg gctaatgtgt ttcctggtct ttagatgcaa    4320
accattaata acactatctt atctcatagt tttttcaggg gtgcttcttg attagtaggg    4380
aattttgaac acctctttaa atacagctag aaaataaaac caatttgtaa agccacattt    4440
gcatatgatg ccagcctcac gcatttgtat atctccagaa attcaggtat gcctcaccaa    4500
tttgcccgtc tttaataaaa tcttgtgtta aaatttgcat cacgtcgcct tcctatgtat    4560
gacgaaacaa gaaacagaga tttccaattg ctcttttgtc ttcagacatt tagtaatata    4620
aagtacctat ttttatgctg aaatgtttat acaggtttat taatagcaag tgcaactaac    4680
tggcggcatg ccttgcaaca cattttgata tattagccat gcttccgggt aaaggcaagc    4740
cccaaactcc ttatcttttg cagtctctct gggatcagta aaagaaaaaa aaaataatgt    4800
gcttaagaag tgggactgta aatatgtata tttaactttg tatagcccat gtacctacct    4860
tgtatagaaa aataattta aaaatttgaa tggaaggggg taaggaagt catgaagttt    4920
ttttgcattt ttatttaaat gaaggaattc caaataactc acctacagat ttttagcaca    4980
aaaatagcca ttgtaaagtg ttaaaattta cgataagtat tctattgggg aggaaaggta    5040
actctgatct cagttacagt ttttttttcc ttttaattt cattattttg ggttttggt    5100
ttttgcagtc ctatttatct gcagtcgtat taagtcctat tgctagaata ggttactaca    5160
aaaaaggtta tattctgaaa gaaaaataac tgacattata tataaccaat taatttaaag    5220
tattgccatt taaattacac actgagagca tgtcctatgc agacatagat ttttctgttc    5280
atttattttt cttcattgca gtggattgat ttgataaata gatgtgttga attactacat    5340
ttgctgtaca tattatttaa taaactttat tcagaattgc gtggcaaaaa aaaaaaaaaa    5400
aa                                                                  5402
```

```
<210> SEQ ID NO 5
<211> LENGTH: 816
<212> TYPE: PRT
<213> ORGANISM: Homo sapiens

<400> SEQUENCE: 5

Met Ser Ser Glu Cys Asp Gly Gly Ser Lys Ala Val Met Asn Gly Leu
1               5                   10                  15

Ala Pro Gly Ser Asn Gly Gln Asp Lys Asp Met Asp Pro Thr Lys Ile
            20                  25                  30

Cys Thr Gly Lys Gly Ala Val Thr Leu Arg Ala Ser Ser Ser Tyr Arg
        35                  40                  45

Glu Thr Pro Ser Ser Ser Pro Ala Ser Pro Gln Glu Thr Arg Gln His
    50                  55                  60

Glu Ser Lys Pro Gly Leu Glu Pro Glu Pro Ser Ser Ala Asp Glu Trp
65                  70                  75                  80

Arg Leu Ser Ser Ser Ala Asp Ala Asn Gly Asn Ala Gln Pro Ser Ser
                85                  90                  95

Leu Ala Ala Lys Gly Tyr Arg Ser Val His Pro Asn Leu Pro Ser Asp
            100                 105                 110

Lys Ser Gln Asp Ala Thr Ser Ser Ala Ala Gln Pro Glu Val Ile
            115                 120                 125

Val Val Pro Leu Tyr Leu Val Asn Thr Asp Arg Gly Gln Glu Gly Thr
    130                 135                 140

Ala Arg Pro Pro Thr Pro Leu Gly Pro Leu Gly Cys Val Pro Thr Ile
145                 150                 155                 160

Pro Ala Thr Ala Ser Ala Ala Ser Pro Leu Thr Phe Pro Thr Leu Asp
                165                 170                 175

Asp Phe Ile Pro Pro His Leu Gln Arg Trp Pro His His Ser Gln Pro
            180                 185                 190

Ala Arg Ala Ser Gly Ser Phe Ala Pro Ile Ser Gln Thr Pro Pro Ser
            195                 200                 205

Phe Ser Pro Pro Pro Leu Val Pro Pro Ala Pro Glu Asp Leu Arg
    210                 215                 220

Arg Val Ser Glu Pro Asp Leu Thr Gly Ala Val Ser Ser Thr Asp Ser
225                 230                 235                 240

Ser Pro Leu Leu Asn Glu Val Ser Ser Ser Leu Ile Gly Thr Asp Ser
                245                 250                 255

Gln Ala Phe Pro Ser Val Ser Lys Pro Ser Ser Ala Tyr Pro Ser Thr
            260                 265                 270

Thr Ile Val Asn Pro Thr Ile Val Leu Leu Gln His Asn Arg Glu Gln
    275                 280                 285

Gln Lys Arg Leu Ser Ser Leu Ser Asp Pro Val Ser Glu Arg Arg Val
            290                 295                 300

Gly Glu Gln Asp Ser Ala Pro Thr Gln Glu Lys Pro Thr Ser Pro Gly
305                 310                 315                 320

Lys Ala Ile Glu Lys Arg Ala Lys Asp Ser Arg Arg Val Val Lys
                325                 330                 335

Ser Thr Gln Asp Leu Ser Asp Val Ser Met Asp Glu Val Gly Ile Pro
            340                 345                 350

Leu Arg Asn Thr Glu Arg Ser Lys Asp Trp Tyr Lys Thr Met Phe Lys
            355                 360                 365

Gln Ile His Lys Leu Asn Arg Asp Asp Ser Asp Leu Tyr Ser Pro
    370                 375                 380

Arg Tyr Ser Phe Ser Glu Asp Thr Lys Ser Pro Leu Ser Val Pro Arg
```

```
              385                 390                 395                 400
        Ser Lys Ser Glu Met Ser Tyr Ile Asp Gly Glu Lys Val Val Lys Arg
                        405                 410                 415
        Ser Ala Thr Leu Pro Leu Pro Ala Arg Ser Ser Leu Lys Ser Ser
                        420                 425                 430
        Ser Glu Arg Asn Asp Trp Glu Pro Asp Lys Lys Val Asp Thr Arg
                        435                 440                 445
        Lys Tyr Arg Ala Glu Pro Lys Ser Ile Tyr Glu Tyr Gln Pro Gly Lys
                        450                 455                 460
        Ser Ser Val Leu Thr Asn Glu Lys Met Ser Ser Ala Ile Ser Pro Thr
        465                 470                 475                 480
        Pro Glu Ile Ser Ser Glu Thr Pro Gly Tyr Ile Tyr Ser Ser Asn Phe
                        485                 490                 495
        His Ala Val Lys Arg Glu Ser Asp Gly Ala Pro Gly Asp Leu Thr Ser
                        500                 505                 510
        Leu Glu Asn Glu Arg Gln Ile Tyr Lys Ser Val Leu Glu Gly Gly Asp
                        515                 520                 525
        Ile Pro Leu Gln Gly Leu Ser Gly Leu Lys Arg Pro Ser Ser Ser Ala
                        530                 535                 540
        Ser Thr Lys Asp Ser Glu Ser Pro Arg His Phe Ile Pro Ala Asp Tyr
        545                 550                 555                 560
        Leu Glu Ser Thr Glu Glu Phe Ile Arg Arg Arg His Asp Asp Lys Glu
                        565                 570                 575
        Met Arg Pro Ala Arg Ala Lys Phe Asp Phe Lys Ala Gln Thr Leu Lys
                        580                 585                 590
        Glu Leu Pro Leu Gln Lys Gly Asp Ile Val Tyr Ile Tyr Lys Gln Ile
                        595                 600                 605
        Asp Gln Asn Trp Tyr Glu Gly Glu His His Gly Arg Val Gly Ile Phe
                        610                 615                 620
        Pro Arg Thr Tyr Ile Glu Leu Leu Pro Pro Ala Glu Lys Ala Gln Pro
        625                 630                 635                 640
        Lys Lys Leu Thr Pro Val Gln Val Leu Glu Tyr Gly Glu Ala Ile Ala
                        645                 650                 655
        Lys Phe Asn Phe Asn Gly Asp Thr Gln Val Glu Met Ser Phe Arg Lys
                        660                 665                 670
        Gly Glu Arg Ile Thr Leu Leu Arg Gln Val Asp Glu Asn Trp Tyr Glu
                        675                 680                 685
        Gly Arg Ile Pro Gly Thr Ser Arg Gln Gly Ile Phe Pro Ile Thr Tyr
                        690                 695                 700
        Val Asp Val Ile Lys Arg Pro Leu Val Lys Asn Pro Val Asp Tyr Met
        705                 710                 715                 720
        Asp Leu Pro Phe Ser Ser Ser Pro Ser Arg Ser Ala Thr Ala Ser Pro
                        725                 730                 735
        Gln Gln Pro Gln Ala Gln Arg Arg Val Thr Pro Asp Arg Ser Gln
                        740                 745                 750
        Thr Ser Gln Asp Leu Phe Ser Tyr Gln Ala Leu Tyr Ser Tyr Ile Pro
                        755                 760                 765
        Gln Asn Asp Asp Glu Leu Glu Leu Arg Asp Gly Asp Ile Val Asp Val
                        770                 775                 780
        Met Glu Lys Cys Asp Asp Gly Trp Phe Val Gly Thr Ser Arg Arg Thr
        785                 790                 795                 800
        Lys Gln Phe Gly Thr Phe Pro Gly Asn Tyr Val Lys Pro Leu Tyr Leu
                        805                 810                 815
```

<210> SEQ ID NO 6
<211> LENGTH: 5979
<212> TYPE: DNA
<213> ORGANISM: Homo sapiens

<400> SEQUENCE: 6

| | | | | | |
|---|---|---|---|---|---|
| agcgctgagt | cccagaaaaa | cagagcgggg | ccagctgcag | cgtgtagtgc | gagtggggcg | 60 |
| gacgcgcgca | gcccgcccgc | ccggcgacca | gcaaggagtt | ggcatccttt | ggaagagttc | 120 |
| gtgaaagctt | tctgcccaga | gctcctggac | caatgcatct | tcccaccacc | ttaaaccact | 180 |
| gagcagttca | gagccccagt | tgcagacgac | ttgtcctgcc | accaccatga | gttctgaatg | 240 |
| tgatggtggt | tccaaagctg | tgatgaatgg | cttggcacct | ggcagcaatg | gcaagacaa | 300 |
| agacatggat | cctacaaaaa | tctgcactgg | gaagggagc | gtgactctcc | gggcctcgtc | 360 |
| ttcctacagg | gaaaccccaa | gcagtagccc | tgcgagccct | caggaaaccc | ggcaacacga | 420 |
| aagcaaacca | ggtctggagc | cagagccttc | ttcagcagat | gagtggaggc | tttcttccag | 480 |
| tgctgatgcc | aatggaaatg | cccagccctc | ttcactcgct | gccaagggct | acagaagtgt | 540 |
| gcatcccaac | cttccttctg | acaagtccca | ggatgccact | tcctccagtg | cagcccagcc | 600 |
| ggaggtaata | gttgtccctc | tctacctggt | taatactgac | agagggcaag | aaggcactgc | 660 |
| cagacctcca | cacctctggg | gcctcttgg | ctgcgtcccc | acaatcccag | cgactgcctc | 720 |
| tgccgcctca | cctctgacct | tcccgactct | agatgatttc | attccccctc | atctgcagag | 780 |
| gtggcccac | cacagccagc | cagcccgcgc | ctctggctcc | tttgccccca | ttagccagac | 840 |
| gccaccatcc | ttctcaccac | cacctccgct | ggtccctcct | gccccggagg | acctccgcag | 900 |
| agtctcggag | cctgacctca | cgggagctgt | ttcgagtacc | gattccagtc | ctctactaaa | 960 |
| tgaagtttct | tcttcccctta | ttggaactga | tcccaagcc | tttccatcag | ttagcaagcc | 1020 |
| ttcatccgcc | tatccctcca | caacgattgt | caatcctact | attgtgctct | tgcaacacaa | 1080 |
| tcgagaacag | caaaaacgac | tcagtagcct | ttcagatcct | gtctcagaaa | gaagagtggg | 1140 |
| agagcaggac | tcagcaccaa | cccaggaaaa | acccacctca | cctggcaagg | ctattgaaaa | 1200 |
| aagagcaaag | gatgacagta | ggcgggtggt | gaagagcact | caggacttaa | gcgatgtttc | 1260 |
| catggatgaa | gtgggcatcc | cactccggaa | cactgagaga | tcaaaagact | ggtacaagac | 1320 |
| tatgtttaaa | cagatccaca | aactgaacag | agatgatgat | tcagatctgt | actctcccag | 1380 |
| atactcattt | tctgaagaca | caaaatctcc | cctttctgtg | cctcgctcaa | aaagtgagat | 1440 |
| gagctacatt | gatggtgaga | aggtagtcaa | gaggtcggcc | acactacccc | tcccagcccg | 1500 |
| ctcttcctca | ctgaagtcaa | gctcagaaag | aaatgactgg | gaaccccag | ataagaaagt | 1560 |
| agacacaaga | aaatatcgtg | cagagcccaa | gagcatttac | gaatatcagc | ctggcaagtc | 1620 |
| ttccgttctg | accaacgaaa | agatgagctc | agccatcagc | cctactccgg | aaatttcttc | 1680 |
| agagactcct | ggatatatat | attcttccaa | cttccatgca | gtgaagaggg | aatcagacgg | 1740 |
| ggctcctggg | gatctcacta | gcttggagaa | tgagagacaa | atttataaaa | gtgtcttgga | 1800 |
| aggtggtgac | atccctcttc | agggcctgag | tgggctcaag | cgaccatcca | gctctgcttc | 1860 |
| cactaaagat | tcagaatcgc | caagacattt | taccagct | gattacttgg | aatccacgga | 1920 |
| agaatttatt | cgaagacgtc | atgatgataa | agagatgaga | cctgccagag | ccaaatttga | 1980 |
| ctttaaagct | cagacactaa | aggagcttcc | tctgcagaag | ggagatattg | tttacattta | 2040 |
| taagcaaatt | gatcagaact | ggtatgaagg | agaacaccac | ggccgggtgg | gaatcttccc | 2100 |
| acgcacctac | atcgagcttc | ttcctcctgc | tgagaaggca | cagcccaaaa | agttgacacc | 2160 |

```
agtgcaggtt ttggaatatg gagaagctat tgctaagttt aactttaatg gtgatacaca    2220
agtagaaatg tccttcagaa agggtgagag gatcacactg ctccggcagg tagatgagaa    2280
ctggtacgaa gggaggatcc cggggacatc cgacaaggc atcttcccca tcacctacgt     2340
ggatgtgatc aagcgaccac tggtgaaaaa ccctgtggat tacatggacc tgcctttctc    2400
ctcctcccca gtcgcagtg ccactgcaag cccacagcaa cctcaagccc agcagcgaag     2460
agtcaccccc gacaggagtc aaacctcaca agatttattt agctatcaag cattatatag    2520
ctatatacca cagaatgatg atgagttgga actccgcgat ggagatatcg ttgatgtcat    2580
ggaaaaatgt gacgatggat ggtttgttgg tacttcaaga aggacaaagc agtttggtac    2640
ttttccaggc aactatgtaa aacctttgta tctataagaa gactgaaaac catggagatt    2700 attttattg gaggaggaag catcattcat gaaccgatct ttttagttga gtcagtagga    2760
aaattaatac agtggataaa gtaagaagca aaagacaggg acagagaagt gttgtgttta    2820
aaacccaagc ctgtctaagg ttactgtgta ttagacaggg ccgaactagt gtgctgagca    2880 aaagaattg aagcaaattg tatttactta gccgcttctg ggagccactt cagcctttcc     2940
cctcccctcc acttcttggg taatctgacc tgaagcatag tccaggagca gagttagcca    3000
gaaatgcctc ctgctgcccc agccttagag agctcccatc tcaatcattg agcctgaagg    3060
cttcaagccc aagaatgcaa caagaccccc agcctacatt tctcagctcc cctggagcca    3120
gctgatcctg taacgctgct ggaggtcagt ctgagctacc aagactgtcc ctagacaaag    3180
gtggagtccc ccacactgcc caagaccaaa tccctcactc aacctgctga ggtgtggatg    3240
gggaaacaga ggcaaaactg aggcacctga tgcattcagc ctgctgtgca gcagtgccat    3300
tgactgccct gatgttcaga gagaaacgca cacaaggttt gcccatgaga attggggagc    3360
agatggccaa gcagataggt tatgtctgtt ttctgagtga tgaagtcagg aagccctgtg    3420
gctctggagg ccacttgtgg ttcattcttt tcccatatcc ttggctttta gaatggttta    3480
ccttcaggac agtgcagctg catttatcag agcactattg ctaagttttc ttttctggct    3540 tgtgttttc tgggacagtt tagaattggg aggcctattc tcatagaaca ccaaaaatga    3600
tgttcagtga ttcatttaac atacaccaat gtactctggc tgctgggggg acaaccataa    3660
gcaagacatg cccagggttt gccgtggctc cagatctact ccctgtagga gttcaaggat    3720
cacacaaacg gtagtaacca gggttgtgaa tctgagtaca ccctggcaag gcttctcttc    3780
agactgaagc agcaattctg ccactaccag cagcaaccag gacgtctgtt ctttgtgggg    3840
gccagatcag aagagagagg cccctgtgac gcccgggctg cttggtcaca actctgtcca    3900
attcaaggat gtttatcggc ctctcttaga tcctgagtga gacaaataca gaaatgaccc    3960
attccctgcc caccagaaac tcagaggtga ttggggagac tgacacagga aaatgaactt    4020
aatcaagaga gactgtgata tgtgctaaga agggtgtgag ggagggagag atgaattttc    4080
cctggaggga tcctagaaag cattgtcata ttgccatctc cattagctca cttttaaaca    4140
actagggtgc tggaagaacc tttgtctgag ggtagttcat agctggaaat acttggaata    4200
ttttccagag tctctaaact ctcatcttcc cccacagata cacatccaag ctcacaaata    4260
ggagtagcaa ttctaggtgg tagggttgtg tacggaaccc ctggctgtct gcatatatct    4320
cagaattacc ccaggaccat tgtcccaaag tctagagtct ttacaggtag gcaaaatttg    4380
ttttcaatgc ctgtgcctca gctgctgtca caaataccca tcttaggatc ccatcagctt    4440
cccatccccc accagacagc cacagtaccc tcactttctc cctattgttc tttcaaatcc    4500
tgttctcagg aaagaaactg ccactaattc attcacacta aggtgtaaat gattgataat    4560
```

-continued

```
aggaatgagt tacctcttcc cacagacatt tgttttttaag tatgacagag cagggcctta    4620
atcccaaggg aaaaggttat ggaactggag ggggtgagct ttctgggtag aaggagactt    4680
cctgaatttc cttaaaaccc agtaagagta agacctgttg ttttggaagg tctgctccac    4740
catctaaaag cactgttttt ttttttttgt tgttgttgtt gttttacggt ctctgaggga    4800
atatagtaaa aatgcatatg cacgtgcaat ttgcacggca gcatttcacc gattgtggac    4860
tgtattggct aatgtgtttc ctggtcttta gatgcaaacc attaataaca ctatcttatc    4920
tcatagtttt ttcaggggtg cttcttgatt agtagggaat tttgaacacc tcttttaaata    4980 cagctagaaa ataaaaccaa tttgtaaagc cacatttgca tatgatgcca gcctcacgca    5040
tttgtatatc tccagaaatt caggtatgcc tcaccaattt gcccgtcttt aataaaatct    5100
tgtgttaaaa tttgcatcac gtcgccttcc tatgtatgac gaaacaagaa acagagattt    5160
ccaattgctc ttttgtcttc agacatttag taatataaag tacctatttt tatgctgaaa    5220
tgtttataca ggtttattaa tagcaagtgc aactaactgg cggcatgcct tgcaacacat    5280
tttgatatat tagccatgct tccgggtaaa ggcaagcccc aaactcctta tcttttgcag    5340
tctctctggg atcagtaaaa gaaaaaaaaa ataatgtgct taagaagtgg gactgtaaat    5400
atgtatattt aactttgtat agcccatgta cctaccttgt atagaaaaat aattttaaaa    5460
atttgaatgg aaggggtaa aggaagtcat gaagttttttt tgcatttttta tttaaatgaa    5520 ggaattccaa ataactcacc tacagatttt tagcacaaaa atagccattg taaagtgtta    5580
aaatttacga taagtattct attggggagg aaaggtaact ctgatctcag ttacagtttt    5640
tttttccttt ttaatttcat tattttgggt ttttggtttt tgcagtccta tttatctgca    5700
gtcgtattaa gtcctattgc tagaataggt tactacaaaa aaggttatat tctgaaagaa    5760
aaataactga cattatatat aaccaattaa tttaaagtat tgccatttaa attacacact    5820
gagagcatgt cctatgcaga catagatttt tctgttcatt tattttttctt cattgcagtg    5880 gattgatttg ataaatagat gtgttgaatt actacatttg ctgtacatat tatttaataa    5940
actttattca gaattgcgtg gcaaaaaaaa aaaaaaaaa                           5979
```

<210> SEQ ID NO 7
<211> LENGTH: 1292
<212> TYPE: PRT
<213> ORGANISM: Homo sapiens

<400> SEQUENCE: 7

```
Met Ser Ser Glu Cys Asp Gly Gly Ser Lys Ala Val Met Asn Gly Leu
 1               5                  10                  15

Ala Pro Gly Ser Asn Gly Gln Asp Lys Ala Thr Ala Asp Pro Leu Arg
            20                  25                  30

Ala Arg Ser Ile Ser Ala Val Lys Ile Ile Pro Val Lys Thr Val Lys
        35                  40                  45

Asn Ala Ser Gly Leu Val Leu Pro Thr Asp Met Asp Pro Thr Lys Ile
    50                  55                  60

Cys Thr Gly Lys Gly Ala Val Thr Leu Arg Ala Ser Ser Ser Tyr Arg
65                  70                  75                  80

Glu Thr Pro Ser Ser Pro Ala Ser Pro Gln Glu Thr Arg Gln His
                85                  90                  95

Glu Ser Lys Pro Gly Leu Glu Pro Glu Pro Ser Ser Ala Asp Glu Trp
            100                 105                 110

Arg Leu Ser Ser Ser Ala Asp Ala Asn Gly Asn Ala Gln Pro Ser Ser
        115                 120                 125
```

-continued

```
Leu Ala Ala Lys Gly Tyr Arg Ser Val His Pro Asn Leu Pro Ser Asp
    130                 135                 140

Lys Ser Gln Asp Ala Thr Ser Ser Ala Ala Gln Pro Glu Val Ile
145                 150                 155                 160

Val Val Pro Leu Tyr Leu Val Asn Thr Asp Arg Gly Gln Glu Gly Thr
                165                 170                 175

Ala Arg Pro Pro Thr Pro Leu Gly Pro Leu Gly Cys Val Pro Thr Ile
            180                 185                 190

Pro Ala Thr Ala Ser Ala Ala Ser Pro Leu Thr Phe Pro Thr Leu Asp
        195                 200                 205

Asp Phe Ile Pro Pro His Leu Gln Arg Trp Pro His His Ser Gln Pro
    210                 215                 220

Ala Arg Ala Ser Gly Ser Phe Ala Pro Ile Ser Gln Thr Pro Pro Ser
225                 230                 235                 240

Phe Ser Pro Pro Pro Leu Val Pro Pro Ala Pro Glu Asp Leu Arg
                245                 250                 255

Arg Val Ser Glu Pro Asp Leu Thr Gly Ala Val Ser Ser Thr Asp Ser
            260                 265                 270

Ser Pro Leu Leu Asn Glu Val Ser Ser Leu Ile Gly Thr Asp Ser
        275                 280                 285

Gln Ala Phe Pro Ser Val Ser Lys Pro Ser Ser Ala Tyr Pro Ser Thr
    290                 295                 300

Thr Ile Val Asn Pro Thr Ile Val Leu Leu Gln His Asn Arg Glu Gln
305                 310                 315                 320

Gln Lys Arg Leu Ser Ser Leu Ser Asp Pro Val Ser Glu Arg Val
                325                 330                 335

Gly Glu Gln Asp Ser Ala Pro Thr Gln Glu Lys Pro Thr Ser Pro Gly
            340                 345                 350

Lys Ala Ile Glu Lys Arg Ala Lys Asp Asp Ser Arg Arg Val Val Lys
        355                 360                 365

Ser Thr Gln Asp Leu Ser Asp Val Ser Met Asp Glu Val Gly Ile Pro
    370                 375                 380

Leu Arg Asn Thr Glu Arg Ser Lys Asp Trp Tyr Lys Thr Met Phe Lys
385                 390                 395                 400

Gln Ile His Lys Leu Asn Arg Asp Thr Pro Glu Glu Asn Pro Tyr Phe
                405                 410                 415

Pro Thr Tyr Lys Phe Pro Glu Leu Pro Glu Ile Gln Gln Thr Ser Glu
            420                 425                 430

Glu Asp Asn Pro Tyr Thr Pro Thr Tyr Gln Phe Pro Ala Ser Thr Pro
        435                 440                 445

Ser Pro Lys Ser Glu Asp Asp Ser Asp Leu Tyr Ser Pro Arg Tyr
    450                 455                 460

Ser Phe Ser Glu Asp Thr Lys Ser Pro Leu Ser Val Pro Arg Ser Lys
465                 470                 475                 480

Ser Glu Met Ser Tyr Ile Asp Gly Glu Lys Val Val Lys Arg Ser Ala
                485                 490                 495

Thr Leu Pro Leu Pro Ala Arg Ser Ser Leu Lys Ser Ser Ser Glu
            500                 505                 510

Arg Asn Asp Trp Glu Pro Pro Asp Lys Lys Val Asp Thr Arg Lys Tyr
        515                 520                 525

Arg Ala Glu Pro Lys Ser Ile Tyr Glu Tyr Gln Pro Gly Lys Ser Ser
    530                 535                 540

Val Leu Thr Asn Glu Lys Met Ser Arg Asp Ile Ser Pro Glu Glu Ile
545                 550                 555                 560
```

```
Asp Leu Lys Asn Glu Pro Trp Tyr Lys Phe Ser Glu Leu Glu Phe
                565                 570                 575
Gly Lys Pro Pro Lys Lys Ile Trp Asp Tyr Thr Pro Gly Asp Cys
            580                 585                 590
Ser Ile Leu Pro Arg Glu Asp Arg Lys Thr Asn Leu Asp Lys Asp Leu
        595                 600                 605
Ser Leu Cys Gln Thr Glu Leu Glu Ala Asp Leu Glu Lys Met Glu Thr
    610                 615                 620
Leu Asn Lys Ala Pro Ser Ala Asn Val Pro Gln Ser Ser Ala Ile Ser
625                 630                 635                 640
Pro Thr Pro Glu Ile Ser Ser Glu Thr Pro Gly Tyr Ile Tyr Ser Ser
            645                 650                 655
Asn Phe His Ala Val Lys Arg Glu Ser Asp Gly Ala Pro Gly Asp Leu
        660                 665                 670
Thr Ser Leu Glu Asn Glu Arg Gln Ile Tyr Lys Ser Val Leu Glu Gly
    675                 680                 685
Gly Asp Ile Pro Leu Gln Gly Leu Ser Gly Leu Lys Arg Pro Ser Ser
690                 695                 700
Ser Ala Ser Thr Lys Asp Ser Glu Ser Pro Arg His Phe Ile Pro Ala
705                 710                 715                 720
Asp Tyr Leu Glu Ser Thr Glu Glu Phe Ile Arg Arg Arg His Asp Asp
            725                 730                 735
Lys Glu Lys Leu Leu Ala Asp Gln Arg Arg Leu Lys Arg Glu Gln Glu
        740                 745                 750
Glu Ala Asp Ile Ala Ala Arg Arg His Thr Gly Val Ile Pro Thr His
    755                 760                 765
His Gln Phe Ile Thr Asn Glu Arg Phe Gly Asp Leu Leu Asn Ile Asp
770                 775                 780
Asp Thr Ala Lys Arg Lys Ser Gly Ser Glu Met Arg Pro Ala Arg Ala
785                 790                 795                 800
Lys Phe Asp Phe Lys Ala Gln Thr Leu Lys Glu Leu Pro Leu Gln Lys
            805                 810                 815
Gly Asp Ile Val Tyr Ile Tyr Lys Gln Ile Asp Gln Asn Trp Tyr Glu
        820                 825                 830
Gly Glu His His Gly Arg Val Gly Ile Phe Pro Arg Thr Tyr Ile Glu
    835                 840                 845
Leu Leu Pro Pro Ala Glu Lys Ala Gln Pro Lys Lys Leu Thr Pro Val
850                 855                 860
Gln Val Leu Glu Tyr Gly Glu Ala Ile Ala Lys Phe Asn Phe Asn Gly
865                 870                 875                 880
Asp Thr Gln Val Glu Met Ser Phe Arg Lys Gly Glu Arg Ile Thr Leu
            885                 890                 895
Leu Arg Gln Val Asp Glu Asn Trp Tyr Glu Gly Arg Ile Pro Gly Thr
        900                 905                 910
Ser Arg Gln Gly Ile Phe Pro Ile Thr Tyr Val Asp Val Ile Lys Arg
    915                 920                 925
Pro Leu Val Lys Asn Pro Val Asp Tyr Met Asp Leu Pro Phe Ser Ser
930                 935                 940
Ser Pro Ser Arg Ser Ala Thr Ala Ser Pro Gln Phe Ser Ser His Ser
945                 950                 955                 960
Lys Leu Ile Thr Pro Ala Pro Ser Ser Leu Pro His Ser Arg Arg Ala
            965                 970                 975
Leu Ser Pro Glu Met His Ala Val Thr Ser Glu Trp Ile Ser Leu Thr
```

```
                980             985             990
Val Gly Val Pro Gly Arg Arg Ser Leu Ala Leu Thr Pro Pro Leu Pro
                    995             1000            1005

Pro Leu Pro Glu Ala Ser Ile Tyr Asn Thr Asp His Leu Ala Leu
    1010            1015            1020

Ser Pro Arg Ala Ser Pro Ser Leu Ser Leu Ser Leu Pro His Leu
    1025            1030            1035

Ser Trp Ser Asp Arg Pro Thr Pro Arg Ser Val Ala Ser Pro Leu
    1040            1045            1050

Ala Leu Pro Ser Pro His Lys Thr Tyr Ser Leu Ala Pro Thr Ser
    1055            1060            1065

Gln Ala Ser Leu His Met Asn Gly Asp Gly Val His Thr Pro
    1070            1075            1080

Ser Ser Gly Ile His Gln Asp Ser Phe Leu Gln Leu Pro Leu Gly
    1085            1090            1095

Ser Ser Asp Ser Val Ile Ser Gln Leu Ser Asp Ala Phe Ser Ser
    1100            1105            1110

Gln Ser Lys Arg Gln Pro Trp Arg Glu Glu Ser Gly Gln Tyr Glu
    1115            1120            1125

Arg Lys Ala Glu Arg Gly Ala Gly Glu Arg Gly Pro Gly Gly Pro
    1130            1135            1140

Lys Ile Ser Lys Lys Ser Cys Leu Lys Pro Ser Asp Val Val Arg
    1145            1150            1155

Cys Leu Ser Thr Glu Gln Arg Leu Ser Asp Leu Asn Thr Pro Glu
    1160            1165            1170

Glu Ser Arg Pro Gly Lys Pro Leu Gly Ser Ala Phe Pro Gly Ser
    1175            1180            1185

Glu Ala Glu Gln Thr Glu Arg His Arg Gly Gly Glu Gln Ala Gly
    1190            1195            1200

Arg Lys Ala Ala Arg Arg Gly Gly Ser Gln Gln Pro Gln Ala Gln
    1205            1210            1215

Gln Arg Arg Val Thr Pro Asp Arg Ser Gln Thr Ser Gln Asp Leu
    1220            1225            1230

Phe Ser Tyr Gln Ala Leu Tyr Ser Tyr Ile Pro Gln Asn Asp Asp
    1235            1240            1245

Glu Leu Glu Leu Arg Asp Gly Asp Ile Val Asp Val Met Glu Lys
    1250            1255            1260

Cys Asp Asp Gly Trp Phe Val Gly Thr Ser Arg Arg Thr Lys Gln
    1265            1270            1275

Phe Gly Thr Phe Pro Gly Asn Tyr Val Lys Pro Leu Tyr Leu
    1280            1285            1290

<210> SEQ ID NO 8
<211> LENGTH: 7226
<212> TYPE: DNA
<213> ORGANISM: Homo sapiens

<400> SEQUENCE: 8
agcagttcag agccccagtt gcagacgact tgtcctgcca ccaccatgag ttctgaatgt      60
gatggtggtt ccaaagctgt gatgaatggc ttggcacctg gcagcaatgg caagacaaa     120 gcaactgccg acccttacg cgcacgctct atttctgctg ttaaaatcat tcctgtgaag     180
acagtgaaaa acgcctcagg cctagttctc cctacagaca tggatcctac aaaaatctgc     240
actgggaagg gagcggtgac tctccgggcc tcgtcttcct acaggaaaac cccaagcagt     300
```

```
agccctgcga gccctcagga aacccggcaa cacgaaagca aaccaggtct ggagccagag    360
ccttcttcag cagatgagtg gaggctttct tccagtgctg atgccaatgg aaatgcccag    420
ccctcttcac tcgctgccaa gggctacaga agtgtgcatc ccaaccttcc ttctgacaag    480
tcccaggatg ccacttcctc cagtgcagcc cagccgagg taatagttgt ccctctctac     540
ctggttaata ctgacagagg gcaagaaggc actgccagac ctccaacacc tctggggcct    600
cttggctgcg tccccacaat cccagcgact gcctctgccg cctcacctct gaccttcccg    660
actctagatg atttcattcc ccctcatctg cagaggtggc cccaccacag ccagccagcc    720
cgcgcctctg gctcctttgc ccccattagc cagacgccac catccttctc accaccacct    780
ccgctggtcc ctcctgcccc ggaggacctc cgcagagtct cggagcctga cctcacggga    840
gctgtttcga gtaccgattc cagtcctcta ctaaatgaag tttcttcttc ccttattgga    900
actgattccc aagcctttcc atcagttagc aagccttcat ccgcctatcc ctccacaacg    960
attgtcaatc ctactattgt gctcttgcaa cacaatcgag aacagcaaaa acgactcagt   1020
agcctttcag atcctgtctc agaaagaaga gtgggagagc aggactcagc accaacccag   1080
gaaaaaccca cctcacctgg caaggctatt gaaaaaagag caaaggatga cagtaggcgg   1140
gtggtgaaga gcactcagga cttaagcgat gtttccatgg atgaagtggg catcccactc   1200
cggaacactg agagatcaaa agactggtac aagactatgt ttaaacagat ccacaaactg   1260
aacagagaca ctcctgaaga aaacccttat ttccctacgt acaaattccc tgaacttcct   1320
gaaatccagc aaacttccga agaggacaat ccttacactc ccacctacca gtttcctgca   1380
tctactccta gtcctaaatc tgaagatgat gattcagatc tgtactctcc cagatactca   1440
ttttctgaag acacaaaatc tcccctttct gtgcctcgct caaaaagtga gatgagctac   1500
attgatggtg agaaggtagt caagaggtcg gccacactac ccctcccagc ccgctcttcc   1560
tcactgaagt caagctcaga agaaatgac tgggaacccc cagataagaa agtagacaca    1620
agaaaatatc gtgcagagcc caagagcatt tacgaatatc agcctggcaa gtcttccgtt   1680
ctgaccaacg aaaagatgag tcgggatata agcccagaag agatagattt aaagaatgaa   1740
ccttggtata aattcttttc ggaattggag tttgggaaac cgcctcccaa aaagatatgg   1800
gattatactc ctggagactg ctctatcctt cctagagagg atagaaagac taatctagac   1860
aaagatctca gcctctgcca gacagagtta gaggcagatt tagaaaaaat ggagacgctt   1920
aataaagcac ccagtgcaaa cgtgccacag agctcagcca tcagccctac tccggaaatt   1980
tcttcagaga ctcctggata tatatattct tccaacttcc atgcagtgaa gagggaatca   2040
gacggggctc ctggggatct cactagcttg gagaatgaga gacaaattta taaagtgtc    2100 ttggaaggtg gtgacatccc tcttcagggc ctgagtgggc tcaagcgacc atccagctct   2160
gcttccacta aagattcaga atcgccaaga cattttatac cagctgatta cttggaatcc   2220
acggaagaat ttattcgaag acgtcatgat gataaagaga aacttttagc ggaccagaga   2280
cgacttaaac gcgagcaaga agaggctgat attgcagctc gacgccacac aggcgtcatt   2340
ccgacgcacc atcagtttat cactaatgag cgctttgggg acctcctcaa tatagacgat   2400
actgcaaaaa ggaaatctgg gtcagagatg agacctgcca gagccaaatt tgactttaaa   2460
gctcagacac taaggagct tcctctgcag aaggagata ttgtttacat ttataagcaa     2520
attgatcaga actggtatga aggagaacac cacggccggg tgggaatctt cccacgcacc   2580
tacatcgagc ttcttcctcc tgctgagaag gcacagccca aaaagttgac accagtgcag   2640
gttttggaat atggagaagc tattgctaag tttaacttta atggtgatac acaagtagaa   2700
```

```
atgtccttca gaaagggtga gaggatcaca ctgctccggc aggtagatga gaactggtac   2760
gaagggagga tcccgggac atcccgacaa ggcatcttcc ccatcaccta cgtggatgtg   2820
atcaagcgac cactggtgaa aaaccctgtg gattacatgg acctgccttt ctcctcctcc   2880
ccaagtcgca gtgccactgc aagcccacag ttttccagtc acagcaagct catcacgcca   2940 gcccctcat ctctgcccca ctcccgccga gccctgtccc ccgagatgca cgctgtcacc   3000
tctgagtgga tctcactgac tgtgggggtc ccaggcaggc gttctctggc cctgacccca   3060
cccttgcctc ctctgccaga ggcttctatc tataacactg accacctcgc cttgtcacca   3120
agggccagtc cctccctgtc tctcagcctc ccccatttga gttggtcaga tcgtcccacc   3180
ccacgatcag tagcttctcc actggcccta ccttcccac acaaaaccta ctccctagca   3240
cctacttccc aggcctccct tcacatgaat ggagacggtg tgtccacac gccatcttca   3300 ggcatccacc aagatagctt cttgcagctg ccgctgggga gctctgatag tgtcatctcc   3360
cagcttagtg atgcctttag cagccagagc aagaggcagc catggcgcga agagagtgga   3420
caatatgaga ggaaagcaga gagggggca ggcgaaagag gccctggtgg acccaagatc   3480
tctaagaaga gctgcttgaa gccttcgac gtggtcaggt gcctgagtac tgaacagaga   3540
ctctcagatc tcaacacccc tgaggagagc cggcccggca agccctggg tagcgctttt   3600 ccaggaagtg aggctgagca gacagagcgg catagaggtg gcgagcaggc ggggaggaaa   3660
gctgctcgga gaggtgggag ccagcaacct caagcccagc agcgaagagt cacccccgac   3720
aggagtcaaa cctcacaaga tttatttagc tatcaagcat tatatagcta tataccacag   3780
aatgatgatg agttggaact ccgcgatgga gatatcgttg atgtcatgga aaaatgtgac   3840
gatggatggt tgttggtac ttcaagaagg acaaagcagt ttggtacttt tccaggcaac   3900
tatgtaaaac ctttgtatct ataagaagac tgaaaaccat ggagattatt tttattggag   3960
gaggaagcat cattcatgaa ccgatctttt tagttgagtc agtaggaaaa ttaatacagt   4020
ggataaagta agaagcaaaa gacagggaca gagagtgtt gtgtttaaaa cccaagcctg   4080
tctaaggtta ctgtgtatta gacagggccg aactagtgtg ctgagcaaaa agaattgaag   4140
caaattgtat ttacttagcc gcttctggga gccacttcag cctttcccct ccctccact   4200 tcttgggtaa tctgacctga agcatagtcc aggagcagag ttagccagaa atgcctcctg   4260
ctgccccagc cttagagagc tcccatctca atcattgagc ctgaaggctt caagcccaag   4320
aatgcaacaa gaccccccagc ctacatttct cagctcccct ggagccagct gatcctgtaa   4380
cgctgctgga ggtcagtctg agctaccaag actgtcccta gacaaaggtg gagtccccca   4440
cactgcccaa gaccaaatcc ctcactcaac ctgctgaggt gtggatgggg aaacagaggc   4500
aaaactgagg cacctgatgc attcagcctg ctgtgcagca gtgccattga ctgccctgat   4560
gttcagagag aaacgcacac aaggtttgcc catgagaatt ggggagcaga tggccaagca   4620
gataggttat gtctgttttc tgagtgatga agtcaggaag ccctgtggct ctggaggcca   4680
cttgtggttc attcttttcc catatccttg gcttttagaa atggttacct tcaggacagt   4740
gcagctgcat ttatcagagc actattgcta agttttcttt tctggcttgt gtttttctgg   4800
gacagtttag aattgggagg cctattctca tagaacacca aaaatgatgt tcagtgattc   4860
atttaacata caccaatgta ctctggctgc tggggggaca accataagca agacatgccc   4920
agggtttgcc gtggctccag atctactccc tgtaggagtt caaggatcac acaaacggta   4980
gtaaccaggg ttgtgaatct gagtacaccc tggcaaggct tctcttcaga ctgaagcagc   5040
aattctgcca ctaccagcag caaccaggac gtctgttctt tgtgggggcc agatcagaag   5100
```

| | |
|---|---|
| agagaggccc ctgtgacgcc cgggctgctt ggtcacaact ctgtccaatt caaggatgtt | 5160 |
| tatcggcctc tcttagatcc tgagtgagac aaatacagaa atgacccatt ccctgcccac | 5220 |
| cagaaactca gaggtgattg gggagactga cacaggaaaa tgaacttaat caagagagac | 5280 |
| tgtgatatgt gctaagaagg gtgtgaggga gggagagatg aatttccct ggagggatcc | 5340 |
| tagaaagcat tgtcatattg ccatctccat tagctcactt ttaaacaact agggtgctgg | 5400 |
| aagaaccttt gtctgagggt agttcatagc tggaaatact tggaatattt tccagagtct | 5460 |
| ctaaactctc atcttccccc acagatacac atccaagctc acaaatagga gtagcaattc | 5520 |
| taggtggtag ggttgtgtac ggaaccctg gctgtctgca tatatctcag aattacccca | 5580 |
| ggaccattgt cccaaagtct agagtcttta caggtaggca aaatttgttt tcaatgcctg | 5640 |
| tgcctcagct gctgtcacaa atacccatct taggatccca tcagcttccc atcccccacc | 5700 |
| agacagccac agtaccctca cttctccct attgttcttt caaatcctgt tctcaggaaa | 5760 |
| gaaactgcca ctaattcatt cacactaagg tgtaaatgat tgataatagg aatgagttac | 5820 |
| ctcttcccac agacatttgt ttttaagtat gacagagcag ggccttaatc ccaagggaaa | 5880 |
| aggttatgga actggagggg gtgagctttc tgggtagaag gagacttcct gaatttcctt | 5940 |
| aaaacccagt aagagtaaga cctgttgttt tggaaggtct gctccaccat ctaagagcac | 6000 |
| tgtttttttt tttttgttgt tgttgttgtt ttacggtctc tgagggaata tagtaaaaat | 6060 |
| gcatatgcac gtgcaatttg cacggcagca tttcaccgat tgtggactgt attggctaat | 6120 |
| gtgtttcctg gtctttagat gcaaaccatt aataacacta tcttatctca tagttttttc | 6180 |
| agggggtgctt cttgattagt agggaatttt gaacacctct ttaaatacag ctagaaaata | 6240 |
| aaaccaattt gtaaagccac atttgcatat gatgccagcc tcacgcattt gtatatctcc | 6300 |
| agaaattcag gtatgcctca ccaatttgcc cgtctttaat aaaatcttgt gttaaaattt | 6360 |
| gcatcacgtc gccttcctat gtatgacgaa acaagaaaca gagatttcca attgctcttt | 6420 |
| tgtcttcaga catttagtaa tataaagtac ctatttttat gctgaaatgt ttatacaggt | 6480 |
| ttattaatag caagtgcaac taactggcgg catgccttgc aacacatttt gatatattag | 6540 |
| ccatgcttcc gggtaaaggc aagccccaaa ctccttatct tttgcagtct ctctgggatc | 6600 |
| agtaaaagaa aaaaaaata atgtgcttaa gaagtgggac tgtaaatatg tatatttaac | 6660 |
| tttgtatagc ccatgtacct accttgtata gaaaaataat tttaaaaatt tgaatgaag | 6720 |
| ggggtaaagg aagtcatgaa gttttttgc attttattt aaatgaagga attccaaata | 6780 |
| actcacctac agattttag cacaaaaata gccattgtaa agtgttaaaa tttacgataa | 6840 |
| gtattctatt ggggaggaaa ggtaactctg atctcagtta cagttttttt ttcctttta | 6900 |
| atttcattat tttgggtttt tggttttgc agtcctattt atctgcagtc gtattaagtc | 6960 |
| ctattgctag aataggttac tacaaaaaag gttatattct gaaagaaaaa taactgacat | 7020 |
| tatatataac caattaattt aaagtattgc catttaaatt acacactgag agcatgtcct | 7080 |
| atgcagacat agattttct gttcatttat ttttcttcat tgcagtggat tgatttgata | 7140 |
| aatagatgtg ttgaattact acatttgctg tacatattat ttaataaact ttattcagaa | 7200 |
| ttgcgtggca aaaaaaaaaa aaaaaa | 7226 |

```
<210> SEQ ID NO 9
<211> LENGTH: 1151
<212> TYPE: PRT
<213> ORGANISM: Homo sapiens

<400> SEQUENCE: 9
```

-continued

```
Met Ser Ser Glu Cys Asp Gly Gly Ser Lys Ala Val Met Asn Gly Leu
1               5                   10                  15

Ala Pro Gly Ser Asn Gly Gln Asp Lys Ala Thr Ala Asp Pro Leu Arg
            20                  25                  30

Ala Arg Ser Ile Ser Ala Val Lys Ile Ile Pro Val Lys Thr Val Lys
        35                  40                  45

Asn Ala Ser Gly Leu Val Leu Pro Thr Asp Met Asp Pro Thr Lys Ile
    50                  55                  60

Cys Thr Gly Lys Gly Ala Val Thr Leu Arg Ala Ser Ser Ser Tyr Arg
65                  70                  75                  80

Glu Thr Pro Ser Ser Pro Ala Ser Pro Gln Glu Thr Arg Gln His
                85                  90                  95

Glu Ser Lys Pro Gly Leu Glu Pro Glu Pro Ser Ser Ala Asp Glu Trp
            100                 105                 110

Arg Leu Ser Ser Ser Ala Asp Ala Asn Gly Asn Ala Gln Pro Ser Ser
        115                 120                 125

Leu Ala Ala Lys Gly Tyr Arg Ser Val His Pro Asn Leu Pro Ser Asp
    130                 135                 140

Lys Ser Gln Asp Ala Thr Ser Ser Ala Ala Gln Pro Glu Val Ile
145                 150                 155                 160

Val Val Pro Leu Tyr Leu Val Asn Thr Asp Arg Gly Gln Glu Gly Thr
                165                 170                 175

Ala Arg Pro Pro Thr Pro Leu Gly Pro Leu Gly Cys Val Pro Thr Ile
            180                 185                 190

Pro Ala Thr Ala Ser Ala Ala Ser Pro Leu Thr Phe Pro Thr Leu Asp
        195                 200                 205

Asp Phe Ile Pro Pro His Leu Gln Arg Trp Pro His His Ser Gln Pro
    210                 215                 220

Ala Arg Ala Ser Gly Ser Phe Ala Pro Ile Ser Gln Thr Pro Pro Ser
225                 230                 235                 240

Phe Ser Pro Pro Pro Leu Val Pro Pro Ala Pro Glu Asp Leu Arg
                245                 250                 255

Arg Val Ser Glu Pro Asp Leu Thr Gly Ala Val Ser Ser Thr Asp Ser
            260                 265                 270

Ser Pro Leu Leu Asn Glu Val Ser Ser Leu Ile Gly Thr Asp Ser
        275                 280                 285

Gln Ala Phe Pro Ser Val Ser Lys Pro Ser Ser Ala Tyr Pro Ser Thr
    290                 295                 300

Thr Ile Val Asn Pro Thr Ile Val Leu Leu Gln His Asn Arg Glu Gln
305                 310                 315                 320

Gln Lys Arg Leu Ser Ser Leu Ser Asp Pro Val Ser Glu Arg Arg Val
                325                 330                 335

Gly Glu Gln Asp Ser Ala Pro Thr Gln Glu Lys Pro Thr Ser Pro Gly
            340                 345                 350

Lys Ala Ile Glu Lys Arg Ala Lys Asp Asp Ser Arg Arg Val Val Lys
        355                 360                 365

Ser Thr Gln Asp Leu Ser Asp Val Ser Met Asp Glu Val Gly Ile Pro
    370                 375                 380

Leu Arg Asn Thr Glu Arg Ser Lys Asp Trp Tyr Lys Thr Met Phe Lys
385                 390                 395                 400

Gln Ile His Lys Leu Asn Arg Asp Thr Pro Glu Glu Asn Pro Tyr Phe
                405                 410                 415

Pro Thr Tyr Lys Phe Pro Glu Leu Pro Glu Ile Gln Gln Thr Ser Glu
            420                 425                 430
```

```
Glu Thr Lys Ser Cys Ser Val Met Ser Pro Arg Leu Glu Cys Ser Gly
        435                 440                 445

Thr Val Ile Ala His Cys Ser Leu Lys Leu Leu Asp Ser Ser Asn Pro
    450                 455                 460

Pro Thr Ser Ala Ser Gln Val Ala Gly Thr Ala Asp Asp Ser Asp
465                 470                 475                 480

Leu Tyr Ser Pro Arg Tyr Ser Phe Ser Glu Asp Thr Lys Ser Pro Leu
                485                 490                 495

Ser Val Pro Arg Ser Lys Ser Glu Met Ser Tyr Ile Asp Gly Glu Lys
            500                 505                 510

Val Val Lys Arg Ser Ala Thr Leu Pro Leu Pro Ala Arg Ser Ser Ser
            515                 520                 525

Leu Lys Ser Ser Ser Glu Arg Asn Asp Trp Glu Pro Pro Asp Lys Lys
        530                 535                 540

Val Asp Thr Arg Lys Tyr Arg Ala Glu Pro Lys Ser Ile Tyr Glu Tyr
545                 550                 555                 560

Gln Pro Gly Lys Ser Ser Val Leu Thr Asn Glu Lys Met Ser Arg Asp
                565                 570                 575

Ile Ser Pro Glu Glu Ile Asp Leu Lys Asn Glu Pro Trp Tyr Lys Phe
            580                 585                 590

Phe Ser Glu Leu Glu Phe Gly Lys Pro Pro Lys Lys Ile Trp Asp
        595                 600                 605

Tyr Thr Pro Gly Asp Cys Ser Ile Leu Pro Arg Glu Asp Arg Lys Thr
610                 615                 620

Asn Leu Asp Lys Asp Leu Ser Leu Cys Gln Thr Glu Leu Glu Ala Asp
625                 630                 635                 640

Leu Glu Lys Met Glu Thr Leu Asn Lys Ala Pro Ser Ala Asn Val Pro
                645                 650                 655

Gln Ser Ser Ala Ile Ser Pro Thr Pro Glu Ile Ser Ser Glu Thr Pro
            660                 665                 670

Gly Tyr Ile Tyr Ser Ser Asn Phe His Ala Val Lys Arg Glu Ser Asp
                675                 680                 685

Gly Ala Pro Gly Asp Leu Thr Ser Leu Glu Asn Glu Arg Gln Ile Tyr
        690                 695                 700

Lys Ser Val Leu Glu Gly Gly Asp Ile Pro Leu Gln Gly Leu Ser Gly
705                 710                 715                 720

Leu Lys Arg Pro Ser Ser Ser Ala Ser Thr Lys Asp Ser Glu Ser Pro
                725                 730                 735

Arg His Phe Ile Pro Ala Asp Tyr Leu Glu Ser Thr Glu Glu Phe Ile
            740                 745                 750

Arg Arg Arg His Asp Asp Lys Glu Lys Leu Leu Ala Asp Gln Arg Arg
        755                 760                 765

Leu Lys Arg Glu Gln Glu Glu Ala Asp Ile Ala Ala Arg Arg His Thr
    770                 775                 780

Gly Val Ile Pro Thr His His Gln Phe Ile Thr Asn Glu Arg Phe Gly
785                 790                 795                 800

Asp Leu Leu Asn Ile Asp Asp Thr Ala Lys Arg Lys Ser Gly Ser Glu
                805                 810                 815

Met Arg Pro Ala Arg Ala Lys Phe Asp Phe Lys Ala Gln Thr Leu Lys
            820                 825                 830

Glu Leu Pro Leu Gln Lys Gly Asp Ile Val Tyr Ile Tyr Lys Gln Ile
        835                 840                 845

Asp Gln Asn Trp Tyr Glu Gly Glu His His Gly Arg Val Gly Ile Phe
```

```
                850                 855                 860
Pro Arg Thr Tyr Ile Glu Leu Leu Pro Pro Ala Glu Lys Ala Gln Pro
865                 870                 875                 880

Lys Lys Leu Thr Pro Val Gln Val Leu Glu Tyr Gly Glu Ala Ile Ala
                885                 890                 895

Lys Phe Asn Phe Asn Gly Asp Thr Gln Val Glu Met Ser Phe Arg Lys
                    900                 905                 910

Gly Glu Arg Ile Thr Leu Leu Arg Gln Val Asp Glu Asn Trp Tyr Glu
                915                 920                 925

Gly Arg Ile Pro Gly Thr Ser Arg Gln Gly Ile Phe Pro Ile Thr Tyr
        930                 935                 940

Val Asp Val Ile Lys Arg Pro Leu Val Lys Asn Pro Val Asp Tyr Met
945                 950                 955                 960

Asp Leu Pro Phe Ser Ser Ser Pro Ser Arg Ser Ala Thr Ala Ser Pro
                    965                 970                 975

Gln Pro Trp Arg Glu Glu Ser Gly Gln Tyr Glu Arg Lys Ala Glu Arg
            980                 985                 990

Gly Ala Gly Glu Arg Gly Pro Gly Gly Pro Lys Ile Ser Lys Lys Ser
                995                 1000                1005

Cys Leu Lys Pro Ser Asp Val Val Arg Cys Leu Ser Thr Glu Gln
    1010                1015                1020

Arg Leu Ser Asp Leu Asn Thr Pro Glu Ser Arg Pro Gly Lys
    1025                1030                1035

Pro Leu Gly Ser Ala Phe Pro Gly Ser Glu Ala Glu Gln Thr Glu
    1040                1045                1050

Arg His Arg Gly Gly Glu Gln Ala Gly Arg Lys Ala Ala Arg Arg
    1055                1060                1065

Gly Gly Ser Gln Gln Pro Gln Ala Gln Arg Arg Val Thr Pro
    1070                1075                1080

Asp Arg Ser Gln Thr Ser Gln Asp Leu Phe Ser Tyr Gln Ala Leu
    1085                1090                1095

Tyr Ser Tyr Ile Pro Gln Asn Asp Asp Glu Leu Glu Leu Arg Asp
    1100                1105                1110

Gly Asp Ile Val Asp Val Met Glu Lys Cys Asp Asp Gly Trp Phe
    1115                1120                1125

Val Gly Thr Ser Arg Arg Thr Lys Gln Phe Gly Thr Phe Pro Gly
    1130                1135                1140

Asn Tyr Val Lys Pro Leu Tyr Leu
    1145                1150

<210> SEQ ID NO 10
<211> LENGTH: 6803
<212> TYPE: DNA
<213> ORGANISM: Homo sapiens

<400> SEQUENCE: 10
agcagttcag agccccagtt gcagacgact tgtcctgcca ccaccatgag ttctgaatgt      60
gatggtggtt ccaaagctgt gatgaatggc ttggcacctg cagcaatggg caagacaaa     120 gcaactgccg acccttttacg cgcacgctct atttctgctg ttaaaatcat tcctgtgaag    180
acagtgaaaa acgcctcagg cctagttctc cctacagaca tggatcctac aaaaatctgc    240
actgggaagg gagcggtgac ctctccgggcc tcgtcttcct acagggaaac cccaagcagt   300
agccctgcga gccctcagga aacccggcaa cacgaaagca aaccaggtct ggagccagag    360
ccttcttcag cagatgagtg gaggctttct tccagtgctg atgccaatgg aaatgcccag    420
```

```
cctcttcac tcgctgccaa gggctacaga agtgtgcatc ccaaccttcc ttctgacaag     480
tcccaggatg ccacttcctc cagtgcagcc cagccggagg taatagttgt ccctctctac     540
ctggttaata ctgacagagg gcaagaaggc actgccagac ctccaacacc tctggggcct     600
cttggctgcg tccccacaat cccagcgact gcctctgccg cctcacctct gaccttcccg     660
actctagatg atttcattcc ccctcatctg cagaggtggc cccaccacag ccagccagcc     720
cgcgcctctg gctcctttgc ccccattagc cagacgccac catccttctc accaccacct     780
ccgctggtcc ctcctgcccc ggaggacctc cgcagagtct cggagcctga cctcacggga     840
gctgtttcga gtaccgattc cagtcctcta ctaaatgaag tttcttcttc ccttattgga     900
actgattccc aagcctttcc atcagttagc aagccttcat ccgcctatcc ctccacaacg     960
attgtcaatc ctactattgt gctcttgcaa cacaatcgag aacagcaaaa acgactcagt    1020
agcctttcag atcctgtctc agaaagaaga gtgggagagc aggactcagc accaacccag    1080
gaaaaaccca cctcacctgg caaggctatt gaaaaaagag caaaggatga cagtaggcgg    1140
gtggtgaaga gcactcagga cttaagcgat gtttccatgg atgaagtggg catcccactc    1200
cggaacactg agagatcaaa agactggtac aagactatgt taaacagat ccacaaactg    1260 aacagagaca ctcctgaaga aaaccttat ttccctacgt acaaattccc tgaacttcct    1320
gaaatccagc aaacttccga agagacaaag tcttgctctg tcatgtcacc caggctggag    1380
tgcagtggta cagtcatagc tcactgcagc ctcaaactcc tagactcaag caatcctccc    1440
acctcagcct cccaagtagc tgggactgca gatgatgatt cagatctgta ctctcccaga    1500
tactcatttt ctgaagacac aaaatctccc cttttctgtgc ctcgctcaaa aagtgagatg    1560
agctacattg atggtgagaa ggtagtcaag aggtcggcca cactacccct cccagcccgc    1620
tcttcctcac tgaagtcaag ctcagaaaga aatgactggg aacccccaga taagaaagta    1680
gacacaagaa atatcgtgc agagcccaag agcatttacg aatatcagcc tggcaagtct    1740
tccgttctga ccaacgaaaa gatgagtcgg gatataagcc cagaagagat agatttaaag    1800
aatgaacctt ggtataaatt cttttcggaa ttggagtttg ggaaaccgcc tcccaaaaag    1860
atatgggatt atactcctgg agactgctct atccttccta gagaggatag aaagactaat    1920
ctagacaaag atctcagcct ctgccagaca gagttagagg cagattaga aaaatggag    1980 acgcttaata aagcacccag tgcaaacgtg ccacagagct cagccatcag ccctactccg    2040
gaaatttctt cagagactcc tggatatata tattcttcca acttccatgc agtgaagagg    2100
gaatcagacg gggctcctgg ggatctcact agcttggaga atgagagaca aatttataaa    2160
agtgtcttgg aaggtggtga catccctctt cagggcctga gtgggctcaa gcgaccatcc    2220
agctctgctt ccactaaaga ttcagaatcg ccaagacatt ttataccagc tgattacttg    2280
gaatccacgg aagaatttat tcgaagacgt catgatgata aagagaaact tttagcggac    2340
cagagacgac ttaaacgcga gcaagaagag gctgatattg cagctcgacg ccacacaggc    2400
gtcattccga cgcaccatca gtttatcact aatgagcgct tgggacct cctcaatata    2460 gacgatactg caaaaaggaa atctgggtca gagatgagac ctgccagagc caaatttgac    2520
tttaaagctc agacactaaa ggagcttcct ctgcagaagg gagatattgt ttacatttat    2580
aagcaaattg atcagaactg gtatgaagga gaacaccacg gccgggtggg aatcttccca    2640
cgcacctaca tcgagcttct tcctcctgct gagaaggcac agcccaaaaa gttgacacca    2700
gtgcaggttt tggaatatgg agaagctatt gctaagttta cttaatgg tgatacacaa    2760 gtagaaatgt ccttcagaaa gggtgagagg atcacactgc tccggcaggt agatgagaac    2820
```

```
tggtacgaag ggaggatccc ggggacatcc cgacaaggca tcttccccat cacctacgtg    2880
gatgtgatca agcgaccact ggtgaaaaac cctgtggatt acatggacct gcctttctcc    2940
tcctccccaa gtcgcagtgc cactgcaagc ccacagccat ggcgcgaaga gagtggacaa    3000
tatgagagga aagcagagag gggggcaggc gaaagaggcc ctggtggacc caagatctct    3060
aagaagagct gcttgaagcc ttcagacgtg gtcaggtgcc tgagtactga acagagactc    3120
tcagatctca acacccctga ggagagccgg cccggcaagc ccctgggtag cgcttttcca    3180
ggaagtgagg ctgagcagac agagcggcat agaggtggcg agcaggcggg gaggaaagct    3240
gctcggagag gtgggagcca gcaacctcaa gcccagcagc gaagagtcac ccccgacagg    3300
agtcaaacct cacaagattt atttagctat caagcattat atagctatat accacagaat    3360
gatgatgagt tggaactccg cgatggagat atcgttgatg tcatgaaaaa atgtgacgat    3420
ggatggtttg ttggtacttc aagaaggaca aagcagtttg gtacttttcc aggcaactat    3480
gtaaaacctt tgtatctata agaagactga aaaccatgga gattattttt attggaggag    3540
gaagcatcat tcatgaaccg atcttttttag ttgagtcagt aggaaaatta atacagtgga    3600
taaagtaaga agcaaaagac agggacagag aagtgttgtg tttaaaaccc aagcctgtct    3660
aaggttactg tgtattagac agggccgaac tagtgtgctg agcaaaaaga attgaagcaa    3720
attgtattta cttagccgct tctgggagcc acttcagcct tcccctccc ctccacttct     3780 tgggtaatct gacctgaagc atagtccagg agcagagtta gccagaaatg cctcctgctg    3840
ccccagcctt agagagctcc catctcaatc attgagcctg aaggcttcaa gcccaagaat    3900
gcaacaagac ccccagccta catttctcag ctcccctgga gccagctgat cctgtaacgc    3960
tgctggaggt cagtctgagc taccaagact gtccctagac aaaggtggag tcccccacac    4020
tgcccaagac caaatccctc actcaacctg ctgaggtgtg gatggggaaa cagaggcaaa    4080
actgaggcac ctgatgcatt cagcctgctg tgcagcagtg ccattgactg ccctgatgtt    4140
cagagagaaa cgcacacaag gtttgcccat gagaattggg gagcagatgg ccaagcagat    4200
aggttatgtc tgtttctga gtgatgaagt caggaagccc tgtggctctg gaggccactt     4260
gtggttcatt cttttcccat atccttggct tttagaaatg gttaccttca ggacagtgca    4320
gctgcattta tcagagcact attgctaagt tttcttttct ggcttgtgtt tttctgggac    4380
agtttagaat tgggaggcct attctcatag aacaccaaaa atgatgttca gtgattcatt    4440
taacatacac caatgtactc tggctgctgg ggggacaacc ataagcaaga catgcccagg    4500
gtttgccgtg gctccagatc tactccctgt aggagttcaa ggatcacaca aacggtagta    4560 accaggggttg tgaatctgag tacaccctgg caaggcttct cttcagactg aagcagcaat    4620
tctgccacta ccagcagcaa ccaggacgtc tgttctttgt gggggccaga tcagaagaga    4680
gaggcccctg tgacgcccgg gctgcttggt cacaactctg tccaattcaa ggatgtttat    4740
cggcctctct tagatcctga gtgagacaaa tacagaaatg acccattccc tgcccaccag    4800
aaactcagag gtgattgggg agactgacac aggaaaatga acttaatcaa gagagactgt    4860
gatatgtgct aagaagggtg tgagggaggg agagatgaat tttccctgga gggatcctag    4920
aaagcattgt catattgcca tctccattag ctcacttttta aacaactagg gtgctggaag    4980
aacctttgtc tgagggtagt tcatagctgg aaatacttgg aatattttcc agagtctcta    5040
aactctcatc ttccccccaca gatacacatc caagctcaca aataggagta gcaattctag    5100
gtggtagggt tgtgtacgga acccctggct gtctgcatat atctcagaat taccccagga    5160
ccattgtccc aaagtctaga gtctttacag gtaggcaaaa tttgtttttca atgcctgtgc    5220
```

```
ctcagctgct gtcacaaata cccatcttag gatcccatca gcttcccatc ccccaccaga    5280
cagccacagt accctcactt tctccctatt gttctttcaa atcctgttct caggaaagaa    5340
actgccacta attcattcac actaaggtgt aaatgattga aataggaat gagttacctc    5400 ttcccacaga catttgtttt taagtatgac agagcagggc cttaatccca agggaaaagg    5460
ttatggaact ggaggggtg agctttctgg gtagaaggag acttcctgaa tttccttaaa     5520
acccagtaag agtaagacct gttgttttgg aaggtctgct ccaccatcta agagcactgt    5580
tttttttttt ttgttgttgt tgttgtttta cggtctctga gggaatatag taaaaatgca    5640
tatgcacgtg caatttgcac ggcagcattt caccgattgt ggactgtatt ggctaatgtg    5700
tttcctggtc tttagatgca aaccattaat aacactatct tatctcatag ttttttcagg    5760
ggtgcttctt gattagtagg gaattttgaa cacctcttta aatacagcta gaaataaaa    5820 ccaatttgta aagccacatt tgcatatgat gccagcctca cgcatttgta tatctccaga    5880
aattcaggta tgcctcacca atttgcccgt ctttaataaa atcttgtgtt aaaatttgca    5940
tcacgtcgcc ttcctatgta tgacgaaaca agaaacagag atttccaatt gctcttttgt    6000
cttcagacat ttagtaatat aaagtaccta tttttatgct gaaatgttta tacaggttta    6060
ttaatagcaa gtgcaactaa ctggcggcat gccttgcaac acattttgat atattagcca    6120
tgcttccggg taaaggcaag ccccaaactc cttatctttt gcagtctctc tgggatcagt    6180
aaaagaaaaa aaaaataatg tgcttaagaa gtgggactgt aaatatgtat atttaacttt    6240
gtatagccca tgtacctacc ttgtatagaa aaataatttt aaaaatttga atggaagggg   6300
gtaaaggaag tcatgaagtt tttttgcatt tttatttaaa tgaaggaatt ccaaataact    6360
cacctacaga tttttagcac aaaaatagcc attgtaaagt gttaaaattt acgataagta    6420
ttctattggg gaggaaaggt aactctgatc tcagttacag tttttttttc cttttttaatt   6480 tcattatttt gggttttgg ttttttgcagt cctatttatc tgcagtcgta ttaagtccta    6540
ttgctagaat aggttactac aaaaaaggtt atattctgaa agaaaaataa ctgacattat    6600
atataaccaa ttaatttaaa gtattgccat ttaaattaca cactgagagc atgtcctatg    6660
cagacataga ttttctgtt catttatttt tcttcattgc agtggattga tttgataaat     6720
agatgtgttg aattactaca tttgctgtac atattattta ataaacttta ttcagaattg    6780
cgtggcaaaa aaaaaaaaaa aaa                                            6803

<210> SEQ ID NO 11
<211> LENGTH: 905
<212> TYPE: PRT
<213> ORGANISM: Homo sapiens

<400> SEQUENCE: 11

Met Ser Ser Glu Cys Asp Gly Gly Ser Lys Ala Val Met Asn Gly Leu
1               5                   10                  15

Ala Pro Gly Ser Asn Gly Gln Asp Lys Ala Thr Ala Asp Pro Leu Arg
            20                  25                  30

Ala Arg Ser Ile Ser Ala Val Lys Ile Ile Pro Val Lys Thr Val Lys
        35                  40                  45

Asn Ala Ser Gly Leu Val Leu Pro Thr Asp Met Asp Pro Thr Lys Ile
    50                  55                  60

Cys Thr Gly Lys Gly Ala Val Thr Leu Arg Ala Ser Ser Ser Tyr Arg
65                  70                  75                  80

Glu Thr Pro Ser Ser Ser Pro Ala Ser Pro Gln Glu Thr Arg Gln His
                85                  90                  95
```

```
Glu Ser Lys Pro Gly Leu Glu Pro Pro Ser Ser Ala Asp Glu Trp
            100                 105                 110

Arg Leu Ser Ser Ser Ala Asp Ala Asn Gly Asn Ala Gln Pro Ser Ser
        115                 120                 125

Leu Ala Ala Lys Gly Tyr Arg Ser Val His Pro Asn Leu Pro Ser Asp
    130                 135                 140

Lys Ser Gln Arg Trp Pro His His Ser Gln Pro Ala Arg Ala Ser Gly
145                 150                 155                 160

Ser Phe Ala Pro Ile Ser Gln Thr Pro Pro Ser Phe Ser Pro Pro Pro
                165                 170                 175

Pro Leu Val Pro Pro Ala Pro Glu Asp Leu Arg Arg Val Ser Glu Pro
            180                 185                 190

Asp Leu Thr Gly Ala Val Ser Ser Thr Asp Ser Ser Pro Leu Leu Asn
        195                 200                 205

Glu Val Ser Ser Ser Leu Ile Gly Thr Asp Ser Gln Ala Phe Pro Ser
    210                 215                 220

Val Ser Lys Pro Ser Ser Ala Tyr Pro Ser Thr Thr Ile Val Asn Pro
225                 230                 235                 240

Thr Ile Val Leu Leu Gln His Asn Arg Glu Gln Gln Lys Arg Leu Ser
                245                 250                 255

Ser Leu Ser Asp Pro Val Ser Glu Arg Arg Val Gly Glu Gln Asp Ser
            260                 265                 270

Ala Pro Thr Gln Glu Lys Pro Thr Ser Pro Gly Lys Ala Ile Glu Lys
        275                 280                 285

Arg Ala Lys Asp Asp Ser Arg Arg Val Val Lys Ser Thr Gln Asp Leu
    290                 295                 300

Ser Asp Val Ser Met Asp Glu Val Gly Ile Pro Leu Arg Asn Thr Glu
305                 310                 315                 320

Arg Ser Lys Asp Trp Tyr Lys Thr Met Phe Lys Gln Ile His Lys Leu
                325                 330                 335

Asn Arg Asp Asp Asp Ser Asp Leu Tyr Ser Pro Arg Tyr Ser Phe Ser
            340                 345                 350

Glu Asp Thr Lys Ser Pro Leu Ser Val Pro Arg Ser Lys Ser Glu Met
        355                 360                 365

Ser Tyr Ile Asp Gly Glu Lys Val Val Lys Arg Ser Ala Thr Leu Pro
    370                 375                 380

Leu Pro Ala Arg Ser Ser Ser Leu Lys Ser Ser Ser Glu Arg Asn Asp
385                 390                 395                 400

Trp Glu Pro Pro Asp Lys Lys Val Asp Thr Arg Lys Tyr Arg Ala Glu
                405                 410                 415

Pro Lys Ser Ile Tyr Glu Tyr Gln Pro Gly Lys Ser Ser Val Leu Thr
            420                 425                 430

Asn Glu Lys Met Ser Arg Asp Ile Ser Pro Glu Glu Ile Asp Leu Lys
        435                 440                 445

Asn Glu Pro Trp Tyr Lys Phe Phe Ser Glu Leu Glu Phe Gly Lys Pro
    450                 455                 460

Pro Pro Lys Lys Ile Trp Asp Tyr Thr Pro Gly Asp Cys Ser Ile Leu
465                 470                 475                 480

Pro Arg Glu Asp Arg Lys Ser Ser Ala Ile Ser Pro Thr Pro Glu Ile
                485                 490                 495

Ser Ser Glu Thr Pro Gly Tyr Ile Tyr Ser Ser Asn Phe His Ala Val
            500                 505                 510

Lys Arg Glu Ser Asp Gly Ala Pro Gly Asp Leu Thr Ser Leu Glu Asn
```

```
                 515                 520                 525
Glu Arg Gln Ile Tyr Lys Ser Val Leu Glu Gly Gly Asp Ile Pro Leu
530                 535                 540

Gln Gly Leu Ser Gly Leu Lys Arg Pro Ser Ser Ala Ser Thr Lys
545                 550                 555                 560

Asp Ser Glu Ser Pro Arg His Phe Ile Pro Ala Asp Tyr Leu Glu Ser
                565                 570                 575

Thr Glu Glu Phe Ile Arg Arg His Asp Asp Lys Glu Lys Leu Leu
            580                 585                 590

Ala Asp Gln Arg Arg Leu Lys Arg Glu Gln Glu Glu Ala Asp Ile Ala
            595                 600                 605

Ala Arg Arg His Thr Gly Val Ile Pro Thr His His Gln Phe Ile Thr
610                 615                 620

Asn Glu Arg Phe Gly Asp Leu Leu Asn Ile Asp Asp Thr Ala Lys Arg
625                 630                 635                 640

Lys Ser Gly Ser Glu Met Arg Pro Ala Arg Ala Lys Phe Asp Phe Lys
                645                 650                 655

Ala Gln Thr Leu Lys Glu Leu Pro Leu Gln Lys Gly Asp Ile Val Tyr
            660                 665                 670

Ile Tyr Lys Gln Ile Asp Gln Asn Trp Tyr Glu Gly Glu His His Gly
675                 680                 685

Arg Val Gly Ile Phe Pro Arg Thr Tyr Ile Glu Leu Leu Pro Pro Ala
            690                 695                 700

Glu Lys Ala Gln Pro Lys Lys Leu Thr Pro Val Gln Val Leu Glu Tyr
705                 710                 715                 720

Gly Glu Ala Ile Ala Lys Phe Asn Phe Asn Gly Asp Thr Gln Val Glu
                725                 730                 735

Met Ser Phe Arg Lys Gly Glu Arg Ile Thr Leu Leu Arg Gln Val Asp
            740                 745                 750

Glu Asn Trp Tyr Glu Gly Arg Ile Pro Gly Thr Ser Arg Gln Gly Ile
            755                 760                 765

Phe Pro Ile Thr Tyr Val Asp Val Ile Lys Arg Pro Leu Val Lys Asn
770                 775                 780

Pro Val Asp Tyr Met Asp Leu Pro Phe Ser Ser Pro Ser Arg Ser
785                 790                 795                 800

Ala Thr Ala Ser Pro Gln Leu Ser His His Ser Leu Arg Ala Gly Pro
                805                 810                 815

Asp Leu Thr Glu Ser Glu Lys Ser Tyr Val Gln Pro Gln Ala Gln Gln
            820                 825                 830

Arg Arg Val Thr Pro Asp Arg Ser Gln Thr Ser Gln Asp Leu Phe Ser
            835                 840                 845

Tyr Gln Ala Leu Tyr Ser Tyr Ile Pro Gln Asn Asp Asp Glu Leu Glu
850                 855                 860

Leu Arg Asp Gly Asp Ile Val Asp Val Met Glu Lys Cys Asp Asp Gly
865                 870                 875                 880

Trp Phe Val Gly Thr Ser Arg Arg Thr Lys Gln Phe Gly Thr Phe Pro
                885                 890                 895

Gly Asn Tyr Val Lys Pro Leu Tyr Leu
            900                 905

<210> SEQ ID NO 12
<211> LENGTH: 6065
<212> TYPE: DNA
<213> ORGANISM: Homo sapiens
```

<400> SEQUENCE: 12

```
agcagttcag agccccagtt gcagacgact tgtcctgcca ccaccatgag ttctgaatgt      60
gatggtggtt ccaaagctgt gatgaatggc ttggcacctg gcagcaatgg gcaagacaaa     120
gcaactgccg acccttttacg cgcacgctct atttctgctg ttaaaatcat tcctgtgaag    180
acagtgaaaa acgcctcagg cctagttctc cctacagaca tggatcctac aaaaatctgc    240
actgggaagg gagcggtgac tctccgggcc tcgtcttcct acaggaaaac cccaagcagt    300
agccctgcga gccctcagga aacccggcaa cacgaaagca aaccaggtct ggagccagag    360
ccttcttcag cagatgagtg gaggctttct tccagtgctg atgccaatgg aaatgcccag    420
ccctcttcac tcgctgccaa gggctacaga agtgtgcatc ccaaccttcc ttctgacaag    480
tcccagaggt ggccccacca cagccagcca gcccgcgcct ctggctcctt tgcccccatt    540
agccagacgc caccatcctt ctcaccacca cctccgctgg tccctcctgc ccggaggac     600
ctccgcagag tctcggagcc tgacctcacg ggagctgttt cgagtaccga ttccagtcct    660
ctactaaatg aagtttcttc ttcccttatt ggaactgatt cccaagcctt tccatcagtt    720
agcaagcctt catccgccta tccctccaca acgattgtca atcctactat tgtgctcttg    780
caacacaatc gagaacagca aaaacgactc agtagccttt cagatcctgt ctcagaaaga    840
agagtgggag agcaggactc agcaccaacc caggaaaaac ccacctcacc tggcaaggct    900
attgaaaaaa gagcaaagga tgacagtagg cgggtggtga agagcactca ggacttaagc    960
gatgtttcca tggatgaagt gggcatccca ctccggaaca ctgagagatc aaaagactgg   1020
tacaagacta tgtttaaaca gatccacaaa ctgaacagag atgatgattc agatctgtac   1080
tctcccagat actcattttc tgaagacaca aaatctcccc tttctgtgcc tcgctcaaaa   1140
agtgagatga gctacattga tggtgagaag gtagtcaaga ggtcggccac actacccctc   1200
ccagcccgct cttcctcact gaagtcaagc tcagaaagaa atgactggga accccccagat  1260
aagaaagtag acacaagaaa atatcgtgca gagcccaaga gcatttacga atatcagcct   1320
ggcaagtctt ccgttctgac caacgaaaag atgagtcggg atataagccc agaagagata   1380
gatttaaaga atgaaccttg gtataaattc ttttcggaat tggagtttgg gaaaccgcct   1440
cccaaaaaga tatgggatta tactcctgga gactgctcta tccttcctag agaggataga   1500
aagagctcag ccatcagccc tactccgaaa atttcttcag agactcctgg atatatata    1560
tcttccaact ccatgcagt gaagagggaa tcagacgggg ctcctgggga tctcactagc    1620
ttggagaatg agagacaaat ttataaaagt gtcttggaag gtggtgacat ccctcttcag   1680
ggcctgagtg ggctcaagcg accatccagc tctgcttcca ctaaagattc agaatcgcca   1740
agacatttta taccagctga ttacttggaa tccacggaag aatttattcg aagacgtcat   1800
gatgataaag agaaacttct agcggaccag agacgactta acgcgagca agaagaggct     1860
gatattgcag ctcgacgcca cacaggcgtc attccgacgc accatcagtt tatcactaat    1920
gagcgctttg ggaccctcct caatatagac gatactgcaa aaggaaatc tgggtcagag    1980
atgagacctg ccagagccaa atttgacttt aaagctcaga cactaaagga gcttcctctg    2040
cagaagggag atattgttta catttataag caaattgatc agaactggta tgaaggagaa   2100
caccacggcc gggtgggaat cttcccacgc acctacatcg agcttcttcc tcctgctgag   2160
aaggcacagc ccaaaaagtt gacaccagtg caggttttgg aatatggaga agctattgct   2220
aagtttaact ttaatggtga tacacaagta gaaatgtcct tcagaaaggg tgagaggatc   2280
acactgctcc ggcaggtaga tgagaactgg tacgaaggga ggatcccggg gacatcccga   2340
```

```
caaggcatct tccccatcac ctacgtggat gtgatcaagc gaccactggt gaaaaaccct    2400
gtggattaca tggacctgcc tttctcctcc tccccaagtc gcagtgccac tgcaagccca    2460
cagctttctc atcattcatt gagagcagga ccagatctca cagaatctga aaagagctat    2520
gtgcaacctc aagcccagca gcgaagagtc accccgaca ggagtcaaac ctcacaagat     2580
ttatttagct atcaagcatt atatagctat ataccacaga atgatgatga gttggaactc    2640
cgcgatggag atatcgttga tgtcatggaa aaatgtgacg atggatggtt tgttggtact    2700
tcaagaagga caaagcagtt tggtactttt ccaggcaact atgtaaaacc tttgtatcta    2760
taagaagact gaaaaccatg gagattattt ttattggagg aggaagcatc attcatgaac    2820 cgatctttt agttgagtca gtaggaaaat taatacagtg gataaagtaa gaagcaaaag    2880
acagggacag agaagtgttg tgtttaaaac ccaagcctgt ctaaggttac tgtgtattag    2940
acagggccga actagtgtgc tgagcaaaaa gaattgaagc aaattgtatt tacttagccg    3000
cttctgggag ccacttcagc cttccccctc ccctccactt cttgggtaat ctgacctgaa    3060
gcatagtcca ggagcagagt tagccagaaa tgcctcctgc tgccccagcc ttagagagct    3120
cccatctcaa tcattgagcc tgaaggcttc aagcccaaga atgcaacaag accccccagcc   3180 tacatttctc agctcccctg gagccagctg atcctgtaac gctgctggag gtcagtctga    3240
gctaccaaga ctgtccctag acaaaggtgg agtcccccac actgcccaag accaaatccc    3300
tcactcaacc tgctgaggtg tggatgggga aacagaggca aaactgaggc acctgatgca    3360
ttcagcctgc tgtgcagcag tgccattgac tgccctgatg ttcagagaga aacgcacaca    3420
aggtttgccc atgagaattg gggagcagat ggccaagcag ataggttatg tctgtttct    3480 gagtgatgaa gtcaggaagc cctgtggctc tggaggccac ttgtggttca ttcttttccc    3540
atatccttgg cttttagaaa tggttacctt caggacagtg cagctgcatt tatcagagca    3600
ctattgctaa gttttctttt ctggcttgtg tttttctggg acagtttaga attgggaggc    3660
ctattctcat agaacaccaa aaatgatgtt cagtgattca tttaacatac accaatgtac    3720
tctggctgct gggggggacaa ccataagcaa gacatgccca gggttttgccg tggctccaga   3780 tctactcct gtaggagttc aaggatcaca caaacggtag taaccagggt tgtgaatctg     3840
agtacaccct ggcaaggctt ctcttcagac tgaagcagca attctgccac taccagcagc    3900
aaccaggacg tctgttcttt gtgggggcca gatcagaaga gagaggcccc tgtgacgccc    3960
gggctgcttg gtcacaactc tgtccaattc aaggatgttt atcggcctct cttagatcct    4020
gagtgagaca aatacagaaa tgacccattc cctgcccacc agaaactcag aggtgattgg    4080
ggagactgac acaggaaaat gaacttaatc aagagagact gtgatatgtg ctaagaaggg    4140 tgtgaggag ggagagatga attttccctg gagggatcct agaaagcatt gtcatattgc     4200
catctccatt agctcacttt taaacaacta gggtgctgga agaacctttg tctgagggta    4260
gttcatagct ggaaatactt ggaatatttt ccagagtctc taaactctca tcttccccca    4320
cagatacaca tccaagctca caaataggag tagcaattct aggtggtagg gttgtgtacg    4380 gaaccctgg ctgtctgcat atatctcaga attaccccag gaccattgtc ccaaagtcta     4440
gagtctttac aggtaggcaa aatttgtttt caatgcctgt gcctcagctg ctgtcacaaa    4500
tacccatctt aggatcccat cagcttccca tccccacca gacagccaca gtaccctcac     4560
tttctcccta ttgttctttc aaatcctgtt ctcaggaaag aaactgccac taattcattc    4620
acactaaggt gtaaatgatt gataatagga atgagttacc tcttcccaca gcatttgtt    4680 tttaagtatg acagagcagg gccttaatcc caagggaaaa ggttatggaa ctggaggggg    4740
```

```
tgagctttct gggtagaagg agacttcctg aatttcctta aaacccagta agagtaagac    4800
ctgttgtttt ggaaggtctg ctccaccatc taagagcact gttttttttt ttttgttgtt    4860
gttgttgttt tacggtctct gagggaatat agtaaaaatg catatgcacg tgcaatttgc    4920
acggcagcat ttcaccgatt gtggactgta ttggctaatg tgtttcctgg tctttagatg    4980
caaaccatta ataacactat cttatctcat agttttttca ggggtgcttc ttgattagta    5040
gggaattttg aacacctctt taaatacagc tagaaaataa aaccaatttg taaagccaca    5100
tttgcatatg atgccagcct cacgcatttg tatatctcca gaaattcagg tatgcctcac    5160
caatttgccc gtctttaata aaatcttgtg ttaaaatttg catcacgtcg ccttcctatg    5220
tatgacgaaa caagaaacag agatttccaa ttgctctttt gtcttcagac atttagtaat    5280
ataaagtacc tattttatg ctgaaatgtt tatacaggtt tattaatagc aagtgcaact    5340
aactggcggc atgccttgca acacattttg atatattagc catgcttccg ggtaaaggca    5400
agccccaaac tccttatctt ttgcagtctc tctgggatca gtaaaagaaa aaaaaaataa    5460
tgtgcttaag aagtgggact gtaaatatgt atatttaact ttgtatagcc catgtaccta    5520
ccttgtatag aaaaataatt ttaaaatttt gaatggaagg gggtaaagga agtcatgaag    5580
ttttttttgca ttttttattta aatgaaggaa ttccaaataa ctcacctaca gattttttagc    5640
acaaaaatag ccattgtaaa gtgttaaaat ttacgataag tattctattg gggaggaaag    5700
gtaactctga tctcagttac agtttttttt tccttttttaa tttcattatt ttgggttttt    5760
ggttttttgca gtcctatta tctgcagtcg tattaagtcc tattgctaga ataggttact    5820
acaaaaaagg ttatattctg aaagaaaaat aactgacatt atatataacc aattaattta    5880
aagtattgcc atttaaatta cacactgaga gcatgtccta tgcagacata gatttttctg    5940
ttcatttatt tttcttcatt gcagtggatt gatttgataa atagatgtgt tgaattacta    6000
catttgctgt acatattatt taataaactt tattcagaat tgcgtggcaa aaaaaaaaa    6060
aaaaa                                                                 6065
```

<210> SEQ ID NO 13
<211> LENGTH: 781
<212> TYPE: PRT
<213> ORGANISM: Homo sapiens

<400> SEQUENCE: 13

```
Met Ser Ser Glu Cys Asp Gly Gly Ser Lys Ala Val Met Asn Gly Leu
1               5                   10                  15

Ala Pro Gly Ser Asn Gly Gln Asp Lys Ala Thr Ala Asp Pro Leu Arg
            20                  25                  30

Ala Arg Ser Ile Ser Ala Val Lys Ile Ile Pro Val Lys Thr Val Lys
        35                  40                  45

Asn Ala Ser Gly Leu Val Leu Pro Thr Asp Met Asp Pro Thr Lys Ile
    50                  55                  60

Cys Thr Gly Lys Gly Ala Val Thr Leu Arg Ala Ser Ser Ser Tyr Arg
65                  70                  75                  80

Glu Thr Pro Ser Ser Pro Ala Ser Pro Gln Glu Thr Arg Gln His
                85                  90                  95

Glu Ser Lys Pro Gly Leu Glu Pro Glu Pro Ser Ser Ala Asp Glu Trp
            100                 105                 110

Arg Leu Ser Ser Ser Ala Asp Ala Asn Gly Asn Ala Gln Pro Ser Ser
        115                 120                 125

Leu Ala Ala Lys Gly Tyr Arg Ser Val His Pro Asn Leu Pro Ser Asp
    130                 135                 140
```

-continued

```
Lys Ser Gln Asp Ser Ser Pro Leu Leu Asn Glu Val Ser Ser Leu
145                 150                 155                 160

Ile Gly Thr Asp Ser Gln Ala Phe Pro Ser Val Ser Lys Pro Ser Ser
                165                 170                 175

Ala Tyr Pro Ser Thr Thr Ile Val Asn Pro Thr Ile Val Leu Leu Gln
            180                 185                 190

His Asn Arg Glu Gln Gln Lys Arg Leu Ser Ser Leu Ser Asp Pro Val
        195                 200                 205

Ser Glu Arg Arg Val Gly Glu Gln Asp Ser Ala Pro Thr Gln Glu Lys
    210                 215                 220

Pro Thr Ser Pro Gly Lys Ala Ile Glu Lys Arg Ala Lys Asp Asp Ser
225                 230                 235                 240

Arg Arg Val Val Lys Ser Thr Gln Asp Leu Ser Asp Val Ser Met Asp
                245                 250                 255

Glu Val Gly Ile Pro Leu Arg Asn Thr Glu Arg Ser Lys Asp Trp Tyr
            260                 265                 270

Lys Thr Met Phe Lys Gln Ile His Lys Leu Asn Arg Asp Asp Asp Ser
        275                 280                 285

Asp Leu Tyr Ser Pro Arg Tyr Ser Phe Ser Glu Asp Thr Lys Ser Pro
    290                 295                 300

Leu Ser Val Pro Arg Ser Lys Ser Glu Met Ser Tyr Ile Asp Gly Glu
305                 310                 315                 320

Lys Val Val Lys Arg Ser Ala Thr Leu Pro Leu Pro Ala Arg Ser Ser
                325                 330                 335

Ser Leu Lys Ser Ser Ser Glu Arg Asn Asp Trp Glu Pro Pro Asp Lys
            340                 345                 350

Lys Val Asp Thr Arg Lys Tyr Arg Ala Glu Pro Lys Ser Ile Tyr Glu
        355                 360                 365

Tyr Gln Pro Gly Lys Ser Ser Val Leu Thr Asn Glu Lys Met Ser Ser
    370                 375                 380

Ala Ile Ser Pro Thr Pro Glu Ile Ser Ser Glu Thr Pro Gly Tyr Ile
385                 390                 395                 400

Tyr Ser Ser Asn Phe His Ala Val Lys Arg Glu Ser Asp Gly Ala Pro
                405                 410                 415

Gly Asp Leu Thr Ser Leu Glu Asn Glu Arg Gln Ile Tyr Lys Ser Val
            420                 425                 430

Leu Glu Gly Gly Asp Ile Pro Leu Gln Gly Leu Ser Gly Leu Lys Arg
        435                 440                 445

Pro Ser Ser Ser Ala Ser Thr Lys Asp Ser Glu Ser Pro Arg His Phe
    450                 455                 460

Ile Pro Ala Asp Tyr Leu Glu Ser Thr Glu Glu Phe Ile Arg Arg Arg
465                 470                 475                 480

His Asp Asp Lys Glu Lys Leu Leu Ala Asp Gln Arg Arg Leu Lys Arg
                485                 490                 495

Glu Gln Glu Glu Ala Asp Ile Ala Ala Arg Arg His Thr Gly Val Ile
            500                 505                 510

Pro Thr His His Gln Phe Ile Thr Asn Glu Arg Phe Gly Asp Leu Leu
        515                 520                 525

Asn Ile Asp Asp Thr Ala Lys Arg Lys Ser Gly Ser Glu Met Arg Pro
    530                 535                 540

Ala Arg Ala Lys Phe Asp Phe Lys Ala Gln Thr Leu Lys Glu Leu Pro
545                 550                 555                 560

Leu Gln Lys Gly Asp Ile Val Tyr Ile Tyr Lys Gln Ile Asp Gln Asn
```

```
                     565                 570                 575
Trp Tyr Glu Gly Glu His His Gly Arg Val Gly Ile Phe Pro Arg Thr
            580                 585                 590

Tyr Ile Glu Leu Leu Pro Pro Ala Glu Lys Ala Gln Pro Lys Lys Leu
            595                 600                 605

Thr Pro Val Gln Val Leu Glu Tyr Gly Glu Ala Ile Ala Lys Phe Asn
            610                 615                 620

Phe Asn Gly Asp Thr Gln Val Glu Met Ser Phe Arg Lys Gly Glu Arg
625                 630                 635                 640

Ile Thr Leu Leu Arg Gln Val Asp Glu Asn Trp Tyr Glu Gly Arg Ile
                645                 650                 655

Pro Gly Thr Ser Arg Gln Gly Ile Phe Pro Ile Thr Tyr Val Asp Val
            660                 665                 670

Ile Lys Arg Pro Leu Val Lys Asn Pro Val Asp Tyr Met Asp Leu Pro
            675                 680                 685

Phe Ser Ser Ser Pro Ser Arg Ser Ala Thr Ala Ser Pro Gln Gln Pro
            690                 695                 700

Gln Ala Gln Gln Arg Arg Val Thr Pro Asp Arg Ser Gln Thr Ser Gln
705                 710                 715                 720

Asp Leu Phe Ser Tyr Gln Ala Leu Tyr Ser Tyr Ile Pro Gln Asn Asp
                725                 730                 735

Asp Glu Leu Glu Leu Arg Asp Gly Asp Ile Val Asp Val Met Glu Lys
            740                 745                 750

Cys Asp Asp Gly Trp Phe Val Gly Thr Ser Arg Arg Thr Lys Gln Phe
            755                 760                 765

Gly Thr Phe Pro Gly Asn Tyr Val Lys Pro Leu Tyr Leu
            770                 775                 780

<210> SEQ ID NO 14
<211> LENGTH: 5874
<212> TYPE: DNA
<213> ORGANISM: Homo sapiens

<400> SEQUENCE: 14
agcgctgagt cccagaaaaa cagagcgggg ccagctgcag cgtgtagtgc gagtggggcg      60
gacgcgcgca gcccgcccgc ccggcgacca gcaaggagtt ggcatccttt ggaagagttc     120
gtgaaagctt tctgcccaga gctcctggac caatgcatct tcccaccacc ttaaaccact     180
gagcagttca gagccccagt tgcagacgac ttgtcctgcc accaccatga gttctgaatg     240
tgatggtggt tccaaagctg tgatgaatgg cttggcacct ggcagcaatg gcaagacaa      300 agcaactgcc gacccttta c gcgcacgctc tatttctgct gttaaaatca ttcctgtgaa     360
gacagtgaaa aacgcctcag gcctagttct ccctacagac atggatccta caaaaatctg     420
cactgggaag ggagcggtga ctctccgggc ctcgtcttcc tacagggaaa ccccaagcag     480
tagccctgcg agccctcagg aaacccggca acacgaaagc aaaccaggtc tggagccaga     540
gccttcttca gcagatgagt ggaggctttc ttccagtgct gatgccaatg gaaatgccca     600
gccctcttca ctcgctgcca agggctacag aagtgtgcat cccaaccttc cttctgacaa     660
gtcccaggat ccagtcctc tactaaatga gtttcttct tcccttattg gaactgattc      720
ccaagccttt ccatcagtta gcaagccttc atccgcctat ccctcacaa cgattgtcaa      780 tcctactatt gtgcttcttgc aacacaatcg agaacagcaa aaacgactca gtagcctttc     840
agatcctgtc tcagaaagaa gagtgggaga gcaggactca gcaccaaccc aggaaaaacc     900
cacctcacct ggcaaggcta ttgaaaaaag agcaaaggat gacagtaggc gggtggtgaa     960
```

```
gagcactcag gacttaagcg atgtttccat ggatgaagtg ggcatcccac tccggaacac   1020
tgagagatca aaagactggt acaagactat gtttaaacag atccacaaac tgaacagaga   1080
tgatgattca gatctgtact ctcccagata ctcattttct gaagacacaa aatctcccct   1140
ttctgtgcct cgctcaaaaa gtgagatgag ctacattgat ggtgagaagg tagtcaagag   1200
gtcggccaca ctaccctcc cagcccgctc ttcctcactg aagtcaagct cagaaagaaa    1260
tgactgggaa cccccagata gaaagtaga cacaagaaaa tatcgtgcag agcccaagag    1320
catttacgaa tatcagcctg gcaagtcttc cgttctgacc aacgaaaaga tgagctcagc   1380
catcagccct actccggaaa tttcttcaga gactcctgga tatatatatt cttccaactt   1440
ccatgcagtg aagagggaat cagacggggc tcctggggat ctcactagct tggagaatga   1500
gagacaaatt tataaaagtg tcttggaagg tggtgacatc cctcttcagg gcctgagtgg   1560
gctcaagcga ccatccagct ctgcttccac taaagattca gaatcgccaa gacattttat   1620
accagctgat tacttggaat ccacggaaga atttattcga agacgtcatg atgataaaga   1680
gaaactttta gcggaccaga gacgacttaa acgcgagcaa aagaggctg atattgcagc    1740 tcgacgccac acaggcgtca ttccgacgca ccatcagttt atcactaatg agcgcttttgg  1800 ggacctcctc aatatagacg atactgcaaa aaggaaatct gggtcagaga tgagacctgc   1860
cagagccaaa tttgacttta agctcagac actaaaggag cttcctctgc agaagggaga    1920
tattgtttac atttataagc aaattgatca gaactggtat gaaggagaac accacggccg   1980
ggtgggaatc ttcccacgca cctacatcga gcttcttcct cctgctgaga aggcacagcc   2040
caaaaagttg acaccagtgc aggttttgga atatggagaa gctattgcta agtttaactt   2100
taatggtgat acacaagtag aaatgtcctt cagaaagggt gagaggatca cactgctccg   2160
gcaggtagat gagaactggt acgaagggag gatcccgggg acatcccgac aaggcatctt   2220
ccccatcacc tacgtggatg tgatcaagcg accactggtg aaaaaccctg tggattacat   2280
ggacctgcct ttctcctcct ccccaagtcg cagtgccact gcaagcccac agcaacctca   2340
agcccagcag cgaagagtca cccccgacag gagtcaaacc tcacaagatt tatttagcta   2400
tcaagcatta tatagctata taccacagaa tgatgatgag ttggaactcc gcgatggaga   2460
tatcgttgat gtcatggaaa aatgtgacga tggatggttt gttggtactt caagaaggac   2520
aaagcagttt ggtacttttc caggcaacta tgtaaaacct ttgtatctat aagaagactg   2580
aaaaccatgg agattatttt tattggagga ggaagcatca ttcatgaacc gatcttttta   2640
gttgagtcag taggaaaatt aatacagtgg ataaagtaag aagcaaaaga cagggacaga   2700
gaagtgttgt gtttaaaacc caagcctgtc taaggttact gtgtattaga cagggccgaa   2760
ctagtgtgct gagcaaaaag aattgaagca aattgtattt acttagccgc ttctgggagc   2820
cacttcagcc tttcccctcc cctccacttc ttgggtaatc tgacctgaag catagtccag   2880
gagcagagtt agccagaaat gcctcctgct gccccagcct tagagagctc ccatctcaat   2940
cattgagcct gaaggcttca agcccaagaa tgcaacaaga ccccccagcct acatttctca   3000 gctcccctgg agccagctga tcctgtaacg ctgctggagg tcagtctgag ctaccaagac   3060
tgtccctaga caaggtgga gtccccaca ctgcccaaga ccaaatccct cactcaacct     3120
gctgaggtgt ggatgggaaa acagaggcaa aactgaggca cctgatgcat tcagcctgct   3180
gtgcagcagt gccattgact gccctgatgt tcagagagaa acgcacacaa ggtttgccca   3240
tgagaattgg ggagcagatg gccaagcaga taggttatgt ctgttttctg agtgatgaag   3300
tcaggaagcc ctgtggctct ggaggccact tgtggttcat tcttttccca tatccttggc   3360
```

```
ttttagaaat ggttaccttc aggacagtgc agctgcattt atcagagcac tattgctaag   3420
ttttcttttc tggcttgtgt ttttctggga cagtttagaa ttgggaggcc tattctcata   3480
gaacaccaaa aatgatgttc agtgattcat ttaacataca ccaatgtact ctggctgctg   3540
gggggacaac cataagcaag acatgcccag ggtttgccgt ggctccagat ctactccctg   3600
taggagttca aggatcacac aaacggtagt aaccagggtt gtgaatctga gtacaccctg   3660
gcaaggcttc tcttcagact gaagcagcaa ttctgccact accagcagca accaggacgt   3720
ctgttctttg tgggggccag atcagaagag agaggcccct gtgacgcccg ggctgcttgg   3780
tcacaactct gtccaattca aggatgttta tcggcctctc ttagatcctg agtgagacaa   3840
atacagaaat gacccattcc ctgcccacca gaaactcaga ggtgattggg gagactgaca   3900
caggaaaatg aacttaatca agagagactg tgatatgtgc taagaagggt gtgagggagg   3960
gagagatgaa ttttccctgg agggatccta gaaagcattg tcatattgcc atctccatta   4020
gctcactttt aaacaactag ggtgctggaa gaacctttgt ctgagggtag ttcatagctg   4080
gaaatacttg gaatattttc cagagtctct aaactctcat cttcccccac agatacacat   4140
ccaagctcac aaataggagt agcaattcta ggtggtaggg ttgtgtacgg aaccccctggc   4200 tgtctgcata tatctcagaa ttaccccagg accattgtcc caaagtctag agtctttaca   4260
ggtaggcaaa atttgttttc aatgcctgtg cctcagctgc tgtcacaaat acccatctta   4320
ggatcccatc agcttcccat cccccaccag acagccacag taccctcact ttctccctat   4380 tgttcttttca aatcctgttc tcaggaaaga aactgccact aattcattca cactaaggtg   4440
taaatgattg ataataggaa tgagttacct cttcccacag acatttgttt ttaagtatga   4500
cagagcaggg cctaatccc aagggaaaag gttatggaac tggagggggt gagctttctg   4560
ggtagaagga gacttcctga atttccttaa aacccagtaa gagtaagacc tgttgttttg   4620
gaaggtctgc tccaccatct aagagcactg tttttttttt tttgttgttg ttgttgtttt   4680
acggtctctg agggaatata gtaaaaatgc atatgcacgt gcaatttgca cggcagcatt   4740
tcaccgattg tggactgtat tggctaatgt gttttcctggt ctttagatgc aaaccattaa   4800
taacactatc ttatctcata gttttttcag gggtgcttct tgattagtag ggaattttga   4860
acacctcttt aaatacagct agaaaataaa accaatttgt aaagccacat ttgcatatga   4920
tgccagcctc acgcatttgt atatctccag aaattcaggt atgcctcacc aatttgcccg   4980
tctttaataa aatcttgtgt taaaatttgc atcacgtcgc cttcctatgt atgacgaaac   5040
aagaaacaga gatttccaat tgctcttttg tcttcagaca tttagtaata taagtacct   5100 atttttatgc tgaaatgttt atacaggttt attaatagca agtgcaacta actggcggca   5160
tgccttgcaa cacattttga tatattagcc atgcttccgg gtaaaggcaa gccccaaact   5220
ccttatcttt tgcagtctct ctgggatcag taaaagaaaa aaaaaataat gtgcttaaga   5280
agtgggactg taaatatgta tatttaactt tgtatagccc atgtacctac cttgtataga   5340
aaaataattt taaaaatttg aatgaagggg ggtaaaggaa gtcatgaagt ttttttgcat   5400
ttttatttaa atgaaggaat tccaaataac tcacctacag attttttagca caaaaatagc   5460 cattgtaaag tgttaaaatt tacgataagt attctattgg ggaggaaagg taactctgat   5520
ctcagttaca gtttttttt cctttttaat ttcattattt tgggttttttg ttttttgcag   5580 tcctatttat ctgcagtcgt attaagtcct attgctagaa taggttacta caaaaaaggt   5640
tatattctga aagaaaaata actgacatta tatataacca attaatttaa agtattgcca   5700
tttaaattac acactgagag catgtcctat gcagacatag attttttctgt tcatttattt   5760
```

```
ttcttcattg cagtggattg atttgataaa tagatgtgtt gaattactac atttgctgta      5820
catattattt aataaacttt attcagaatt gcgtggcaaa aaaaaaaaaa aaaa           5874
```

<210> SEQ ID NO 15
<211> LENGTH: 740
<212> TYPE: PRT
<213> ORGANISM: Homo sapiens

<400> SEQUENCE: 15

```
Met Ser Ser Glu Cys Asp Gly Ser Lys Ala Val Met Asn Gly Leu
1               5                   10                  15

Ala Pro Gly Ser Asn Gly Gln Asp Lys Asp Met Asp Pro Thr Lys Ile
            20                  25                  30

Cys Thr Gly Lys Gly Ala Val Thr Leu Arg Ala Ser Ser Ser Tyr Arg
        35                  40                  45

Glu Thr Pro Ser Ser Ser Pro Ala Ser Pro Gln Glu Thr Arg Gln His
    50                  55                  60

Glu Ser Lys Pro Asp Glu Trp Arg Leu Ser Ser Ala Asp Ala Asn
65                  70                  75                  80

Gly Asn Ala Gln Pro Ser Ser Leu Ala Ala Lys Gly Tyr Arg Ser Val
                85                  90                  95

His Pro Asn Leu Pro Ser Asp Lys Ser Gln Asp Ser Ser Pro Leu Leu
            100                 105                 110

Asn Glu Val Ser Ser Ser Leu Ile Gly Thr Asp Ser Gln Ala Phe Pro
        115                 120                 125

Ser Val Ser Lys Pro Ser Ser Ala Tyr Pro Ser Thr Thr Ile Val Asn
    130                 135                 140

Pro Thr Ile Val Leu Leu Gln His Asn Arg Glu Gln Gln Lys Arg Leu
145                 150                 155                 160

Ser Ser Leu Ser Asp Pro Val Ser Glu Arg Arg Val Gly Glu Gln Asp
                165                 170                 175

Ser Ala Pro Thr Gln Glu Lys Pro Thr Ser Pro Gly Lys Ala Ile Glu
            180                 185                 190

Lys Arg Ala Lys Asp Asp Ser Arg Arg Val Val Lys Ser Thr Gln Asp
        195                 200                 205

Leu Ser Asp Val Ser Met Asp Glu Val Gly Ile Pro Leu Arg Asn Thr
    210                 215                 220

Glu Arg Ser Lys Asp Trp Tyr Lys Thr Met Phe Lys Gln Ile His Lys
225                 230                 235                 240

Leu Asn Arg Asp Asp Asp Ser Asp Leu Tyr Ser Pro Arg Tyr Ser Phe
                245                 250                 255

Ser Glu Asp Thr Lys Ser Pro Leu Ser Val Pro Arg Ser Lys Ser Glu
            260                 265                 270

Met Ser Tyr Ile Asp Gly Glu Lys Val Val Lys Arg Ser Ala Thr Leu
        275                 280                 285

Pro Leu Pro Ala Arg Ser Ser Ser Leu Lys Ser Ser Glu Arg Asn
    290                 295                 300

Asp Trp Glu Pro Pro Asp Lys Lys Val Asp Thr Arg Lys Tyr Arg Ala
305                 310                 315                 320

Glu Pro Lys Ser Ile Tyr Glu Tyr Gln Pro Gly Lys Ser Ser Val Leu
                325                 330                 335

Thr Asn Glu Lys Met Ser Ser Ala Ile Ser Pro Thr Pro Glu Ile Ser
            340                 345                 350

Ser Glu Thr Pro Gly Tyr Ile Tyr Ser Ser Asn Phe His Ala Val Lys
```

```
                355                 360                 365
Arg Glu Ser Asp Gly Ala Pro Gly Asp Leu Thr Ser Leu Glu Asn Glu
            370                 375                 380

Arg Gln Ile Tyr Lys Ser Val Leu Glu Gly Gly Asp Ile Pro Leu Gln
385                 390                 395                 400

Gly Leu Ser Gly Leu Lys Arg Pro Ser Ser Ser Ala Ser Thr Lys Asp
                405                 410                 415

Ser Glu Ser Pro Arg His Phe Ile Pro Ala Asp Tyr Leu Glu Ser Thr
            420                 425                 430

Glu Glu Phe Ile Arg Arg Arg His Asp Asp Lys Glu Lys Leu Leu Ala
        435                 440                 445

Asp Gln Arg Arg Leu Lys Arg Glu Gln Glu Glu Ala Asp Ile Ala Ala
    450                 455                 460

Arg Arg His Thr Gly Val Ile Pro Thr His His Gln Phe Ile Thr Asn
465                 470                 475                 480

Glu Arg Phe Gly Asp Leu Leu Asn Ile Asp Asp Thr Ala Lys Arg Lys
                485                 490                 495

Ser Gly Ser Glu Met Arg Pro Ala Arg Ala Lys Phe Asp Phe Lys Ala
            500                 505                 510

Gln Thr Leu Lys Glu Leu Pro Leu Gln Lys Gly Asp Ile Val Tyr Ile
        515                 520                 525

Tyr Lys Gln Ile Asp Gln Asn Trp Tyr Glu Gly His His Gly Arg
    530                 535                 540

Val Gly Ile Phe Pro Arg Thr Tyr Ile Glu Leu Leu Pro Pro Ala Glu
545                 550                 555                 560

Lys Ala Gln Pro Lys Lys Leu Thr Pro Val Gln Val Leu Glu Tyr Gly
                565                 570                 575

Glu Ala Ile Ala Lys Phe Asn Phe Asn Gly Asp Thr Gln Val Glu Met
            580                 585                 590

Ser Phe Arg Lys Gly Glu Arg Ile Thr Leu Leu Arg Gln Val Asp Glu
        595                 600                 605

Asn Trp Tyr Glu Gly Arg Ile Pro Gly Thr Ser Arg Gln Gly Ile Phe
    610                 615                 620

Pro Ile Thr Tyr Val Asp Val Ile Lys Arg Pro Leu Val Lys Asn Pro
625                 630                 635                 640

Val Asp Tyr Met Asp Leu Pro Phe Ser Ser Ser Pro Ser Arg Ser Ala
                645                 650                 655

Thr Ala Ser Pro Gln Gln Pro Gln Ala Gln Gln Arg Arg Val Thr Pro
            660                 665                 670

Asp Arg Ser Gln Thr Ser Gln Asp Leu Phe Ser Tyr Gln Ala Leu Tyr
        675                 680                 685

Ser Tyr Ile Pro Gln Asn Asp Asp Glu Leu Glu Leu Arg Asp Gly Asp
    690                 695                 700

Ile Val Asp Val Met Glu Lys Cys Asp Asp Gly Trp Phe Val Gly Thr
705                 710                 715                 720

Ser Arg Arg Thr Lys Gln Phe Gly Thr Phe Pro Gly Asn Tyr Val Lys
                725                 730                 735

Pro Leu Tyr Leu
            740

<210> SEQ ID NO 16
<211> LENGTH: 5570
<212> TYPE: DNA
<213> ORGANISM: Homo sapiens
```

```
<400> SEQUENCE: 16
agcagttcag agccccagtt gcagacgact tgtcctgcca ccaccatgag ttctgaatgt      60
gatggtggtt ccaaagctgt gatgaatggc ttggcacctg gcagcaatgg gcaagacaaa     120
gacatggatc ctacaaaaat ctgcactggg aagggagcgg tgactctccg ggcctcgtct     180
tcctacaggg aaaccccaag cagtagccct gcgagccctc aggaaacccg gcaacacgaa     240
agcaaaccag atgagtggag ctttcttcc agtgctgatg ccaatggaaa tgcccagccc      300
tcttcactcg ctgccaaggg ctacagaagt gtgcatccca accttccttc tgacaagtcc     360
caggattcca gtcctctact aaatgaagtt tcttcttccc ttattggaac tgattcccaa     420
gcctttccat cagttagcaa gccttcatcc gcctatccct ccacaacgat tgtcaatcct     480
actattgtgc tcttgcaaca caatcgagaa cagcaaaaac gactcagtag cctttcagat     540
cctgtctcag aaagaagagt gggagagcag gactcagcac caacccagga aaaacccacc     600
tcacctggca aggctattga aaaagagca aaggatgaca gtaggcgggt ggtgaagagc      660
actcaggact taagcgatgt ttccatggat gaagtgggca tcccactccg gaacactgag     720
agatcaaaag actggtacaa gactatgttt aaacagatcc acaaactgaa cagagatgat     780
gattcagatc tgtactctcc cagatactca ttttctgaag acacaaaatc tcccctttct     840
gtgcctcgct caaaaagtga gatgagctac attgatggtg agaaggtagt caagaggtcg     900
gccacactac ccctcccagc ccgctcttcc tcactgaagt caagctcaga agaaatgac      960
tgggaaccc cagataagaa agtagacaca agaaaatatc gtgcagagcc caagagcatt    1020
tacgaatatc agcctggcaa gtcttccgtt ctgaccaacg aaaagatgag ctcagccatc    1080
agccctactc cggaaatttc ttcagagact cctggatata tatattcttc caacttccat    1140
gcagtgaaga gggaatcaga cggggctcct ggggatctca ctagcttgga gaatgagaga    1200
caaattata aaagtgtctt ggaaggtggt gacatccctc ttcagggcct gagtgggctc    1260
aagcgaccat ccagctctgc ttccactaaa gattcagaat cgccaagaca ttttatacca    1320
gctgattact tggaatccac ggaagaattt attcgaagac gtcatgatga taaagagaaa    1380
cttttagcgg accagagacg acttaaacgc gagcaagaag aggctgatat tgcagctcga    1440
cgccacacag gcgtcattcc gacgcaccat cagtttatca ctaatgagcg ctttggggac    1500
ctcctcaata tagacgatac tgcaaaaagg aaatctgggt cagagatgag acctgccaga    1560
gccaaatttg actttaaagc tcagacacta aaggagcttc ctctgcagaa gggagatatt    1620
gtttacattt ataagcaaat tgatcagaac tggtatgaag agaacacca cggccgggtg    1680
ggaatcttcc cacgcaccta catcgagctt cttcctcctg ctgagaaggc acagcccaaa    1740
aagttgacac cagtgcaggt tttggaatat ggagaagcta ttgctaagtt taactttaat    1800
ggtgatacac aagtagaaat gtccttcaga aagggtgaga ggatcacact gctccggcag    1860
gtagatgaga actggtacga agggaggatc ccggggacat cccgacaagg catcttcccc    1920
atcacctacg tggatgtgat caagcgacca ctggtgaaaa accctgtgga ttacatggac    1980
ctgcctttct cctcctcccc aagtcgcagt gccactgcaa gccacagca acctcaagcc      2040
cagcagcgaa gagtcacccc cgacaggagt caaacctcac aagatttatt tagctatcaa    2100
gcattatata gctatatacc acagaatgat gatgagttgg aactccgcga tggagatatc    2160
gttgatgtca tggaaaaatg tgacgatgga tggtttgttg gtacttcaag aaggacaaag    2220
cagtttggta cttttccagg caactatgta aaaccttttgt atctataaga agactgaaaa    2280
ccatggagat tattttttatt ggaggaggaa gcatcattca tgaaccgatc tttttagttg    2340
```

-continued

```
agtcagtagg aaaattaata cagtggataa agtaagaagc aaaagacagg gacagagaag    2400
tgttgtgttt aaaacccaag cctgtctaag gttactgtgt attagacagg ccgaactag     2460
tgtgctgagc aaaaagaatt gaagcaaatt gtatttactt agccgcttct gggagccact    2520
tcagcctttc ccctcccctc cacttcttgg gtaatctgac ctgaagcata gtccaggagc    2580
agagttagcc agaaatgcct cctgctgccc cagccttaga gagctcccat ctcaatcatt    2640
gagcctgaag gcttcaagcc caagaatgca acaagacccc cagcctacat ttctcagctc    2700
ccctggagcc agctgatcct gtaacgctgc tggaggtcag tctgagctac caagactgtc    2760
cctagacaaa ggtggagtcc cccacactgc ccaagaccaa atccctcact caacctgctg    2820
aggtgtggat ggggaaacag aggcaaaact gaggcacctg atgcattcag cctgctgtgc    2880
agcagtgcca ttgactgccc tgatgttcag agagaaacgc acacaaggtt tgcccatgag    2940
aattggggag cagatggcca agcagatagg ttatgtctgt tttctgagtg atgaagtcag    3000
gaagccctgt ggctctggag gccacttgtg gttcattctt ttcccatatc cttggctttt    3060
agaaatggtt accttcagga cagtgcagct gcatttatca gagcactatt gctaagtttt    3120
cttttctggc ttgtgttttt ctgggacagt ttagaattgg gaggcctatt ctcatagaac    3180
accaaaaatg atgttcagtg attcatttaa catacaccaa tgtactctgg ctgctggggg    3240
gacaaccata agcaagacat gcccagggtt tgccgtggct ccagatctac tccctgtagg    3300
agttcaagga tcacacaaac ggtagtaacc agggttgtga atctgagtac accctggcaa    3360
ggcttctctt cagactgaag cagcaattct gccactacca gcagcaacca ggacgtctgt    3420
tctttgtggg ggccagatca aagagagag gcccctgtga cgcccgggct gcttggtcac     3480
aactctgtcc aattcaagga tgtttatcgg cctctcttag atcctgagtg agacaaatac    3540
agaaatgacc cattccctgc ccaccagaaa ctcagaggtg attggggaga ctgacacagg    3600
aaaatgaact taatcaagag agactgtgat atgtgctaag aagggtgtga gggagggaga    3660
gatgaatttt ccctggaggg atcctagaaa gcattgtcat attgccatct ccattagctc    3720
actttttaaac aactagggtg ctggaagaac ctttgtctga gggtagttca tagctggaaa   3780
tacttggaat attttccaga gtctctaaac tctcatcttc ccccacagat acacatccaa    3840
gctcacaaat aggagtagca attctaggtg gtagggttgt gtacggaacc cctggctgtc    3900
tgcatatatc tcagaattac cccaggacca ttgtcccaaa gtctagagtc tttacaggta    3960
ggcaaaattt gttttcaatg cctgtgcctc agctgctgtc acaaatacc atcttaggat      4020
cccatcagct tccatcccc caccagacag ccacagtacc ctcactttct ccctattgtt     4080
ctttcaaatc ctgttctcag gaaagaaact gccactaatt cattcacact aaggtgtaaa    4140
tgattgataa taggaatgag ttacctcttc ccacagacat ttgttttttaa gtatgacaga   4200
gcagggcctt aatcccaagg gaaaaggtta tggaactgga gggggtgagc tttctgggta    4260
gaaggagact tcctgaattt ccttaaaacc cagtaagagt aagacctgtt gttttggaag    4320
gtctgctcca ccatctaaga gcactgtttt ttttttttg ttgttgttgt tgttttacgg     4380
tctctgaggg aatatagtaa aaatgcatat gcacgtgcaa tttgcacggc agcatttcac    4440
cgattgtgga ctgtattggc taatgtgttt cctggtcttt agatgcaaac cattaataac    4500
actatcttat ctcatagttt tttcagggggt gcttcttgat tagtagggaa ttttgaacac   4560
ctctttaaat acagctagaa aataaaacca atttgtaaag ccacatttgc atatgatgcc    4620
agcctcacgc atttgtatat ctccagaaat tcaggtatgc ctcaccaatt tgcccgtctt    4680
taataaaatc ttgtgttaaa atttgcatca cgtcgccttc ctatgtatga cgaaacaaga    4740
```

```
aacagagatt tccaattgct cttttgtctt cagacattta gtaatataaa gtacctattt    4800
ttatgctgaa atgtttatac aggtttatta atagcaagtg caactaactg gcggcatgcc    4860
ttgcaacaca ttttgatata ttagccatgc ttccgggtaa aggcaagccc caaactcctt    4920
atcttttgca gtctctctgg gatcagtaaa agaaaaaaaa aataatgtgc ttaagaagtg    4980
ggactgtaaa tatgtatatt taactttgta tagcccatgt acctaccttg tatagaaaaa    5040
taattttaaa aatttgaatg aaggggggta aaggaagtca tgaagttttt ttgcattttt    5100
atttaaatga aggaattcca ataactcac ctacagattt ttagcacaaa aatagccatt     5160
gtaaagtgtt aaaatttacg ataagtattc tattggggag gaaaggtaac tctgatctca    5220
gttacagttt tttttttcctt tttaatttca ttattttggg tttttggttt ttgcagtcct   5280
atttatctgc agtcgtatta agtcctattg ctagaatagg ttactacaaa aaaggttata    5340
ttctgaaaga aaaataactg acattatata taaccaatta atttaaagta ttgccattta    5400
aattacacac tgagagcatg tcctatgcag acatagattt ttctgttcat ttattttct    5460 tcattgcagt ggattgattt gataaataga tgtgttgaat tactacatt gctgtacata    5520 ttatttaata aactttattc agaattgcgt ggcaaaaaaa aaaaaaaaa                5570
```

<210> SEQ ID NO 17
<211> LENGTH: 265
<212> TYPE: PRT
<213> ORGANISM: Homo sapiens

<400> SEQUENCE: 17

```
Met Ser Ser Glu Cys Asp Gly Gly Ser Lys Ala Val Met Asn Gly Leu
1               5                  10                  15

Ala Pro Gly Ser Asn Gly Gln Asp Lys Asp Met Asp Pro Thr Lys Ile
            20                  25                  30

Cys Thr Gly Lys Gly Ala Val Thr Leu Arg Ala Ser Ser Ser Tyr Arg
        35                  40                  45

Glu Thr Pro Ser Ser Ser Pro Ala Ser Pro Gln Glu Thr Arg Gln His
    50                  55                  60

Glu Ser Lys Pro Gly Leu Glu Pro Glu Pro Ser Ser Ala Asp Glu Trp
65                  70                  75                  80

Arg Leu Ser Ser Ser Ala Asp Ala Asn Gly Asn Ala Gln Pro Ser Ser
                85                  90                  95

Leu Ala Ala Lys Gly Tyr Arg Ser Val His Pro Asn Leu Pro Ser Asp
            100                 105                 110

Lys Ser Gln Asp Ala Thr Ser Ser Ala Ala Gln Pro Glu Val Ile
        115                 120                 125

Val Val Pro Leu Tyr Leu Val Asn Thr Asp Arg Gly Gln Glu Gly Thr
    130                 135                 140

Ala Arg Pro Pro Thr Pro Leu Gly Pro Leu Gly Cys Val Pro Thr Ile
145                 150                 155                 160

Pro Ala Thr Ala Ser Ala Ala Ser Pro Leu Thr Phe Pro Thr Leu Asp
                165                 170                 175

Asp Phe Ile Pro Pro His Leu Gln Arg Trp Pro His His Ser Gln Pro
            180                 185                 190

Ala Arg Ala Ser Gly Ser Phe Ala Pro Ile Ser Gln Thr Pro Pro Ser
        195                 200                 205

Phe Ser Pro Pro Pro Leu Val Pro Pro Ala Pro Glu Asp Leu Arg
    210                 215                 220

Arg Val Ser Glu Pro Asp Leu Thr Gly Ala Val Ser Ser Thr Val Ser
225                 230                 235                 240
```

Leu Leu Asp Ser Pro Pro His Gly Phe Ser Glu Cys Leu Leu Pro Ala
            245                 250                 255

Val Thr Phe Pro Phe Ser Leu Lys His
            260                 265

<210> SEQ ID NO 18
<211> LENGTH: 2088
<212> TYPE: DNA
<213> ORGANISM: Homo sapiens

<400> SEQUENCE: 18

| | | | | | |
|---|---|---|---|---|---|
| gtgtagtgcg | agtggggcgg | acgcgcgcag | cccgcccgcc | cggcgaccag | caagacggag | 60 |
| tctcactctg | tcgcccaggc | tggagtgcag | cggcgtgatc | ttggctcact | gcaaagtctg | 120 |
| cttccctggt | tcaagcgatt | gtcctgcctc | agcctcccga | gtagctggga | ttacaggagt | 180 |
| tggcatcctt | tggaagagtt | cgtgaaagct | ttctgcccag | agctcctgga | ccaatgcatc | 240 |
| ttcccaccac | cttaaaccac | tgagcagttc | agagccccag | ttgcagacga | cttgtcctgc | 300 |
| caccaccatg | agttctgaat | gtgatggtgg | ttccaaagct | gtgatgaatg | gcttggcacc | 360 |
| tggcagcaat | gggcaagaca | aagacatgga | tcctacaaaa | atctgcactg | gaagggagc | 420 |
| ggtgactctc | cgggcctcgt | cttcctacag | ggaaccccca | agcagtagcc | ctgcgagccc | 480 |
| tcaggaaacc | cggcaacacg | aaagcaaacc | aggtctggag | ccagagcctt | cttcagcaga | 540 |
| tgagtggagg | cttcttccca | gtgctgatgc | caatggaaat | gcccagccct | cttcactcgc | 600 |
| tgccaagggc | tacagaagtg | tgcatcccaa | ccttccttct | gacaagtccc | aggatgccac | 660 |
| ttcctccagt | gcagcccagc | cggaggtaat | agttgtccct | ctctacctgg | ttaatactga | 720 |
| cagagggcaa | gaaggcactg | ccagacctcc | aacacctctg | gggcctcttg | gctgcgtccc | 780 |
| cacaatccca | gcgactgcct | ctgccgcctc | acctctgacc | ttcccgactc | tagatgattt | 840 |
| cattcccct | catctgcaga | ggtggcccca | ccacagccag | ccagcccgcg | cctctggctc | 900 |
| ctttgccccc | attagccaga | cgccaccatc | cttctcacca | ccacctccgc | tggtccctcc | 960 |
| tgccccggag | gacctccgca | gagtctcgga | gcctgacctc | acgggagctg | tttcgagtac | 1020 |
| cgtaagcttg | ctggactccc | ctcctcacgg | cttttctgaa | tgtctcctcc | cagcagtcac | 1080 |
| attccctttc | tcactgaagc | actgagctct | gaggacagca | ctggctgccg | ctgtgcctgt | 1140 |
| gtgatgactg | gagccgtgtc | ccctgtcgct | agcgtgcatg | cttcccgtgt | gtcttccctg | 1200 |
| ggtctctcgg | ggctgttccc | catctctgca | gtgcctcatc | tgctctgtcc | tgttgggaat | 1260 |
| gcacatcttt | ctccctcaga | agacaacatc | tgtggccttt | atgttgactg | gccatgcttt | 1320 |
| tcacaggcca | ggtcgggggt | cgtgtggtga | gctgaggaaa | gctaagaatt | atggggaaa | 1380 |
| gcaacggcag | gcgtggtggg | tgctacttac | cagggagcgg | ggagatctcg | gggaggaagc | 1440 |
| gattctctga | ttctttttca | ttctcccagc | agccccatga | agtaactctt | cattttatca | 1500 |
| atgaggaata | tgaggttcag | agagattaag | taatatatgc | aagattacac | agtaagtagc | 1560 |
| agaaccagga | ttcaaaccta | ggtgtttggg | gctccattaa | cacaggcttt | tactcaacgc | 1620 |
| tgctatactg | ccctgcagat | tcctttcccc | ttcctgactc | tgtgttcttg | cttgtccct | 1680 |
| tcttgtccag | aggctctctg | gtatctgact | gcaggcattc | agcttcccct | gagtcagtcc | 1740 |
| tgcctcagtc | tgctaagcca | gtacctccca | gatggtgcct | ggaaatatat | agttagggac | 1800 |
| ccagcacggt | ggctcatgcc | tgtaatttca | gcactttggg | aggccgaggt | gggcagatca | 1860 |
| cctgaggtca | agagttcgag | accagcctgg | ccaacatagt | gaaaccctgt | ctttactaaa | 1920 |
| aatacaaaaa | aaaaaattag | ccagtgggcg | tgatggcagg | cgcctgtaat | cccagctact | 1980 |

```
tgggaggctg aggcaagaga atcacttgaa tctgggatgc agaggttgca gtgagccgag   2040
atcgcaccac tgcactccac catgggcaac agagtgagtc tctgtctc              2088
```

<210> SEQ ID NO 19
<211> LENGTH: 684
<212> TYPE: PRT
<213> ORGANISM: Homo sapiens

<400> SEQUENCE: 19

| | | | | | | | | | | | | | | |
|---|---|---|---|---|---|---|---|---|---|---|---|---|---|---|
| Met | Ser | Ser | Glu | Cys | Asp | Gly | Ser | Lys | Ala | Val | Met | Asn | Gly | Leu |
| 1 | | | | 5 | | | | | 10 | | | | | 15 |

| | | | | | | | | | | | | | | |
|---|---|---|---|---|---|---|---|---|---|---|---|---|---|---|
| Ala | Ser | Gly | Ser | Asn | Gly | Gln | Asp | Lys | Asp | Met | Asp | Pro | Thr | Lys | Ile |
| | | | 20 | | | | | 25 | | | | | 30 | | |

Cys Thr Gly Lys Gly Ala Val Thr Leu Arg Ala Ser Ser Tyr Arg
              35                  40                  45

Glu Thr Pro Ser Ser Pro Ala Ser Pro Gln Glu Thr Arg Gln His
 50                  55                  60

Glu Ser Lys Pro Gly Glu Trp Lys Leu Ser Ser Ala Asp Ala Asn
 65                  70                  75                  80

Gly Asn Ala Gln Pro Ser Ser Leu Ala Val Lys Gly Ser Arg Ser Val
              85                  90                  95

His Pro Asn Leu Pro Ser Asp Lys Ser Gln Asp Ser Ser Pro Leu Leu
              100                 105                 110

Asn Glu Val Ser Ser Ser Leu Ile Gly Thr Asp Ser Gln Ala Phe Ser
              115                 120                 125

Ser Glu Cys Lys Pro Ser Ser Ala Tyr Pro Ser Thr Thr Ile Val Asn
 130                 135                 140

Pro Thr Ile Val Leu Leu Gln His Asn Arg Glu Gln Gln Lys Arg Leu
 145                 150                 155                 160

Ser Ser Leu Ser Asp Pro Val Ser Glu Arg Arg Val Gly Glu Gln Asp
              165                 170                 175

Ser Ala Pro Thr Gln Glu Lys Pro Thr Ser Pro Gly Lys Ala Ile Glu
              180                 185                 190

Lys Arg Ala Lys Asp Asp Ser Arg Arg Val Val Lys Ser Thr Gln Asp
              195                 200                 205

Leu Ser Asp Val Ser Met Asp Glu Val Gly Ile Pro Leu Arg Asn Thr
 210                 215                 220

Glu Arg Ser Lys Asp Trp Tyr Lys Thr Met Phe Lys Gln Ile His Lys
 225                 230                 235                 240

Leu Asn Arg Asp Asp Asp Ser Asp Leu Tyr Ser Pro Arg Tyr Ser Phe
              245                 250                 255

Ser Glu Asp Thr Lys Ser Pro Leu Ser Val Pro Arg Ser Lys Ser Glu
              260                 265                 270

Met Ser Tyr Ile Asp Gly Val Lys Val Val Lys Arg Ser Ala Thr Leu
              275                 280                 285

Pro Leu Pro Ala Arg Ser Ser Ser Leu Lys Ser Ser Ser Glu Arg Asn
 290                 295                 300

Asp Trp Glu Pro Pro Asp Lys Lys Val Asp Thr Arg Lys Tyr Arg Ala
 305                 310                 315                 320

Glu Pro Lys Ser Ile Tyr Glu Tyr Gln Pro Gly Lys Ser Ser Val Leu
              325                 330                 335

Thr Asn Glu Lys Met Ser Ser Ala Ile Ser Pro Thr Pro Gly Ile Ser
              340                 345                 350

Ser Glu Thr Pro Gly Tyr Ile Tyr Ser Ser Asn Phe His Ala Val Lys

```
                355                 360                 365
Arg Glu Ser Asp Gly Ala Pro Gly Asp Leu Thr Ser Leu Glu Asn Glu
            370                 375                 380
Ser Gln Ile Tyr Lys Ser Val Leu Glu Gly Gly Val Ile Pro Leu Gln
385                 390                 395                 400
Asp Leu Ser Gly Leu Lys Arg Pro Ser Ser Ala Ser Thr Lys Asn
                405                 410                 415
Ser Glu Ser Pro Arg His Phe Ile Pro Ala Asp Tyr Leu Glu Ser Thr
                420                 425                 430
Glu Glu Phe Ile Arg Arg His Asp Asp Lys Glu Met Arg Pro Ala
            435                 440                 445
Arg Ala Lys Phe Asp Phe Lys Ala Gln Thr Leu Lys Glu Leu Pro Leu
450                 455                 460
Gln Lys Gly Asp Ile Val Tyr Ile Tyr Lys Gln Ile Asp Gln Asn Trp
465                 470                 475                 480
Tyr Glu Gly Glu His His Gly Arg Val Gly Ile Phe Pro Arg Thr Tyr
                485                 490                 495
Ile Glu Leu Leu Pro Pro Ala Glu Lys Ala Gln Pro Lys Lys Leu Thr
                500                 505                 510
Pro Val Gln Val Leu Glu Tyr Gly Glu Ala Ile Ala Lys Phe Asn Phe
            515                 520                 525
Asn Gly Asp Thr Gln Val Glu Met Ser Phe Arg Lys Gly Glu Arg Ile
            530                 535                 540
Thr Leu Leu Arg Gln Val Asp Glu Asn Trp Tyr Glu Gly Arg Ile Pro
545                 550                 555                 560
Gly Thr Ser Arg Gln Gly Ile Phe Pro Ile Thr Tyr Val Asp Val Ile
                565                 570                 575
Lys Arg Pro Leu Val Lys Asn Pro Val Asp Tyr Met Asp Leu Pro Phe
            580                 585                 590
Ser Ser Ser Pro Ser Arg Ser Ala Thr Ala Ser Pro Gln Gln Pro Gln
            595                 600                 605
Ala Gln Gln Arg Arg Val Thr Pro Asp Arg Ser Gln Thr Ser Gln Asp
            610                 615                 620
Leu Phe Ser Tyr Gln Ala Leu Tyr Ser Tyr Ile Pro Gln Asn Asp Asp
625                 630                 635                 640
Glu Leu Glu Leu Arg Asp Gly Asp Ile Val Asp Val Met Glu Lys Cys
                645                 650                 655
Asp Asp Gly Trp Phe Val Gly Thr Ser Arg Arg Thr Lys Gln Phe Gly
            660                 665                 670
Thr Phe Pro Gly Asn Tyr Val Lys Pro Leu Tyr Leu
            675                 680

<210> SEQ ID NO 20
<211> LENGTH: 2055
<212> TYPE: DNA
<213> ORGANISM: Homo sapiens

<400> SEQUENCE: 20
atgagttctg aatgtgatgg tggttccaaa gctgttatga atggcttggc atctggcagc    60
aatgggcaag acaaagacat ggatcctaca aaaatctgca ctgggaaggg agcggtgact   120
ctccgggcct cgtcttccta caggaaaacc ccaagcagta gccctgcgag ccctcaggaa   180
acccggcaac acgaaagcaa accaggtgaa tggaaacttt cttccagtgc tgatgccaat   240
ggaaatgccc agccctcttc actcgctgtc aagggctcta gaagtgtgca tcccaacctt   300
```

-continued

```
ccttctgaca agtcccagga ttccagtcct ctactaaatg aagtttcttc ttcccttatt      360
ggaactgatt cccaagcctt ttcatcagaa tgcaagcctt catccgccta tccctccaca      420
acgattgtca atcctacaat tgtgctcttg caacacaatc gagaacagca aaaacgactc      480
agtagccttt cagatcctgt ctcagaaaga agagtgggag agcaggactc agcaccaacc      540
caggaaaaac ccacctcacc tggcaaggct attgaaaaaa gagcaaagga tgacagtagg      600
cgggtggtga agagcactca ggacttaagc gatgtttcca tggatgaagt gggcatccca      660
ctccggaaca ctgagagatc aaaagactgg tacaagacta tgtttaaaca gatccacaaa      720
ctgaacagag atgatgattc agatctgtac tctcccagat actcattttc cgaagacaca      780
aaatctcccc tttctgtgcc tcgctcaaaa agtgagatga gctacattga cggtgtgaag      840
gtagtcaaga ggtcggccac actacccctc ccagcccgct cttcctcact gaagtcaagc      900
tcagaaagaa atgactggga acccccagat aagaaagtag atacaagaaa atatcgtgca      960
gagcccaaga gcatttacga atatcagcct ggcaagtctt ccgttctgac caacgaaaag     1020
atgagctcag ccatcagccc tactccggga atttcttcag agactcctgg atatatatat     1080
tcttccaact tccacgcagt gaagaggaa tcagacgggg ctcctgggga tctcactagc     1140
ttggagaatg agagccaaat ttataaaagt gtcttggaag gtggtgtcat ccctcttcag     1200
gacctgagtg ggctcaagcg accatccagc tctgcttcca ctaaaaattc agaatcgcca     1260
agacatttta taccagctga ttacttggaa tccacggaag aatttattcg aagacgtcat     1320
gatgataaag agatgagacc tgccagagcc aaatttgact ttaaagctca gacactaaag     1380
gagcttcctc tgcagaaggg agatattgtt tacatttata agcaaattga tcagaactgg     1440
tatgaaggag aacaccacgg ccgggtggga atcttcccac gcacctacat cgagcttctt     1500
cctcctgctg agaaggcaca gcccaaaaag ttgacaccag tgcaggtttt ggaatatgga     1560
gaagctattg ctaagtttaa ctttaatggt gatacacaag tagaaatgtc cttcagaaag     1620
ggtgagagga tcacactgct ccggcaggta atgagaaact ggtacgaagg gaggatcccg     1680
gggacatccc gacaaggcat cttccccatc acctacgtgg atgtgatcaa gcgaccactg     1740
gtgaaaaacc ctgtggatta catggacctg ccttttctcct cctccccaag tcgcagtgcc     1800
actgcaagcc cacagcaacc tcaagcccag cagcgaagag tcaccccga caggagtcaa      1860
acctcacaag atttatttag ctatcaagca ttatatagct atataccaca gaatgatgat     1920
gagttggaac tccgcgatgg agatatcgtt gatgtcatgg aaaaatgtga cgatggatgg     1980
tttgttggta cttcaagaag gacaaagcag tttggtactt ttccaggcaa ctatgtaaaa     2040
cctttgtatc tataa                                                      2055
```

<210> SEQ ID NO 21
<211> LENGTH: 19
<212> TYPE: DNA
<213> ORGANISM: Mus musculus

<400> SEQUENCE: 21
agacatggac cctaccaaa                                                   19

<210> SEQ ID NO 22
<211> LENGTH: 19
<212> TYPE: DNA
<213> ORGANISM: Mus musculus

<400> SEQUENCE: 22
gatgagctca gcagtcagc                                                   19